US009562078B2

(12) United States Patent
Hoffenberg et al.

(10) Patent No.: US 9,562,078 B2
(45) Date of Patent: Feb. 7, 2017

(54) METHODS FOR IDENTIFYING BROADLY NEUTRALIZING ANTIBODIES UTILIZING RECOMBINANT HIV-1 ENVELOPE GLYCOPROTEINS COMPRISING STABILIZING MUTATIONS

(71) Applicant: International AIDS Vaccine Initiative, New York, NY (US)

(72) Inventors: Simon Hoffenberg, Hartsdale, NY (US); Christopher L. Parks, Boonton, NJ (US); Alexei Carpov, Fairlawn, NJ (US)

(73) Assignee: INTERNATIONAL AIDS VACCINE INITIATIVE, New York, NY (US)

( * ) Notice: Subject to any disclaimer, the term of this patent is extended or adjusted under 35 U.S.C. 154(b) by 0 days.

(21) Appl. No.: 13/928,561

(22) Filed: Jun. 27, 2013

(65) Prior Publication Data
US 2014/0037681 A1    Feb. 6, 2014

Related U.S. Application Data

(60) Provisional application No. 61/664,990, filed on Jun. 27, 2012.

(51) Int. Cl.
| | |
|---|---|
| A61K 39/21 | (2006.01) |
| G01N 33/53 | (2006.01) |
| C12N 7/00 | (2006.01) |
| C07K 14/005 | (2006.01) |
| A61K 39/12 | (2006.01) |
| A61K 39/00 | (2006.01) |

(52) U.S. Cl.
CPC .......... C07K 14/005 (2013.01); A61K 39/12 (2013.01); A61K 39/21 (2013.01); C12N 7/00 (2013.01); G01N 33/53 (2013.01); A61K 2039/55516 (2013.01); C12N 2740/16122 (2013.01); C12N 2740/16134 (2013.01)

(58) Field of Classification Search
CPC ............... A61K 39/21; C12N 2740/16122; C12N 7/00; G01N 33/53
See application file for complete search history.

(56) References Cited

U.S. PATENT DOCUMENTS

2011/0262488 A1* 10/2011 Phogat ................. C07K 14/005
424/400

FOREIGN PATENT DOCUMENTS

WO    WO 2011/109511    9/2011

OTHER PUBLICATIONS

Wu, X., et al., Jan. 2006, Neutralization escape variants of human immunodeficiency virus type 1 are transmitted from mother to infant, J. Virol. 80(2):835-844.*
Li, M., et al., Aug. 2005, Human immunodeficiency virus type 1 env clones from acute and early subtype B infections for standardized assessments of vaccine-elicited neutralizing antibodies, J. Virol. 79(16):10108-10125.*
Walker, L. M., Sep. 2011, Broad neutralization coverage of HIV by multiple highly potent antibodies, Nature 477:466-470.*
Korber, B. T., et al., 1998, Numbering Positions in HIV Relative to HXB2CG, in Human Retroviruses and AIDS 1998: A Compilation and Analysis of Nucleic Acid and Amino Acid Sequences, Korber, B. T., et al., eds. Theoretical Biology and Biophysics Group, Los Alamos National Laboratory, Los Alamos, NM, pp. III/102-III/111.*
Finzi, A., et al., 2010, Conformational characterization of aberrant disulfide-linked HIV-1 gp120 dimers secreted from overexpressing cells, J. Virol. Methods 168:155-161.*
Finzi, A. et. al., "Conformational characterization of aberrant disulfide-linked HIV-1 gp120 dimers secreted from overexpressing cells," J. Virol. Meth., vol. 168, No. 1-2, pp. 155-161, Sep. 2010.
Hoffenberg, S. et. al., "Identification of an HIV-1 clade A Envelope that exhibits broad antigenicity and neutralization sensitivity and elicits antibodies targeting three distinct epitopes." J. Virology, vol. 87, No. 10, pp. 5372-5383. Mar. 2013.
Kulkarni, S. et. al., "Highly complex neutralizing determinants on a monophyletic lineage of newly transmitted subtype C HIV-1 env clone from India.", Virology, vol. 385, pp. 505-520. 2009.
Walker, L. et. al., "Broad neutralization coverage of HIV by multiple highly potent antibodies.", Nature, vol. 477, No. 7365, pp. 466-470. 2011.
Wu X. et. al., "Neutralization escape variants of human immunodeficiency virus type 1 are transmitted from mother to infant.", J. Virol., vol. 80, No. 2, pp. 835-844. 2006.

* cited by examiner

*Primary Examiner* — Jeffrey Parkin
(74) *Attorney, Agent, or Firm* — Vedder Price P.C.; Thomas J. Kowalski; Deborah L. Lu

(57) ABSTRACT

The present application relates to novel HIV-1 envelope glycoproteins which may be utilized as an HIV-1 vaccine immunogens, antigens for crystallization and for the identification of broad neutralizing antibodies. The present invention encompasses the preparation and purification of immunogenic compositions which are formulated into the vaccines of the present invention.

8 Claims, 22 Drawing Sheets

FIG. 1
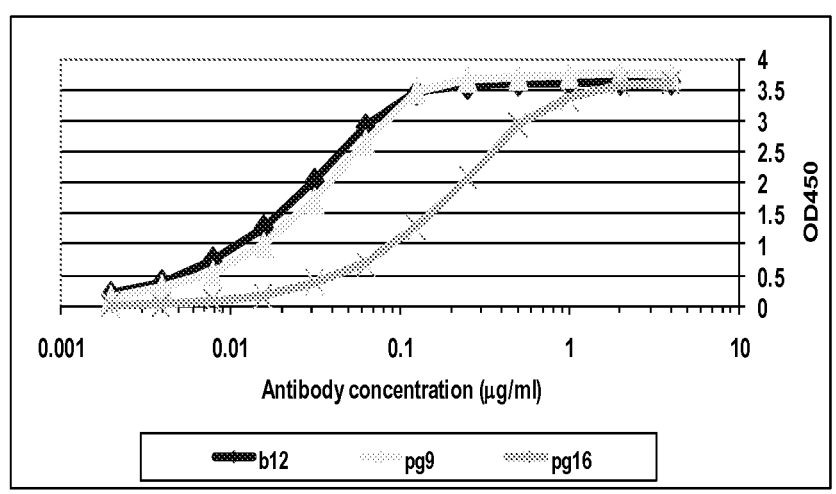
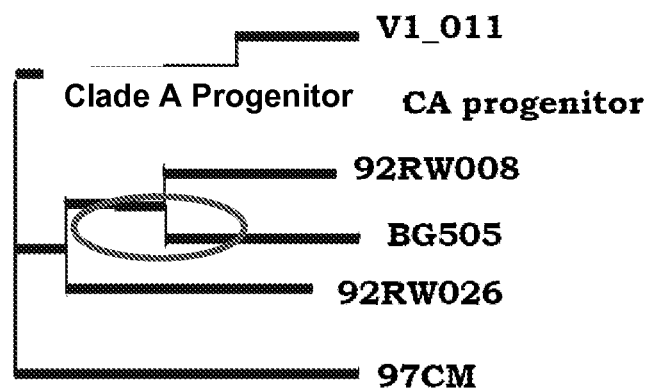

FIG. 2A

```
EF117267_GB    LWVTVYYGVPVWKEAKTTLFCASDAKAYEKEVHNVWATHACVPTDPNPQEMVLENVTENF
EF117271_GB    LWVTVYYGVPVWKEATTTLFCASDAKAYDKEVHNVWATHACVPTDPNPQEMVLGNVTENF
EF117273_GB    LWVTVYYGVPVWKEAKATLFCASDAKAYETEVHNVWATHACVPTDPNPQEIVLENVTENF
EF117265_NB    LWVTVYYGVPVWKEAKTTLFCASDAKAHEREVHNVWATYACVPTDPNPQEIVLKNVTENF
EF117268_GB    LWVTVYYGVPVWKEAKTTLFCASDAKAYEKEVHNVWATHACVPTDPNPQEMVLENVTENF
EF117266_WB    LWVTVYYGVPVWKEAKTTLFCASDAKAYETEVHNVWATHACVPTDPNPQEMVLGNVTENF
EF117270_NB    LWVTVYYGVPVWKEAKTTLFCASDAKAYETEVHNVWATHACVPTDPNPQELVLENVTENF
EF117269_WB    LWVTVYYGVPVWKEAKTTLFCASDAKAYEKEVHNVWATHACVPTDPNPQRIDL-NVTENF
EF117274_NB    LWVTVYYGVPVWKEAKTTLFCASDAKAYEKEVHNVWATHACVPTDPNPQEIVLGNVTEDF
AY423984_WB    LWVTVYYGVPVWKEAKTTLFCASDAKAYEREVHNVWATHACVPTDPNPQEMVLENVTENF
EF117272_NB    LWVTVYYGVPVWKEAKTTLFCASDAKGYDKEVHNVWATHACVPTDPNPQEMPLENVTENF
DQ411854_WB    LWVTVYYGVPVWKEAKTTLFCASDAKAYDKEVHNVWATHACVPTDPNPQEIVLNVTENF
DQ435682_WB    LWVTVYYGVPVWKEAKATLFCASDAKAYEKEVHNVWATHACVPTDPNPQEIYLGNVTENF
DQ388514_WB    LWVTVYYGVPVWKEAKTTLFCASDAKAYEKEVHNVWVTHACVPTDPNPQEMNLENVTENF
DQ388516_NB    LWVTVYYGVPVWREAKTTLFCASDAKAYEKEVHNVWATHACVPTDPNPQELVLENVTENF
DQ388517_WB    LWVTVYYGVPVWREAKTTLFCASDAKAYETEAHSVWATHACVPTDPNPQEMVLENVTENF
DQ435683_WB    LWVTVYYGVPVWKEAKTTLFCASDAKGYDTEVHNVWATHACVPTDPNPQEIVLENVTENF
DQ411853_WB    LWVTVYYGVPVWKEAKTTLFCASDAKAHREVHNIWATHACVPTDPNPQEIVLENVTENF
DQ388515_WB    LWVTVYYGVPVWKEAKATLFCASDAKAYEKEVHNVWATHACVPTDPNPQEIPLGNVTENF
AY424079_NB    LWVTVYYGVPVWREAKTTLFCASDAKAYEKEVHNVWATHACVPTDPNPQELVLGNVTENF
AY424138_GB    LWVTVYYGVPVWKEAKTTLFCASDAKGYEREVHNVWATHACVPTDPDQELVMANVTENF
AY835438_GB    LWVTVYYGVPVWKEATTTLFCASEAKAYDTEVHNVWATHACVPTDPNPQEVELGNVTENF
AY835450_WB    LWVTVYYGVPVWKEATTTLFCASDAKAYETEVHNVWATHACVPTDPNPQELVLENVTEYF
AY835449_WB    LWVTVYYGVPVWKEATTTLFCASDAKAYDQEIHNIWATHACVPTDPNPQRVELKNVTENF
AY835445_WB    LWVTVYYGVPVWKDASTTLFCASDAKAYDTEVHNVWATHACVPTDPNPQEVVLGNVTENF
AY835447_WB    LWVTVYYGVPVWKEANTTLFCASDAKAYDTEAHSVWATHACVPTDPNPQEVVLENVTENF
AY835451_WB    LWVTVYYGVPVWKEANTTLFCASDAKAYDTEVHNVWATHACVPTDPNPQEVVMGNVTEDF
AY835441_WB    LWVTVYYGVPVWKEATTTLFCASDAKAYETEKHNVWATHACVPTDPDPQEVVLGNVTENF
AY835439_NB    LWVTVYYGVPVWKEATTTLFCASDAKAYETEKHNVWATHACVPTDPNPQEVVLGNVTENF
JRCSF_WB       LWVTVYYGVPVWKETTTTLFCASDAKAYDTEVHNVWATHACVPTDPNPQEVVLENVTEDF
JRFL_NB        LWVTVYYGVPVWKEATTTLFCASDAKAYDTEVHNVWATHACVPTDPNPQEVVLENVTEHF
Bal_WB         LWVTVYYGVPVWKEATTTLFCASDAKAYDTEVHNVWATHACVPTDPNPQEVMENVTENF
HXBC2_WB       LWVTVYYGVPVWKEATTTLFCASDAKAYDTEVHNVWATHACVPTDPNPQEVVLNVTENF
SF162_NB       LWVTVYYGVPVWKEATTTLFCASDAKAYDTEVHNVWATHACVPTDPNPQEIVLENVTENF
AY835446_WB    --WVTVYYGVPVWKEANTTLFCASDAKAYNTEVHNVWATHACVPTDPNPQEVELENVTENF
AY835448_NB    LWVTVYYGVPVWKEAVTTLFCASDAKAYDTEVHNVWATHACVPTDPDPQEVVLENVTENF
AY835452_GB    LWVTVYYGVPVWKEATTTLFCASDAKGYEKEVHNVWATHACVPTDPNPQEVVLENVTENF
AY835444_WB    LWVTVYYGVPVWKEATTTLFCASDAKAYNTEVHNVWATHACVPTDPNPQEVGLENVTENF
               **********:::.:*******:*::..  * *.:*.*:*******:***:  : **** *
```

FIG. 2B

```
EF117267_GB  NMWENDVVDQMHEDVISLWDQSLKPCVKLTPLCVTLNCSKAKNITEEV--------IKNNTY
EF117271_GB  NMWKNEMVNQMHEDVISLWDQSLKPCVKLTPLCVTLECSN--------------VTYNES
EF117273_GB  NMWENDMVNQMHEDVISLWDQSLKPCVKLTPLCVTLDCENVDGND---------TYNGT
EF117265_NB  NMWENDMVDQMQEDVISLWDQSLKPCIKLTPLCVTLECTNVNIING--------TIHNET
EF117268_GB  NMWKNDMVDQMHEDVISLWDQSLKPCVKLTPLCVTLECRQVNTTN-AT-------SSVNVT
EF117266_NB  NMWKNDMVDQMHEDVISLWAQSLKPCVKLTPLCVTLECTQVNATQGNT--------TQVNVT
EF117270_NB  NMWRNDMVDQMHEDVISLWDQSLKPCVKLTPLCVTLECRNATS----------KMVNDT
EF117269_NB  NMWKNDMVDQMHEDVISLWDQSLKPCVKLTPLCVTLECTDANITCNST-------TSSNNC
EF117274_NB  NMWKNDMVDQMHEDVISLWDQSLKPCVKLTPLCVTLDC--ANVTSNIT------NGE---
AY423904_NB  NMWKNDMVDQMQEDIISLWDQSLKPCVKLTPLCVTLNCSKLNN-----------------
EF117272_NB  NMWENDMVNQMHEDVISLWDESLKPCVKLTPLCVTLNCTDVNKNVSSS------DTDNYK
DQ411854_NB  NMWKNDMVDQMHEDIISLWDQSLKPCVKLTPLCVTLNCKNVNISANANA----T-ATINSS
DQ435682_NB  NMWKNDMVDQMHEDIISLWDQSLKPCVKLTPLCVTLRCTN-----------------AFINGS
DQ388514_NB  NMWKNDMVDQMHEDIISLWDQSLKPCVKLTPLCVTLNCNVNRVTHN--------STYRNT
DQ388516_NB  NMWKNDMVNQMHEDIISLWDQSLKPCVKLTPLCVTLNCSNVNINETSID---FNVTSNIS
DQ388517_NB  NMWKNDMVDQMHEDVISLWDQSLKPCVKLTPLCVTLDCS---------------TYNNT
DQ435683_NB  NMWKNDMVDQMQDIISLWDQSLKPCVKLTPLCVTLNCSDA--------------TYRNG
DQ411853_NB  NMWKNDMVDQMHEDIISLWDQSLKPCVKLTPLCVTLNCSDVKIFGTNA-------TVNNA
DQ388515_NB  NMWKNDMADQMHEDIISLWDQSLKPCVKLTPLCVTLNCSDATSNTTRNATNTNTTSTDNR
AY424079_NB  NMWENDMVDQMHEDIISLWDQSLKPCVKLTPLCVTLECKNATR-------SNQTTYYDN-
AY424138_GB  NMWKNDMVDQMHEDIISLWDQSLKPCVKLTPLCVTLNCTSP-----------AAHNES
AY835438_GB  NMWKNDMVEQMHEDIISLWDQSLKPCVRLTPLCVTLDCTDLNN---------TTNTNNTT
AY835450_NB  DMWKNDMVEQMHEDIISLWDQSLKPCVKLTPLCVTLNCTDWTNGTDWN-----TTNSNNTT
AY835449_NB  NMWKSNMVDQMHEDIISLWDQSLKPCVKLTPLCVTLNCTDILNV---------TNSRSTD
AY835445_NB  NMWKNDMVDQMHEDIISLWDQSLKPCVKLTPLCVTLNCTDNIENT---------NENSSKNS
AY835447_NB  NMWKNDMVDQMHEDIISLWDQSLKPCVKLTPLCVTLNCTDLVR---------------S
AY835451_NB  NMWKNDMVDQMHEDIISLWDQSLKPCVKLTPLCVTLNCTNVTISS-------------T
AY835441_NB  NMWKNDMVEQMHEDIISLWDQSLKPCVKLTPLCVTLNCTDELANG---------TYANVTVT
AY835439_NB  NMWKNNMVEQMHEDIISLWDESLKPCVKLTPLCVTLNCTDEVKT--------SYANKTSN
JRCSF_NB     NMWKNNMVEQMQEDVINLWDQSLKPCVKLTPLCVTLNCKDVN-----------ATNTT
JRFL_NB      NMWKNNMVEQMQEDIISLWDQSLKPCVKLTPLCVTLNCKDVN-----------ATNTT
Bal_NB       NMWKNNMVEQMHEDIISLWDQSLKPCVKLTPLCVTLNCTDLRNAT--------SPNVTNTT
RXRC2_NB     NMWKNDMVEQMHEDIISLWDQSLKPCVKLTPLCVSLECTDLKR-----------DTNTN
SF162_NB     NMWKNNMVEQMHEDIISLWDQSLKPCVKLTPLCVTLHCTNLKN-----------ATNTK
AY835446_NB  NMWKNDMVDQMHEDIISLWDQSLKPCVKLTPLCVTLSCTDNVG-----------NDTST
AY835448_NB  NMWKNNMVEQMHEDIISLWDQSLKPCVKLTPLCVTLNCTDYNNTATNT----TSSATTTA
AY835452_GB  NMWKNNMVEQMHEDIISLWDQSLKPCVKLTPLCVTLNCSDVNT-------------TS
AY835444_NB  NMWKNDMVEQMHEDIISLWDQSLKPCVKLTPLCVTLNCSDLRNATN---------TTNFTV
             :**...:.:**::*:.:*  :*****::***:**:*  *
```

FIG. 2C

```
                              N156,S158,F159,N160,T162,  Y173,F176,V181
EF117267_GB       ----------KEDIKNCSFNATTEVKDKKQKVSALFYRLDIVPLNKPNSSESEEENSSGYY
EF117271_GB       ---------MKEVKNCSFNLTTELRDKKQKVSALFYRLDIVPLN-----DTEKKNSSRPY
EF117273_GB       ----------NE-MKNCSFNMTTELRDKKQKVSALFYRLDIVPLNR------SSSSNSSDYY
EF117265_NB       ---------YESMKNCSFNITTELKDKKQSVYALFYRLDIVPLN----------NSNEYY
EF117268_GB       ---------NGEEIKNCSFNATTELRDKKQKVYALFYRLDIVPLEE----ERKGNS---SKY
EF117266_WB       QV---------NGDEMKNCSFNVTTELRDKKQKAYALFYRLDIVPLER-----ENRGDSNSASKY
EF117270_NB       R--------NVEEMKNCSFNITTELRDRKQTVYASFYKLDIVPLNE------NKSTSSENY
EF117269_WB       TSYEINKEDMGEIKNCSFNTTPELIDKQKKYSALFYRLDIVSLEE--ENSSKKNDSMEYY
EF117274_NB       ----------EIKNCSFNATTDVRDKKKTVYSLFYRLDIVQLD------GRSNTSN--Y
AY423984_WB       ----------AFDQEMKNCSFNKTTELRDKRKQVYALFYKLDIVPLDG------RNNSSPY
EF117272_NB       --------ETMKERKNCTFNMTTELRDKNQKKYALFYKLDIVPLDD--------NDNAS-Y
DQ411854_WB       M----------NGEIKNCSFNKTTELRDKFQKVYALFYKPDVVPLN-------QGKHNETGKY
DQ435682_WB       L----------TEEVKNCSFNKTTELRDKKQKAYALFYRPDVVPLKK-----NSPSGNSSEY
DQ388514_WB       K----------GEQIKNCSFNITTELRDKKQKVYALFYKLDILPLN--------GNNDSKEY
DQ388516_NB       M---------KEEMKNCSFKVNSELRDKNRREHALFYKLDIVQLN--------DEGNDSYSY
DQ388517_WB       ----------SNIGKEMKNCSFNMTTELRDKRRKVNVLFYKLDIVPLTN--------SSNTTNY
DQ435683_WB       -------TNSTDTPNKNCSFNKTTELRDKKKNSYALFYRLDIVPLKNE--------SRSQNFSKY
DQ411853_WB       TYN--NNNTISDMNNCSFNITTTDKKFESYALYYRLDVVALDGKK-----TNSTNSSEY
DQ388515_WB       NATSNDTEMKGEIKNCFNKTTEEVRDRKTKQVYALFYKLDVPLEER--KNSSSKNSSYKEY
AY424079_NB       --------MDKEIKNCSFNVTTELTDKKKNMRALFYRADIEPLDGN-SNESINSSEGDKY
AY424138_GB       ---------ETRVKNCSFNITTDVKERKQKYNATFYDLDIVPLSS------SDNSSNSSLY
AY835438_GB       NTNSSKIEG-GEMKNCSFNITENRGDKRQKEYALLYRTDIVSIER----------TSSSY
AY835450_WB       ISKESTIEG-GEMKNCSFNVTTATGDKR-KESAFYKLDVAPIDN---------SNTSY
AY835443_WB       RSTNSSLEAKGEIKNCSFNYTPPRDKIQKEYAIFYKQDVVPIKN-----------DNTSY
AY835445_WB       STRSYNNSLEGGEMKNCSFNLTAGIRDKVFRKYALSYKLDYVPIEEQKDTN------KPTTY
AY835447_WB       RETRVGNFTEEKMKNCSFNVTGIRDKFQKEALAYKLAHVQIQNDNTSNK----SNTSY
AY835451_WB       NGSTANVTEEEEMKNCSFNTTPVIRDKIQKEVYALFYKLDYVPIK-GKNTN-------TGY
AY835441_WB       EK----------GEIKNCSFNIFFAIRDKVQRTYALFYKLDVVPIDNNSGNSSSN----YSNY
AY835439_NB       ETYKTSNETFGEIKNCGFSVPTGIKDKVQNVYALFYKLDVIPIDDNNNSSKNNNGSYSSY
JRCSF_WB          SSS-RGNMEFGEIKNCSFNVKSIRDKVQKEYALSYKLDVVPIDNK---------NNTKY
JRFL_NB           NDS-EGTMERGEIKNCSFNITTSIRDEVQKEYALFYKLDVVPIDN-----------NNTSY
Bal_WB            SSS-RGMVGGGEMKNCSFNATTGIRGKVQRKYALSYKLDIVPIDN---------KIDRY
BXBC2_WB          SSSGPMIMEKGEIKNCSFNYNSTSIRGKVQKEYAFYKLDIIPIDN---------DTTSY
SF162_NB          SSN-WKEMDRGEIKNCSFKVTTSIRNKMQKEYALHKLDVVPIDN-----------DNTSY
AY835446_WB       NNSRWDEMEKGEIKNCSFNATEGIRGKMQKRDALFYKLDYVPIERGKNNNS-----SFTDY
AY835448_NB       SSANKTAKEEAVMKNCSFNITTNVRDKVKREYALFYNLDVVKLEE----------GETSY
AY835452_GB       VNTTASSMEGGEIKNCSFNYTSMSDKMQKEYALFYTLDVVPIVK---------ENNTY
AY835444_WB       SSRVIKKEMGGEVKNCSFNVEDIRDKMQKVYALSYRPDYVPIQDRTIENNFIENNTTY
                            : *:*.    ..          ::    *:  :                    *
```

FIG. 2D

```
EF117267_GB   RLINCNTSAVTQACPKVTFDPIPIHYCTPAGYAILKCNEETFNGTGPCHNVSTVQCTHGI
EF117271_GB   RLINCNTSAITQACPKVTFDPIPIHYCTPAGYAILKCNDKKFNGTGPCHRVSTVQCTHGI
EF117273_GB   RLISCNTSAITQACPKVTFDPIPIHYCAPAGFAILKCNNKTFNGTGPCHNVSTVQCTHGI
EF117265_NB   RLINCNTSAIKQACPKVTFDPIPIHYCAPAGYAILKCNDKTFSGTGPCHNVSTVQCTHGI
EF117268_GB   RLINCNTSAITQACPKVTFDPIPIHYCAPAGYAILKCNNKTFNGTGPCNNVSTVQCTHGI
EF117266_NB   ILINCNTSAITQACPKVNFDPIPIHYCTPAGYAILKCNNKTFNGTGSCHNVSTVQCTHGI
EF117270_NB   RLINCNTSAITQACPKVNFDPIPIHYCTPAGYAILKCNNKTFNGTGPCSNVSTVQCTHGI
EF117269_NB   RLINCNTSAITQACPKVTFDPIPIHYCAPAGYAILKCNNKTFNGTGPCNNVSTVQCTHGI
EF117274_NB   RLINCNTSTITQACPKVSFDPIPIHYCAPAGYAILKCNNKTFNGKGPCHNISTVQCTHGI
AY423904_NB   RLINCNTSFITQACPKVSFDPIPIHYCAPAGYAILKCNNKTFNGTGPCHNVSTVQCTHGI
EF117272_NB   RLINCNTSLTQACPKVSFDPIPIHYCAPAGYAILKCKNKTFNGIGPCNKVSTVQCTHGI
DQ411854_NB   ILINCNSSTITQACPKVSFDPIPIHYCAPAGYAILKCNNKTFNGTGPCNNVSTVQCTHGI
DQ435682_NB   ILINCNTSFITQACPKVSFDPIPIHYCAPAGYAILKCNNKTFNGTGPCNNVSTVQCTHGI
DQ388514_NB   RLINCNTSAITQACPKVSFDPIPIHYCAPAGYAILKCNNKTFNGKGPCNNVSTVQCTHGI
DQ388516_NB   RLINCNTSTIKQACPKVSFEPIPIHYCAPAGYAILKCNNETFNGSGPCNNVSTVQCTHGI
DQ388517_NB   RLISCNTSFITQACPKVSFDPIPIHYCAPAGYAILKCNNKTFNGTGPCHNVSTVQCTHGI
DQ435683_NB   ILINCNTSTIAQACPKVSFDPIPIHYCAPAGYAILKCNNKTFNGTGPCNNVSTVQCTHGI
DQ411853_NB   RLINCNTSAVTQACPKVSFDPIPIHYCAPAGYAILKCNNKTFNGTGPCNNVSTVQCTHGI
DQ388515_NB   RLISCNTSFITQACPKVSFDPIPIHYCAPAGYAILKCNNKTFNGTGPCHNVSTVQCTHGI
AY424079_NB   ILINCNTSTIAQACPKVTFDPIPIHYCAPAGYAILKCNNKTFNGIGPCKNVSTVQCTHGI
AY424138_GB   RLISCNTSTITQACPKVSFDPIPIHYCAPAGYAILKCNNKTFSGKGPCSNVSTVQCTHGI
AY835438_GB   RLISCNTSVITQACPKVTFEPIPIHYCAPAGFAILKCNEDKFNGTGPCKNVSTVQCTHGI
AY835450_NB   RLISCNTSVITQACPKISFEPIPIHYCAPAGFAILKCNDKKFNGTGSCTNVSTVQCTHGI
AY835449_NB   RLISCNTSVITQACPKVTFEPIPIHYCAPAGFAILKCNDKGFNGTGPCTNVSTVQCTHGI
AY835445_NB   RLRSCNTSVITQACPKVTFEPIPIHYCAPAGFAILKCNDKKFNGTGPCTNVSTVQCTHGI
AY835447_NB   RLISCNTSVITQACPKISFEPIPIHFCAPAGFAILKCNDKKFNGTGPCTNVSTVQCTHGI
AY835451_NB   RLINCNTSVITQACPKVSFEPIPIHYCAPAGFAILKCNNKTFNGKGPCKNVSTVQCTHGI
AY835441_NB   RLINCNTSVITQACPKVSFEPIPIHYCAPAGFAILKCNNKKFNGTGPCKNVSTVQCTHGI
AY835439_NB   RLINCNTSVITQACPKVSFEPIPIHYCAPAGFAILKCNNKTFNGTGPCTNVSTVQCTHGI
JRCSF_NB      RLISCNTSVITQACPKVSFEPIPIHYCAPAGFAILKCNNKTFNGKGQCKNVSTVQCTHGI
JRFL_NB       RLISCDTSVITQACPKISFEPIPIHYCAPAGFAILKCNDKTFNGKGPCKNVSTVQCTHGI
Bal_NB        RLISCNTSVITQACPKVSFEPIPIHYCAPAGAILKCKDKKFNGKGPCTNVSTVQCTHGI
RXEC2_NB      RLISCNTSVITQACPKVSFEPIPIHYCAPAGFAILKCNNKTFNGTGPCTNVSTVQCTHGI
SF162_NB      KLINCNTSVITQACPKVSFEPIPIHYCAPAGFAILKCNDKKFNGSGPCTNVSTVQCTHGI
AY835446_NB   RLISCNTSVITQACPKVTFEPIPIHYCAPAGFAILKCKDKKFNGTGPCRNVSTVQCTHGI
AY835448_NB   RLVSCNTSVVTQACPKITFEPIPIHYCAPAGFAILKCNNKTFNGTGPCTNVSTVQCTHGI
AY835452_GB   RLISCNTSVITQACPKVSFEPIPIHYCAPAGFAILMCNNKTFDGKGPCNNVSTVQCTHGI
AY835444_NB   RLISCNTSVITQACPKISFEPIPIHYCTPAGFAILKCNDKKFNGSGPCTNVSTVQCTHGI
              * .:::*.: ****:.*:*****:*:***:*:* *::. *.* * * ::*********
```

FIG. 2E

```
                                                                P299, K305
EF117267_GB    KPVVSTQLLLNGSLAEG-EIIIRSKNLTDNAKTIIVHLNQSVEIVCTRPNENRKSIRI-
EF117271_GB    KPVVSTQLLLNGSLAEG-EIIIRSENLTNNAKTIIVHLNQSVEIVCARPSNNTTSIRI-
EF117273_GB    KPVVSTQLLLNGSLAEK-EIIIRSKNLSDNVKTIIVHLNESVEIVCTRPNNNTRKSIRI-
EF117265_NB    KPVVSTQLLLNGSLAEG-EIIIRSKKLDDNANTIIVHLDEPVKIECTRPNNNTRKSIRI-
EF117268_GB    KPVVSTQLLLNGSLAEG-EIIIRSENLTNNVKTIIVHLNESVEIVCTRPNNNTRKSIRI-
EF117266_WB    KPVVSTQLLLNGSLAEG-EIIIRSENLTDNVKTIIVHLDQSVEIVCTRPNNNTRKSIRI-
EF117270_NB    KPVVSTQLLLNGSLAEE-GIIIRSENLTDNVKTIIVHLEEPVEIVCTRPNNNTRKSVRI-
EF117269_WB    KPVVSTQLLLNGSLAEE-EIIIRSENLTNNAKIIIVHLNQAVEIVCTRPGNNTSKSIRI-
EF117274_NB    KPVVSTQLLLNGSLAEE-EIIIRSENLTNNVKTIIVHLNKPVKIVCTRPGNNTRKSIRI-
AY423984_WB    KPVISTQLLLNGSTAEE-DIIIRSENLTDNAKTIIVHLDESIEIRCTRPGNNTRKSIRI-
EF117272_NB    KPVVSTQLLLNGSLAEE-DIVIRSENITDNAKTIIVHLNESVEIVCIRPNNNTRKSIRI-
DQ411854_WB    KPVVSTQLLLNGSLAEE-EIIVRSENLTNNIKTIIVHLNKSVEIKCTRPNNNTRKSVRI-
DQ435682_WB    KPVVSTQLLLNGSLAEE-DIIIRSENLTNNIKTIIVHLNESVEIVCRRPNNNTRKSIRI-
DQ388514_WB    KPVVSTQLLLNGSLAEE-EIIIRSENITDNVEIIIVHLNESVEINCTRPNNNTRKSIRI-
DQ388516_NB    KPVVSTQLLLNGSLAEK-EIMIRSENLTNNAKTIIVQLTEAVNITCMRPGNNTRRSVRI-
DQ388517_WB    KPVVSTQLLLNGSLAEE-EIIIRSENLTDNVKIIIVQLNETINITCTRPNNNTRKSIRI-
DQ435683_WB    KPVVSTQLLLNGSLAEE-EVVIRSENISNNVETIIVHLNESVNITCIRPGNNTSRSIRI-
DQ411853_WB    KPVVSTQLLLNGSLAEE-EVVIRFENLTNNAKIIIVHLNESVEINCTRPSNNTRKSVRI-
DQ388515_WB    KPVVSTQLLLNGSLAEE-EIIIRSENLTDNTKTIIVHLNESVEIBCVRPNNNTRSVRI-
AY424079_NB    KPVVSTQLLLNGSLSEE-GIIIRSKNLTDNTKTIIVHLNESVAIVCTRPNNNTRKSIRI-
AY424138_GB    RPVVSTQLLLNGSLAEE-EIVIRSENLTDNAKTIIVHLNKSVEIECIRPGNNTRKSIRL-
AY835438_GB    RPTVSTQLLLNGSLAKE-EVVIRSANLSDNAKIIIVQLKDPVEINCTRPNNNTRKSINL-
AY835450_WB    RPVVSTQLLLNGSLAEE-EVVIRSKNFSDNAKIIIVQLGESVPINCTRPNNNTRKSIRI-
AY835449_WB    RPAISTQLLLNGSLAED-KVVIRSENFTDNAKIIIVHLNETVKINCTRPNNNTRKSIRI-
AY835445_WB    RPVVSTQLLLNGSLAEE-EVVIRSENFTNNAKTIIVQLNESIAINCTRPNNNTRKSIRI-
AY835447_WB    RPVVSTQLLLNGSLAEE-EVVIRSENFTDNVKNIIVQLNESVQINCTRPNNNTRKSINI-
AY835451_WB    KPVVSTQLLLNGSLAEE-DIIIRSENFTNNGKNIEVQLKEPVKINCTRPGNNTRSINI-
AY835441_WB    RPVVSTQLLLNGSLAEE-EVVIRSENFTDNAKTIIVQLNDSVIINCTRPNNNTRKGITI-
AY835439_NB    RPVVSTQLLLNGSLAEE-EVVIRSENFTNNAKTIIVHLKKSVEINCTRPGNNTRKSIHI-
JPCSF_WB       RPVVSTQLLLNGSLAEE-KVVIRSDNFTDNAKTIEVQLNESVEINCTRPSNNTRKSIHI-
JRFL_NB        RPVVSTQLLLNGSLAEE-EVVIRSDNFTNNAKTIIVQLKESVEINCTRPNNNTRKSIHI-
Bal_WB         RPVVSTQLLLNGSLAEE-EVVIRSENFTNNAKIIIVQLNESVEINCTRPNNNTRKSIRI-
HXBC2_WB       RPVVSTQLLLNGSLAEE-EVVIRSVNFTDNAKTIEVQLSTSVEINCTRPNNNTRKRIRIQ
SF162_NB       RPVVSTQLLLNGSLAEE-GVVIRSENFTDNAKTIIVQLKESVEINCTRPNNNTRKSITI-
AY835446_WB    KPVVSTQLLLNGSLAEE-EVVIRSENFSNNAKTIIVQLNTSVEIFCIRPNNNTRKGIRI-
AY835448_NB    KPVVSTQLLLNGSLAEGGEVMIRSANFTNNAKTIIVQLSKSVAINCTRPNNNTSKSIHM-
AY835452_GB    KPVVSTQLLLNGSLAEE-EVVIRSDNFTDNAKTIIVHLNESIRITCTRPNNNTSKSITI-
AY835444_WB    RPVVSTQLLLNGSPAEE-EVIIRSENFTNNAKTIIVQLNKTVEINCTRPNNNTRKSISI-
               :*.:********* ::   :::: :: :*. ***:*  .: * *  :*   : :
```

FIG. 2F

```
EF117267_GB    -GPGQAFYATGDIIGDIRQARCNISEEKWNETLQRVGKKLAEHFPN--KTIKFKSSGGD
EF117271_GB    -GPGQTFYATGAITGDIRQAHCNISKDKWNETLQRVGEKLAEHFPN--KTIKFNSSSGGD
EF117273_GB    -GPGQTFYATGAIIGNIREAHCNISRDKWNETLQRVGKKLEEQFPN--KTINFTSSSGGD
EF117265_NB    -GPGQTFYATGEIIGNIRQAHCDISEDQWNETLQRVGKKLAELFPN--KTITFNSSSGGD
EF117268_GB    -GPGQTFYATGDIIGNIRQAYCNIKKDDWIRTLQRVGKKLAEHFPR--RIINFTSPAGGD
EF117266_WB    -GPGQTFYATGDIIGNIREAHCNISEKKWREMLRKVSEKLAEHFPN--KTIKFTSSSGGD
EF117270_NB    -GPGQTFYATGEIIGDIRQAHCNISEAKWNETLQNVTKKLKEHFPN--KTIIFNSSSGGD
EF117269_WB    -GPGQTFYATGDIIGDIRQAHCNISEAKWNKTLREVSKKLAEHFPN--KTIIFNSSSGGD
EF117274_NB    -GPGQTFYATGEIIGNIRQAHCNISKEEWNKTLQGVGEKLAEHFPN--KTIEFTSPSGGD
AY423984_WB    -GPGQAFYATTNIIGDIRQAYCIINKANWFNTLRKVSKKLEEAFPN--KTINFNSSSGGD
EF117272_NB    -GPGQTFYATGDIVGDIRQAYCNISEGKWNKTLQRVSEKLAEHFPN--STINFNSSSGGD
DQ411854_WB    -GPGQTFYATGEIIGDIREAHCNISRETWNSTLIQVKEELREHY-N--KTIKFEPSSGGD
DQ435682_WB    -GPGQAFYATGDIIGDIRQAHCNINDSTWNRTLEQIEKKLREAFLN--KTIEFEPSSGGD
DQ388514_WB    -GPGQTFYATGEIIGKIREAHCNISKEKWNETILRVAKKLREAFPG--KAIKFEPSSGGD
DQ388516_NB    -GPGQTFYATGEIIGDIRQAHCNISKDKWNQILQNVRAKLGEHFHD--KTIKFEPSSGGD
DQ388517_WB    -GPGQSFYATGEIVGNIREAHCNISAGKWNKTLERVRTKLREHFPN--KTIEFEPSSGGD
DQ435683_WB    -GPGQAFYAMGDIIGNIREAHCNISEKAWNETIKKVVEKLVKYFPN--KTIRFAPPVGGD
DQ411853_WB    -GPGQTFYATGDIIGDIRQAHCNISRKKWNTTLQPVKEELREKFPN--KTIQFAPSSGGD
DQ388515_WB    -GPGQTFYATGEIIGDIRQAHCDLSKGNWFTTLRRIEKKLKEHFNN--ATIKFESSAGGD
AY424079_NB    -GPGQTFYATGEVIGDIREQWNRTLERIKDKLTEYFPD--KIIKFNHSSGGD
AY424138_GB    -GPGQTFYATGDVIGDIRKAYCKINGSEWNETLTKVSEKLKEYF-N--KTIRFAQHSGGD
AY835438_GB    -GPGRAFYATGDIIGDIRQAHCNISRAKWNDTLREIAKKLAEQFPN--RTIVFNQSSGGD
AY835450_WB    -GPGRAWYATGDIIGDIRKAYCNISRAKWNNTLKQITEKLREQFNK--TIIVFNQPSGGD
AY835449_WB    -APGRAFYATGEIIGDIRKAYCTINESEWNNTLQKIVVTLPEQFPN--KTIVFNQSSGGD
AY835445_WB    -GPGRAFYATGDIIGDIRQAHCNISREKWNSTLPQIVTELREQLGDFNKTIIFNQSSGGD
AY835447_WB    -GPGRAFYATGKIIGDIRQAHCNISPEKWQNTLKQIVKKLREQFK--NKTIAFAPSSGGD
AY835451_WB    -GPGRAFYATGAIIGDIREAHCNISTEQWNNTIFQIVDKLREQFG--NKTIIFNQSSGGD
AY835441_WB    -GPGRVFY-TGEIVGDIRQVHCNLSSARWNSTLKQVVTELREQFG--NKTIVFNQSSGGD
AY835439_NB    -GPGRAFYATGDIIGDIRQAHCNLSSVQWNDTLKQIVIKLGEQFGT-NKTIAFNQSSGGD
JRCSF_WB       -GPGRAFYTTGEIIGDIRQAHCNISRAQWNNTLKQIVEKLREQFNN--KTIVFTHSSGGD
JRFL_NB        -GPGRAFYTTGEIIGDIRQAHCNISRAKWNDTLKQIVIKLREQFEN--KTIVFNHSSGGD
Bal_WB         -GPGRAFYTTGEIIGDIRQAHCNLSRAKWNDTLNKIVIKLREQFGN--KTIVFKASSGGD
RXEC2_WB       NGPGRAFVTIGK-IGNMRQAHCNISPAKWNTLKQIASKLREQFGN--NKTIVFKQSSGGD
SF162_NB       -GPGRAFYATGDIIGDIRQAHCNISGEKWNNTLKQIVTKLQAQFGN--KTIVFKQSSGGD
AY835446_WB    -GPGRAFYTTGDIIGDIRQAHCNLSRQWNNNTLKQIAEKLREQFGN--KTIVFRNSSGGD
AY835448_NB    -GPGGAFFATGRIIGDIRKAYCTVNGTEWNTTLRQIVEKFKKQFGE-NKTIVFKPSAGGD
AY835452_GB    -GPGRAFYATGRIIGDIRKAHCNISGEKWENALEQIVKKLGEKFEN-ATTIRFNQSSGGD
AY835444_WB    -GPGRAFYATGDIIGDIRQAHCNLSRAEWNKTLKYISTELREQFGN--TTIIFNGSSGGD
                .**  :        *.:*:. * :.   *    *    :  .:      *  *   ***
```

FIG. 2G

```
EF117267_GB   LEITTHSFNCRGEFFYCNTSGLFNGTYMPTYM---------PNSTNSNSSSNITIPCRIKQV
EF117271_GB   LEITTHSFNCRGEFFYCNTSGLFNGTFNGTYVS--------PNSTDSNSSSIITIPCRIKQI
EF117273_GB   LEITTHSFNCRGEFFYCNTSKLFNSTYIPTYR---------PNNTQGNSSSTITIPCRIKQI
EF117265_NB   LEITTHSFNCRGEFFYCNTSSLFKGTYRPNGT---------SNSTSG---SIITLPCYIKQV
EF117268_GB   LEITTHSFNCRGEFFYCNTSSLFNSTYNPNDTN--------SNSSSSNSSLDITIPCRIKQI
EF117266_NB   LEITTHSFNCRGEFFYCNTSGLFNSTYMPNGTY--------MPNGTRNSNSTIITLPCRIKQI
EF117270_NB   LEITTHSFNCRGEFFYCNTSKLFNGIYNGTQS----------NSSNSNSTIIIPCRIKQI
EF117269_NB   LEITTHSFNCGGEFFYCNTSSLFNSTFNGTYM---------TNDTDMSNSTISIPCRIKQI
EF117274_NB   LEITTHSFNCRGEFFYCNTSDLFNGIYNGTYI---------PKG---NLNSTITIQCKIKQF
AY423984_NB   LEITTHSFNCGGEFFYCNTSSLFNGTYN-------------DTDIYNSTDIILLCRIKQI
EF117272_NB   LEITTHSFNCGGEFFYCNTSGLFNGTYMNNDTK--------SNDTKSNSSSIITIPCRIKQI
DQ411854_NB   LEVTTHSFNCRGEFFYCDTTKLFNSTKLFNSSE---------YVDNKTIILPCRIKQI
DQ435682_NB   LEVTTHSFNCGGEFFYCNT--------TPLFKWSS------NVTRDPIFIPCRIFQF
DQ388514_NB   LEITTHSFNCRGEFFYCTTSKLFNSTYNPNDTK--------S---NSNSNETLTLPCRIKQI
DQ388516_NB   LEITTHSFNCGGEFFYCNTTNLFSRTYTNGSNS---------NVNITSATITLPCRIKQI
DQ388517_NB   LEITTHSFNCGGEFFYCNTSGLFNSAIN-------------GFLTSNVTLPCRIKQI
DQ435683_NB   LEITTHSFNCGGEFFYCNFTKLFNSTANSTDSTVNSTDSTAKTGNSTNTNITLPCRIKQI
DQ411853_NB   LEITTHSFNCRGEFFYCYTSDLFNSTYMSN-----------NTGGANITLQCRIKQI
DQ388515_NB   LEITTHSFNCRGEFFYCNTSGLFNSSLLNDTDG--------TSNSTSNATITLPCRIKQI
AY424079_NB   LEITTHTFNCRGEFFYCNTSILF------------------TENENSSDNITLPCRIKQF
AY424138_GB   LEVTTHSFNCRGEFFYCNTSELFNS----------------NATESNITLPCRIKQI
AY835438_GB   PEIVMHSFNCAGEFFYCDTSQLFN-STWNSNST--------WNDTNNNNSTE--KIILGCRIRQI
AY835450_NB   PEVMKSFNCGGEFFYCNTSELFN-GTWNSTER---------ANNETG-------IIILQCRIKQI
AY835449_NB   PEVTMKSFNCGGEFFYCNTAQLFN-SSWDTNTN--------GNDTQGFGRNN-TIILPCRIKQI
AY835445_NB   PEITMHSFNCGGEFFYCNTTKLFN-STWKGN-N--------TTESDSTGEN----ITLPCRIKQI
AY835447_NB   PEIVMHSFNCNGEFFYCNTTELFT-STWNSTWN--------STWNNTEGSNSTVITLPCRIPQI
AY835451_NB   PEIVMRTFNCGGEFFYCNSTQLFN-STWFNNGT--------STWN-STADN-----ITLPCRIKQV
AY835441_NB   PEIVMHSFNCGGEFFYCNTTQLFN-STWRINGT--------WNGT--TVSN-KTIILPCRIKQI
AY835439_NB   PEIVMHSFNCGGEFFYCNTTQLFN-STWEFHGN----WTRSNFTESNSTTITLPCRIKQI
JRCSF_NB      PEIVMHSFNCGGEFFYCNSTQLFN-STWN------------DTRKSSGTRGNDTIILLPCRIKQI
JRFL_NB       PEIVMHSFNCGGEFFYCNSTQLFN-STWNN-------NTEGSNNTEGN-TITLPCRIKQI
Bal_NB        PEIVTHSFNCGGEFFYCNSTQLFN-STWN------------VTKESNNTVENNTITLPCRIKQI
SXBC2_NB      PEIVTHSFNCGGEFFYCNSTQLFN-STWFNSTN--------STEGSNNTEGSDTITLPCRIKQI
SF162_NB      PEIVMHSFNCGGEFFYCNSTQLFN-STWN--------NTIGPNNTNGT--ITLPCRIKQI
AY835446_NB   PEIVMNTFNCAGEFFYCNTAELFN-STWYANGT--------ISIGGGNKTN----IILPCRIKQF
AY835448_NB   PEIVTHSFNCGGEFFYCNTTNLFNSSSTELNST----WSGNSNDTGKNDTITLPCRIKQI
AY835452_GB   QEIVMHTFNCGGEFFYCNSTQLFN-STWPNGT----TTEWSNETSNG-TITLPCRIKQI
AY835444_NB   PEIVTHSFNCGGEFFYCNTTKLFN-STWDANGN--------CTGCDESDGNN-TITLPCRIKQI
              *:. *:*** ****:* :                        : : * *:*.
```

FIG. 2H

```
EF117267_GB    INMWQEVGRAMYAPPIEGEITCKSNITGLLLVRDGGNGNDTN-------KTEIFRPEGGD
EF117271_GB    INMWQEVGRAMYAPPIAGNITCKSNITGLLLVRDGGTGSESN-------KTEIFRPGGGD
EF117273_GB    INMWQEVGRAMYAPPIAGNITCKSNITGLLLVRDGGTGLNS--------STETFRPGGGD
EF117265_NB    INLWQEVGRAIYAPPIEGNITCISNITGLLLVRDGGNHEEAN-------TTETFRPGGGN
EF117268_GB    INMWQEVGRAMYAPPIEGNITCKSNITGLLLVRDG--GVESN-------ETEIFRPGGGD
EF117266_NB    INMWQEVGRAMYAPPIAGNITCNSNITGLLLVRDG---GK-NN------NTEIFPPGGGD
EF117270_NB    VNMWQKVGRAMYAPPIAGNITCTSNITGLLLVRDGG---PDN-------VTEIFRPGGGD
EF117269_NB    INMWQEVGRAMYAPPIAGNITCKSNITGLLLVRDGGNSNDTN-------EPEIFRPQGGD
EF117274_NB    INMWQEVGRAMYAPPIQGNITCESNITGLLLVRDGGNSNST--------EEIFRPGGGD
AY423984_NB    INMWQEVGRAMYAPPIEGNITCSSNITGLLLTRDGGLTNESK-------ETFRPGGGD
EF117272_NB    INMWQEVGRAVYAPPIAGNITCKSNITGILLTRDGGRGEEVKN------DTETFRPGGGN
DQ411854_NB    INMWQEVGRAMYAPPIEGNITCKSNITGLLLFWDGG----ENS------TEGVFRPGGGN
DQ435682_NB    INMWQGAGRAMYAPPIEGNITCNSSITGLLLTRDGG--TDRN-------DTEIFRPGGGN
DQ388514_NB    INMWQEVGRAMYAPPIEGSITCNSTITGLLLTRDGG----SKRN-----TEEIFRPGGGN
DQ388516_NB    INMWQEVGRAMYAPPIAGNITCISNITGLLLTRDGGNGNDTN-------DTETFRPAGGD
DQ388517_NB    INMWQEVGRAMYAPPIAGNITCKSNITGLLLTPDGGENSS--S------TTETFRPTGGD
DQ435683_NB    INMWQEVGRAMYAPPSKGNITCISNITGLLLTRDGKENKFERN------DTEIFRPGGGD
DQ411853_NB    INMWQGVGQAMYAPPIAGNITCKSSITGLLLTRDGGKERN---------DTETFRPGGGD
DQ388515_NB    INMWQEVGRAMYASPIAGIITCKSNITGLLLTPDGG--NKSA-------GIETFRPGGGN
AY424079_NB    VNMWQEVGRAMYAPPIAGNITCNSSITGLLLTRDGGLNNKEN-------GTETFRPQGGD
AY424138_GB    INMWQGVGRAMYAPPIRGEIKCTSNITGLLLTRDGGNNNNST-------EEIFRPEGGN
AY835438_GB    INRWQEVGKAMYAPPISGPIKCSSNITGLLLARDGGN--------ETN-VTETFRPAGGD
AY835450_NB    INMWQEVGKAMYAPPIEGQIRCSSNITGLLLTRDGGN----------TKNTTEFFRPGGGN
AY835449_NB    INMWQRVGKAIYAPPISGQIRCLSNITGLILTRDGGN-----------SSLSSPEIFRPGGGN
AY835445_NB    INLWQEVGKAMYAPPIEGQISCSSNITGLLLTRDGGNN----------NSSGPETFRPGGGN
AY835447_NB    INMWQEVGKAMYAPPIQSGIRCSSNITGLLLTRDGGVD----------TTK---ETFRPGGGN
AY835451_NB    INMWQEVGKAMYAPPIRGQIDCSSNITGLLLTRDGGSN----------SSQN-ETFRPGGGN
AY835441_NB    INMWQEVGKAMYAPPIRGQIRCSSNITGLLLFRDGGN-----------NNSTTEIFRPGGGD
AY835439_NB    VNMWQEVGKAMYAPPIRGQIRCSSNITGLLLTRDGGV---------NG-TRETFRPGGGD
JRCSF_NB       INMWQEVGKAMYAPPIRGQIRCSSNITGLLLTRDGGK-----------NESEIEIFRPGGGD
JRFL_NB        INMWQEVGKAMYAPPIRGQIRCSSNITGLLLTRDGGI---------NENGTEIFRPGGGD
Bal_NB         INMWQEVGKAMYAPPIPGQIRCSSNITGLLLTPDGGP-----------EDNKTEVFRPGGGD
SXEC2_NB       INMWQEVGKAMYAPPISGQIRCSSNITGLLLTRDGGN-----------SNNESEIFRPGGGN
SF162_NB       INRWQEVGKAMYAPPIRGQIRCSSNITGLLLTRDGGKE--------ISNTTEIFRPGGGD
AY835446_NB    INMWQEVGKAMYAPPISGQIRCSSNITGLLLTPDGGRGN---------QTDNQTEIFPPVGGD
AY835448_NB    INMWQQVGKAMYAPPISGKINCLSNITGLLLTRDGGSDGGSKNSSKNETGTEIFRPGGGD
AY835452_GB    INMWQEVGKAMYAPPISGPISCSSNITGLLLVRDGGND---------NETNGTETFRPGGGD
AY835444_NB    VNMWQEVGKAMYAPPIKGLIKCTSNITGLLLTPDGGRAN--------NTNETFRPGGGD
               :. **  .*:*:**.*  * * * * ***::**. **           *** **:
```

FIG. 21

```
EF117267_GB      MRDNWRSELYKYKVVEIKPLGIAPT-------------
EF117271_GB      MRDNWRSELYKYKVVEIKPLGVAPT-------------
EF117273_GB      MRDNWRSELYKYKVVEIKPLGVAPTAAKRRVVQREKR
EF117265_NB      MRDNWRSELYKYKVVEIKPLGVAPT-------------
EF117268_GB      MRDNWRSELYKYKVVEIKPLGIAPT-------------
EF117266_WB      MRDNWRSELYKYKVVEIKPLGVAPT-------------
EF117270_NB      MRDNWRSELYKYKVVEIKPLGIAPT-------------
EF117269_WB      MRDNWRSELYKYKVVEIKPLGVAPTAAKRRVVGREKR
EF117274_NB      MRDNWRSELYKYKVVEIKPLGVAPTDAKRRVVERGKR
AY423984_WB      MKDNWRSELYKYKVVEIKPLGIAPT-------------
EF117272_NB      MKDNWRSELYKYKVVEIKPLGVAPT-------------
DQ411854_WB      MRDNWRSELYKYKVVEIKPLGVAPTKSKRKVVGPREKR
DQ435682_WB      MKDNWRSELYKYKVVEIKPLGVAPT-------------
DQ388514_WB      MKDNWRSELYKYKVVEIKPLGVAPT-------------
DQ388516_NB      MRDNWRSELYKYKVVEIKPLGIAPTKAKRRVVGREKR
DQ388517_WB      MKNNWRSELYKYKVVEIKPLGIAPT-------------
DQ435683_WB      MKDNWRSELYKYKVVEIKPLGVAPT-------------
DQ411853_WB      MRDNWRSELYKYKVVEIKPLGIAP-------------
DQ388515_WB      MKDNWRSELYKYKVVEIKPLGIAPTAAKRRVVEREKR
AY424079_NB      MRDNWRSELYKYKVVEIRPLGVAPT-------------
AY424138_GB      MRDNWRSELYKYKVVEIKPLGIAPTEAKRRVVQREKR
AY835438_GB      MRDNWRSELYKYKVVQIEPLGIAPTKAKRRVVQREKR
AY835450_WB      MKDNWRSELYKYKVVPIKPLGVAPTKAKRRVVQREKR
AY835449_WB      MRDNWRSELYKYKVVQIEPLGIAPTKAKRPAVQREKR
AY835445_WB      MKDNWRSELYKYEVIKIEPLGVAPTRAKPRVVQPEKR
AY835447_WB      MKDNWRSELYKYKVVPIEPLGVAPTKAKRRVVQREKR
AY835451_WB      MKDNWRSELYKYKVVKIEPLGIAPTEAKRPVVQREKR
AY835441_WB      MPDNWRSELYKYKVVKIEPLGIAPTKAPPRVVQPEKR
AY835439_NB      MRDNWRSELYKYKVVKIEPLGVAPTKAKRRVVQREKR
JKCSF_WB         MRDNWRSELYKYKVVKIEPLGVAPTKAKRPVVQREKR
JRFL_NB          MRDNWRSELYKYKVVKIEPLGVAPTKAKRRVVQREKR
Bal_WB           MKDNWRSELYKYKVVKIEPLGVAPTKAKRRVVQREKR
SXBC2_WB         MKDNWRSELYKYKVVKIEPLGVAPTKAKRRVVQREKR
SF162_NB         MRDNWRSELYKYKVVKIEPLGVAPTKAKRRVVQREKR
AY835446_WB      MKNNWRSELYKYKVVRIEPLGIAPTRAKRRVVQREKR
AY835448_NB      MRDNWRSELYKYKVVRIEPLGVAPTKAKRRAVQREKR
AY835452_GB      MRDNWRSELYKYKVVKIEPLGVAPTKAKRPVVQREKR
AY835444_WB      MRDNWRSELYKYKVVQIEPLGI-------------
                 *:: ***.*******:.*.***:
```

Legend:

Accession#_GB represents Good Binders
Accession#_WB represents Weak/Moderate Binders
Accession#_NB represents Non Binders A, B – BG505 gp120 L111A from 293S cells;
C, D – BG505 gp120 L111A from 293T cells

FIG. 6

| BG505 L111A gp120 purified on GNL column | OD$_{450}$ | BG505 L111A gp120 purified on HisTrap column | OD$_{450}$ |
| --- | --- | --- | --- |
| b12 | 3.764 | b12 | 3.7285 |
| b6 | 3.801 | b6 | 3.766 |
| pg9 | 3.839 | pg9 | 3.7985 |
| pg16 | 3.7785 | pg16 | 3.733 |
| VCR01 | 3.8155 | VCR01 | 3.7935 |
| PGV04 | 3.7965 | PGV04 | 3.7885 |

FIG. 7

| Antibodies (2 mg/ml) | | BG505 L111A gp120 (purified from 293S sups) binding, OD450 | BG505 L111A gp120 (purified from 293T sups) binding, OD450 |
|---|---|---|---|
| Quaternary-structure-specific antibodies | pg9 | 3.74 | 3.73 |
| | pg16 | 3.72 | 3.70 |
| CD4 – binding site antibodies | b12 | 3.69 | 3.69 |
| | b6 | 3.72 | 3.75 |
| | VRC01 | 3.76 | 3.74 |
| | VRCPG04 (PGV04) | 3.74 | 3.75 |
| Sialic acid – dependent PGT antibodies | PGT121 | 1.67 | 3.74 |
| | PGT122 | 0.06 | 3.72 |
| | PGT123 | 0.23 | 3.61 |
| Sialic acid – independent PGT antibodies | PGT125 | 3.76 | 3.74 |
| | PGT126 | 3.76 | 3.75 |
| | PGT130 | 3.61 | 3.56 |

- BG505 L111A gp140 with GCN4 trimerization motif and Linker 4
- A – expressed in 293S and B – 293T cells
- ELISA of supernatants Log Antibody concentration (μg/ml)

- A – gp140 supernatants from 293S cells; B – gp140 sups from 293T cells
- PGV04 included as a control
- Pgt121, 122, and 123 binding depends on sialilation of oligosaccharides
- Pgt135 shows weak binding
- Pgt136 and 141 do not bind

FIG. 10

|  | PG9 | PG16 | b12 | VRC01 | PGV04 | 2F5 | 4E10 |
|---|---|---|---|---|---|---|---|
| BG505 wt | 0.11 | ‹ 0.01 | › 25 | 0.06 | 0.05 | 0.46 | 0.89 |
| BG505 L111A | 0.02 | ‹ 0.01 | › 25 | ‹ 0.01 | ‹ 0.01 | 0.34 | 2 |

|  | PGT 121 | PGT122 | PGT123 | PGT125 | PGT126 | PGT130 | PGT135 |
|---|---|---|---|---|---|---|---|
| BG505 wt | 0.06 | 0.09 | 5.37 | ‹ 0.01 | 0.26 | 0.06 | 18.16 |
| BG505 L111A | ‹ 0.01 | ‹ 0.01 | 0.65 | ‹ 0.01 | ‹ 0.01 | 4.99 | › 25 |

- Neutralization assay uses HIV pseudovirus to test antibodies that prevent virus cell entry.
- Only fully functional gp160 spikes on the virus surface are recognized and neutralized by human bnAbs
- The extent of neutralization is presented as IC50 value (μg of antibody per ml)
- Neutralization assay shows that cleaved BG505 gp160 is functional and recognized and neutralized by pg9/16 and most other neutralizing anti-gp120 antibodies
- It is also neutralized by 2F5 and 4E10 (anti-gp41)
- b12, 2G12 and PGT136/136 do not neutralize BG505 pseudovirus
- The pattern of BG505 L111A pseudovirus is very similar to the wild type virus

FIG. 13

| Antibodies (2 mg/ml) | | BG505 L111A gp120 (from 293S sups) binding, OD450 | BG505 L111A T332N gp120 (from 293S sups) binding, OD450 | BG505 L111A gp120 (from 293T sups) binding, OD450 | BG505 L111A T332N gp120 (from 293T sups) binding, OD450 |
|---|---|---|---|---|---|
| Quaternary-structure-specific antibodies | pg9 | 3.74 | 3.55 | 3.73 | 3.50 |
| | pg16 | 3.72 | 3.50 | 3.70 | 2.86 |
| CD4 – binding site antibodies | b12 | 3.69 | 3.49 | 3.69 | 3.53 |
| | b6 | 3.72 | 3.48 | 3.75 | 3.48 |
| | VRC01 | 3.76 | N/A | 3.74 | N/A |
| | VRCPG04 (PGV04) | 3.74 | 3.54 | 3.75 | 3.50 |
| Carbohydrate-dependent PGT antibodies | PGT121 | 1.67 | 3.53 | 3.74 | 3.55 |
| | PGT122 | 0.06 | N/A | 3.72 | N/A |
| | PGT123 | 0.23 | N/A | 3.61 | N/A |
| | PGT125 | 3.76 | 3.53 | 3.74 | 3.55 |
| | PGT126 | 3.76 | 3.52 | 3.75 | 3.55 |
| | PGT130 | 3.61 | N/A | 3.56 | N/A |
| | PGT135 | 0.00 | 3.54 | 0.00 | 3.53 |
| | PGT136 | 0.00 | 3.53 | 0.00 | 3.51 |

METHODS FOR IDENTIFYING BROADLY NEUTRALIZING ANTIBODIES UTILIZING RECOMBINANT HIV-1 ENVELOPE GLYCOPROTEINS COMPRISING STABILIZING MUTATIONS

RELATED APPLICATIONS AND INCORPORATION BY REFERENCE

This application is a claims priority to U.S. provisional patent application Ser. No. 61/664,990 filed Jun. 27, 2012. Reference is made to international patent application Serial No. PCT/US11/26862 filed Mar. 2, 2011 which published as international patent publication WO 2011/109511 on Sep. 9, 2011 and claims priority to U.S. provisional patent application Ser. No. 61/309,685 filed Mar. 2, 2010.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted in ASCII format via EFS-Web and is hereby incorporated by reference in its entirety. Said ASCII copy, created on Sep. 24, 2013, is named 43094.01.2023_SL.txt and is 155,381 bytes in size.

FIELD OF THE INVENTION

This application relates to a novel HIV-1 envelope glycoprotein which may be utilized as an HIV-1 vaccine immunogen, as native Env trimer mimic, identification of small molecules for use as immunogen that bind specific HIV-1 broad neutralizing antibodies, identification of small molecules for use as anti-viral compound that bind specific HIV-1 envelope glycoprotein monomer and/or trimer, antigens for crystallization and for the identification of broad neutralizing antibodies.

BACKGROUND OF THE INVENTION

AIDS, or Acquired Immunodeficiency Syndrome, is caused by human immunodeficiency virus (HIV) and is characterized by several clinical features including wasting syndromes, central nervous system degeneration and profound immunosuppression that results in opportunistic infections and malignancies. HIV is a member of the lentivirus family of animal retroviruses, which include the visna virus of sheep and the bovine, feline, and simian immunodeficiency viruses (SIV). Two closely related types of HIV, designated HIV-1 and HIV-2, have been identified thus far, of which HIV-1 is by far the most common cause of AIDS. However, HIV-2, which differs in genomic structure and antigenicity, causes a similar clinical syndrome.

An infectious HIV particle consists of two identical strands of RNA, each approximately 9.2 kb long, packaged within a core of viral proteins. This core structure is surrounded by a phospholipid bilayer envelope derived from the host cell membrane that also includes virally-encoded membrane proteins (Abbas et al., Cellular and Molecular Immunology, 4th edition, W.B. Saunders Company, 2000, p. 454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural proteins. The gag gene encodes structural proteins of the nucleocapsid core and matrix. The pol gene encodes reverse transcriptase (RT), integrase (IN), and viral protease (PR) enzymes required for viral replication. The tat gene encodes a protein that is required for elongation of viral transcripts. The rev gene encodes a protein that promotes the nuclear export of incompletely spliced or unspliced viral RNAs. The vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The env gene encodes the viral envelope glycoprotein that is translated as a 160-kilodalton (kDa) precursor (gp160) and cleaved by a cellular protease to yield the external 120-kDa envelope glycoprotein (gp120) and the transmembrane 41-kDa envelope glycoprotein (gp41), which are required for the infection of cells (Abbas et al., Cellular and Molecular Immunology, 4th edition, W.B. Saunders Company, 2000, pp. 454-456). gp140 is a modified form of the Env glycoprotein, which contains the external 120-kDa envelope glycoprotein portion and the extracellular part of the gp41 portion of Env and has characteristics of both gp120 and gp41. The nef gene is conserved among primate lentiviruses and is one of the first viral genes that is transcribed following infection. In vitro, several functions have been described, including down-regulation of CD4 and MHC class I surface expression, altered T-cell signaling and activation, and enhanced viral infectivity.

HIV infection initiates with gp120 on the viral particle binding to the CD4 and chemokine receptor molecules (e.g., CXCR4, CCR5) on the cell membrane of target cells such as $CD4^+$ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp120 expressed on the surface of infected cells. In this case, the uninfected cells bind, via the CD4 receptor-gp120 interaction, to infected cells and fuse to form a syncytium, which cannot survive. Destruction of $CD4^+$ T-lymphocytes, which are critical to immune defense, is a major cause of the progressive immune dysfunction that is the hallmark of AIDS disease progression. The loss of $CD4^+$ T cells seriously impairs the body's ability to fight most invaders, but it has a particularly severe impact on the defenses against viruses, fungi, parasites and certain bacteria, including mycobacteria.

Research on the Env glycoprotein has shown that the virus has many effective protective mechanisms with few vulnerabilities (Wyatt & Sodroski, Science. 1998 Jun. 19; 280(5371):1884-8). For fusion with its target cells, HIV-1 uses a trimeric Env complex containing gp120 and gp41 subunits (Burton et al., Nat Immunol. 2004 March; 5(3): 233-6). The fusion potential of the Env complex is triggered by engagement of the CD4 receptor and a coreceptor, usually CCR5 or CXCR4. Neutralizing antibodies seem to work either by binding to the mature trimer on the virion surface and preventing initial receptor engagement events, or by binding after virion attachment and inhibiting the fusion process (Parren & Burton, Adv Immunol. 2001; 77:195-262). In the latter case, neutralizing antibodies may bind to epitopes whose exposure is enhanced or triggered by receptor binding. However, given the potential antiviral effects of neutralizing antibodies, it is not unexpected that HIV-1 has evolved multiple mechanisms to protect it from antibody binding (Johnson & Desrosiers, Annu Rev Med. 2002; 53:499-518).

Most experimental HIV-1 vaccines tested in human and/or non-human primate suggests that a successful vaccine will incorporate immunogens that elicit broad neutralizing antibodies (bNabs) and robust cell-mediated immunity. HIV-1 envelope glycoprotein (Env) is the main viral protein involved in the entry of the virus and is also the primary target for neutralizing antibodies, but due to immune evasion strategies and extreme sequence variability of Envs, generation of bNabs has been daunting task (Phogat S, Wyatt R. Curr Pharm Des. 2007; 13:213-27, Phogat S, et al. J Intern Med. 2007 262:26-43, Karlsson Hedestam G B, et al Nat Rev Microbiol. 2008 6:143-55).

The ability to elicit broad and potent neutralizing antibodies is a major challenge in the development of an HIV-1 vaccine. Namely, HIV-1 has evolved an impressive array of strategies to evade antibody-mediated neutralization, bNAbs develop over time in a proportion of HIV-1 infected individuals, and a handful of broad neutralizing monoclonal antibodies have been isolated from clade B infected donors. These antibodies tend to display less breadth and potency against non-clade B viruses, and they recognize epitopes on the virus that so far have failed to elicit broad neutralizing responses when incorporated into a diverse range of immunogens. Presumably, due to the ability of these bNabs to recognize conserved recessed targets on HIV Env which are either inaccessible by elicited antibodies or difficult to precisely redesign and present to the immune system.

Recently using a sensitive high-throughput micro-neutralization screening of supernatants from approximately 30,000 IgG+ memory B cells from a HIV-1 clade A-infected African donor, Applicants identified two new bNabs PG9 and PG16 that are broad and exceptionally potent neutralizing antibodies (Walker L, Phogat S, et al. Science. 2009; 326:285-9. Epub 2009 Sep. 3). These antibodies recognize a new conserved, yet accessible, vaccine target (consisting of conserved elements on the variable loops 2 and 3) on the Env and show preferential binding to HIV Env trimer (Model of PG9 and 16 epitopes on HIV-1 trimer.). When tested for binding, these antibodies did not show binding to many empirically designed soluble (Env gp140) HIV Env trimer thought to be mimics of the native HIV-1 Env spike, suggesting that either these Env designs are either incorrect or they are fixed in a form not recognized by PG9 and PG16.

Citation or identification of any document in this application is not an admission that such document is available as prior art to the present invention.

SUMMARY OF THE INVENTION

Based on the binding property and breadth/potency of the new antibodies to neutralize >75% of the viruses tested, Applicants hypothesize that PG9, PG16 and certain CD4-binding site antibodies recognize a relevant vaccine target on the native HIV-1 Env on the surface of the virus and identification of HIV-1 envelope glycoproteins that present these targets on soluble forms of HIV-1 envelope would be good HIV-1 vaccine candidates to elicit PG9 and PG16 like antibodies and also can be used as reagents for mapping and crystallization studies.

The envelope glycoproteins identified as a part of this invention shows significantly better binding to new identified broad neutralizing antibodies PG9 and/or PG16. These are the only soluble forms of envelope identified that show such remarkable binding to PG9 and PG16. The envelope glycoproteins Envs have value (a) as reagents for screening of broad neutralizing antibodies, such as but not limited to, PG9 and PG16, (b) as reagents for screening of small molecules that compete binding of broad neutralizing antibodies, such as but not limited to, PG9 and PG16, (c) as monomer and native envelope trimer mimic for crystallization studies and (d) as immunogens in different forms to use as HIV-1 vaccine components, for example, to elicit broadly neutralizing antibodies.

In an advantageous embodiment, the soluble envelope glycoproteins of the present invention may be isolated from HIV-1 Clade A virus, HIV-1 Clade B virus, HIV-1 Clade C virus, a HIV-1 Clade A pseudo-virus, HIV-1 Clade B pseudo-virus or a HIV-1 Clade C pseudo-virus. In an advantageous embodiment, the soluble envelope glycoproteins of the present invention may be isolated from the 6535 virus, the 13095 virus, the 16055 virus, the 25710 virus, the 25925 virus, the CAAN virus or the Zm109F virus. Sequences of these viruses are available in the NCBI data base and Applicants have used them to generate recombinant Env proteins with unique sequences in which Applicants have modified the leader, added His-tag and terminated the sequence before the cleavage site for gp120 and before the transmembrane for gp140. The DNA sequences are unique as they are codon optimized based on mammalian codons for expression in mammalian cells.

In another advantageous embodiment, the soluble envelope glycoproteins have substantially similar sequences to the protein sequences depicted in FIGS. 2A-2J. In another particularly advantageous embodiment, the soluble envelope glycoprotein has a substantially similar consensus sequence to the consensus sequence depicted in FIGS. 2A-2J.

In a particularly advantageous embodiment, the soluble envelope glycoprotein may be isolated from a 16055 and/or BG505 virus and having a mutation L111A and/or T332N.

Another advantageous embodiment encompasses a stable soluble HIV-1 envelope glycoprotein trimer mimic.

A further embodiment involves the use of the identified Env monomer gp120 for selection of small molecules that bind to PG9 and antibodies that bind CD4 sites and can be used as immunogens.

Another embodiment encompasses the use of the identified Env monomer gp120 for selection of small molecules that bind to PG9 binding site or the binding site of antibodies that bind to CD4 sites on the monomer and inactivates the HIV-1 virus in a manner similar to the manner in which antibody PG9 and antibodies that bind CD4 sites do.

A further embodiment involves the use of the discovered Env trimer mimic gp140 for selection of small molecules that bind to PG9, PG16 antibodies and antibodies that bind to CD4 binding sites and can be used as immunogen.

In another advantageous embodiment, the identified Env trimer is used for selection of small molecules that bind to PG9, PG16 and CD4 binding sites on the HIV-1 virus Env trimer and inactivates the HIV-1 virus in a manner similar to the antibodies PG9, PG16 and antibodies that bind to CD4 binding sites.

A further embodiment involves the use of the monomer and trimer for mapping of PG9 and PG16 specificity in human and animal sera.

Another embodiment includes the identification of PG9 and PG16 like antibodies using the identified HIV-1 Env monomer and trimer.

A further embodiment involves the use of the HIV Env monomer and trimer for display on particulate antigens like Qbeta particle.

Another embodiment includes the use of the HIV-1 Env monomer and trimer in replicating and non-replicating vectors as DNA for priming.

Yet another embodiment encompasses a method for identifying novel HIV envelope proteins binding to broad neutralizing antibodies (such as PG9 and PG16 antibodies) by using a combination of bioinformatics approach based on patients Envelope sequences and binding assay of the homologous proteins. The evolutionary proximity of these proteins to the patients' Envelope proteins may improve generation of broadly neutralizing antibodies administered alone or in combination with other PG9 and PG16 binding proteins. The present invention also encompasses proteins identified by this method, such as, for example, gp120 BG505 clade A (see, e.g., GenBank Accession Nos. ABA61516 and DQ208458 and Wu et al., J. Virol. 80 (2), 835-844 (2006) and Erratum: [J. Virol. 2006 March; 80(5): 2585).

The present invention also encompasses an isolated or non-naturally occurring V1-3 loop which may comprise a conformation of an amino acid sequence of a PG9 binding protein. The isolated or non-naturally occurring V1-3 loop may comprise the amino acid sequences of V1-16055, V2-16055 or V3-16055. An isolated or non-naturally occurring soluble HIV-1 envelope glycoprotein having the V1-3 loop of claim 15.

The present invention also encompasses an isolated or non-naturally occurring soluble HIV-1 envelope glycoprotein which may comprise the amino acid sequences of V1-16055, V2-16055 or V3-16055. In an advantageous embodiment, the glycoprotein may be a chimeric protein.

The invention also relates to a method for neutralizing tier 1 and tier 2 HIV-1 viruses in patient in need thereof which may comprise administering to the patient a priming dose of a vector containing and expressing gp120 isolated from a 16055 virus and further administering to the patient a protein boost a gp120 protein isolated from a 16055 virus, wherein the sera from the patient neutralizes tier 1 and tier 2 clade B and clade C HIV-1 viruses in the patient. The method may further comprise isolating the sera from the patient and testing the sera in a pseudoneutralization assay to determine if the sera is indeed neutralizing. The HIV-1 virus may be a HIV-1 Clade A virus, HIV-1 Clade B virus, HIV-1 Clade C virus, a HIV-1 Clade A pseudo-virus, HIV-1 Clade B pseudo-virus or a HIV-1 Clade C pseudo-virus.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 depicts recombinant HIV-1 envelope glycoprotein gp120 BG505 clade A ELISA binding and phylogeny tree. ELISA showed significant binding of PG9, PG16 and b12 antibodies to BG505 gp120. The BG505 protein sequence was selected using bioinformatics approach that identified close progenitor sequence to HIV-1 clade A Env from Env protein database. The HIV-1 Env clade A sequences from the donor (V1_011) who gave rise to PG9 and PG16 antibodies were used to search the HIV-1 Env protein data base.

FIGS. 2A-2J depict the alignment of HIV-1 ENV protein gp120 sequences (SEQ ID NOS 1-38, respectively, in order of appearance) of good (red letters), moderate (green) and non (black)—PG9 binder and subjected to web logo analysis. Residues important for PG9 and PG16 binding are boxed in vertical columns located in the variable loops V1/V2 stem, V2 and V3 loop. Residues (HxBC2 numbering) at positions 156, 158, 159, 160, 162 in V1/V2 stem, 168, 176, 181 in V2 and 299, 305, 307, 309, 317, 318 in V3 loop are highly conserved and are found in all Envs irrespective of their neutralization or binding by PG antibodies. FIG. 2J depicts web logo analysis of the HIV-1 Env sequences in the variable loop 1, 2 and 3 aligned in FIGS. 2A-2I, the size of the residue represents conservation. All residues involved in PG9 and PG16 binding are denoted by "*".

FIG. 6 depicts an antigenicity profile by ELISA of BG505 L111A purified by 2 different chromatographic approaches. Subsequent binding of antibodies proved undistinguishable by ELISA.

FIG. 7 depicts antibody binding to the purified BG505 L111A gp120 protein. Proteins carrying L111A mutation were successfully purified both from 293S and 293T cells by GNL column and preserved their antigenicity which was confirmed by ELISA of purified proteins. With the exception of a few PGT antibodies most broadly neutralizing antibodies bind to BG505 L111A gp120. PGT135, 136 and 141 do not bind to BG505 gp120.

FIG. 10 depicts a neutralization assay (comparison of BG505 WT and BG505 L111A pseudoviruses). The neutralization assay was done with BG505 WT and L111A pseudoviruses and a panel of human broadly neutralizing antibodies. Most antibodies neutralize both forms of virus to the same extent. That is a clear indication that L111A mutation does not jeopardize fully functional gp160.

FIG. 11 depicts a Clade and Mutant Specific Binding Profiles by cytofluorimetry. Another test for the integrity of gp160 Envelope protein with L111A mutation was done with gp160 expressed in HEK 293T cells by transient transfection with a plasmid DNA. In this study binding of a panel of neutralizing antibodies was measured by using cytofluorimetry (FACS). BG505 had the broadest binding pattern compare to Clade B (JR-FL), and Clade C (16055). Binding pattern to BG505WT and L111A was similar.

FIG. 13 depicts Binding to BG505 L111A gp120. Binding of antibody to BG505 L111A gp120 secreted into cell culture media was measured by Enzyme-linked immunosorbent assay (ELISA) in 96-well microplates. The set of antibodies used to characterize antigenicity included trimer-specific antibodies (PG9, PG16), CD4 binding site (CD4bs) specific antibodies (b6, b12, VRC01, VRC04/PGV04), and PGT series (PGT121-136). Antibodies that demonstrated difference in binding properties are shown in red.

DETAILED DESCRIPTION

Figure 2J:
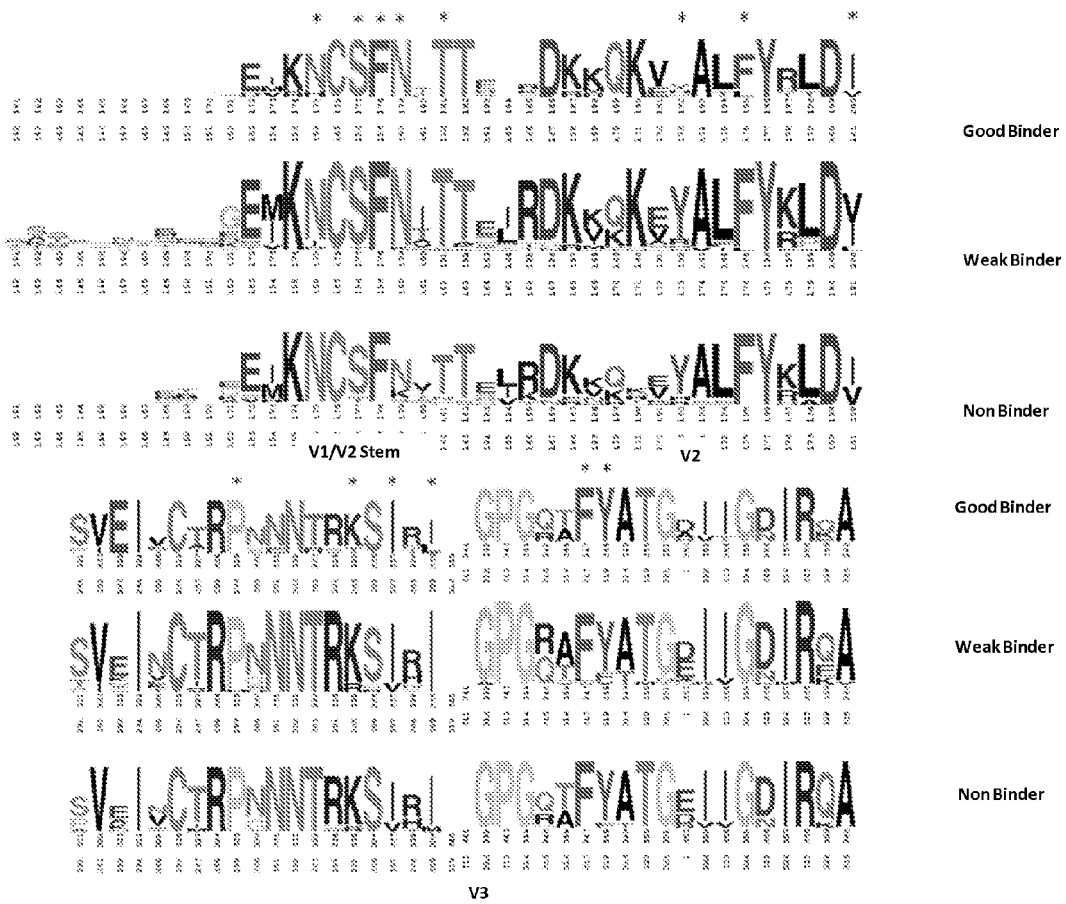

Broad neutralizing antibodies PG9 and PG16 were used for screening and selecting HIV-1 isolates from a panel consisting of sixty four viral isolates from HIV-1 clade-B and C for their ability to neutralize and to bind soluble form of HIV-1 Envelope glycoprotein. Applicants identified nine HIV-1 envelopes that were neutralized and showed binding by bNab PG9 and/or PG16. Two of the soluble HIV-1 Envs—DU422 (clade C) and YU2 (clade B) were already identified and reported (Walker L, Phogat S, et al. Science. 2009; 326:285-9. Epub 2009 Sep. 3). As a part of this invention, Applicants identified three new soluble HIV-1 Envs each from HIV-1 clade B and clade C viral isolates that show binding to bNab PG9. In addition, Applicants identified one soluble Env from HIV-1 clade C that showing binding to both bNab PG9 and PG16. The Envs identified as a part of this invention shows significantly better binding to bNabs PG9 and PG16 compared to DU422 and YU2 envelope. These newly identified Envs are the only soluble forms of Env identified till date that show such remarkable binding to PG9 and/or PG16. In addition to identification of soluble gp120 that shows significant binding to PG9, Applicants identified one native envelope trimer mimic gp140 molecules that shows significant binding to both PG9 and PG16.

These Envs may have the following utilities:

Reagents for screening of new broad neutralizing antibodies like PG9 and PG16, mapping of human sera with broad neutralizing serum activity and animal sera following immunization studies For screening of small molecules that competes binding of broad neutralizing antibodies, such as PG9 and PG16. The identified small molecule could be used as immunogen or anti-viral compounds Crystallization studies with Monomer bound PG9 and PG16 to determine the exact molecular surface where PG9 and PG16 bind to design novel HIV-1 immunogens Crystallization studies with trimer bound PG9 and PG16 and any other ligand to determine the exact structure of a native Env trimer Immunogens in different forms to use as HIV-1 vaccine components to elicit bNabs. The different forms of the HIV-1 envelope will be use in a prime, as DNA/vector expressing the protein/protein and as a boost as protein. The envelopes could also be used as particulate immunogen by cross linking to virus particles like Qbeta, cow pea mosaic virus, CRM, HPV, HBsAg etc.

In an advantageous embodiment, the soluble envelope glycoproteins of the present invention may be isolated from HIV-1 Clade A virus, HIV-1 Clade B virus, HIV-1 Clade C virus, a HIV-1 Clade A pseudo-virus, HIV-1 Clade B pseudo-virus or a HIV-1 Clade C pseudo-virus In an advantageous embodiment, the soluble envelope glycoproteins of the present invention may be isolated from the 6535 virus, the 13095 virus, the 16055 virus, the 25710 virus, the 25925 virus, the CAAN virus or the Zm109F virus. Applicants have generated recombinant Env proteins with unique sequences in which Applicants have modified the leader, added His-tag and terminated the sequence before the cleavage site for gp120 and before the transmembrane for gp140. The DNA sequences are unique as they are codon optimized.

In a particularly advantageous embodiment, the envelope glycoproteins of the present invention are isolated from the 16055 and/or BG505 viruses.

In another advantageous embodiment, the soluble envelope glycoproteins have substantially similar sequences to the protein sequences depicted in FIGS. 2A-2J. In another particularly advantageous embodiment, the soluble envelope glycoprotein has a substantially similar consensus sequence to the consensus sequence depicted in FIGS. 2A-2J.

In one embodiment, the soluble Env of the present invention may be used as reagents to screen for and identify new broadly neutralizing antibodies, such as PG9 and PG16. As used herein, a neutralizing antibody may inhibit the entry of HIV-1 virus with a neutralization index >1.5 or >2.0. Broad and potent neutralizing antibodies may neutralize greater than about 50% of HIV-1 viruses (from diverse clades and different strains within a clade) in a neutralization assay. The inhibitory concentration of the monoclonal antibody may be less than about 25 mg/ml to neutralize about 50% of the input virus in the neutralization assay.

Yet another embodiment encompasses a method for identifying novel HIV envelope proteins binding to PG9 and PG16 antibodies by using a combination of bioinformatics approach based on patients Envelope sequences and binding assay of the homologous proteins. The evolutionary proximity of these proteins to the patients' Envelope proteins may improve generation of broadly neutralizing antibodies administered alone or in combination with other PG9 and PG16 binding proteins. The present invention also encompasses proteins identified by this method, such as, for example, gp120 BG505 clade A.

Essentially the approach will be to generate HIV-1 Env sequence from donor who give rise to any (new or existing) broad neutralizing antibodies. Thus far in all cases Applicants have found that the Env sequence in donor sera escape neutralization by the broad neutralizing antibodies isolated from the donor. As a result the isolated sequence is not good for use as an immunogen. The new approach uses HIV-1 Env sequence isolated from the donor, the sequences are used to identify its close progenitor, sequence alignment is performed with all the Env sequences using programs like clustalW and then phylogenic tree is generated to determine Env sequences that are closely related and have least genetic distances. These closest homolog are then tested for binding to identify novel immunogen that bind broad neutralizing antibodies and are potential candidates to elicit neutralizing response.

In particular, such a method is exemplified in FIG. 1, which depicts a recombinant HIV-1 envelope glycoprotein gp120 BG505 clade A ELISA binding and phylogeny tree. ELISA showed significant binding of PG9, PG16 and b12 antibodies to BG505 gp120. The BG505 protein sequence was selected using bioinformatics approach that identified close progenitor sequence to HIV-1 clade A Env from Env protein database. The HIV-1 Env clade A sequences from the donor (V1_011) who gave rise to PG9 and PG16 antibodies were used to search the HIV-1 Env protein data base.

The present invention also encompasses an isolated or non-naturally occurring V1-3 loop which may comprise a conformation of an amino acid sequence of a PG9 binding protein. The isolated or non-naturally occurring V1-3 loop may comprise the amino acid sequences of V1-16055, V2-16055 or V3-16055. The V1-3 loop sequences of 16055 may be advantageous for conferring binding and/or neutralization activity. The present invention also encompasses an isolated or non-naturally occurring soluble HIV-1 envelope glycoprotein which may comprise the amino acid sequences of V1-16055, V2-16055 or V3-16055. In an advantageous embodiment, the glycoprotein may be a chimeric protein. Without being bound by theory, Applicants surmise that the conformation, and not necessarily the sequence, of the loop confers PG9, PG16 and possibly b12 binding.

The invention also relates to a method for neutralizing tier 1 and tier 2 HIV-1 viruses in patient in need thereof which may comprise administering to the patient a priming dose of a vector containing and expressing gp120 isolated from a 16055 virus and further administering to the patient a protein boost a gp120 protein isolated from a 16055 virus, wherein the sera from the patient neutralizes HIV-1 viruses in the patient. The HIV-1 virus may be HIV-1 Clade A virus, HIV-1 Clade B virus, HIV-1 Clade C virus, a HIV-1 Clade A pseudo-virus, HIV-1 Clade B pseudo-virus or a HIV-1 Clade C pseudo-virus, Advantageously, the HIV-1 viruses are tier 1 and tier 2 clade B and clade C HIV-1 viruses. The method may further comprise isolating the sera from the patient and testing the sera in a pseudoneutralization assay to determine if the sera is indeed neutralizing. Representative tier 1, tier 2 and tier 3 viruses are provided by Seaman et al., Journal of Virology, February 2010, Vol. 84, No. 3, pp. 1439-1452.

FIGS. 13A-13D depict a 16055 immunogenicity study in rabbits. (a) immunization schedule and dose is presented for six animals immunized by intra muscular route per group at weeks 0, 4, 12, 20 and 28. Sera were collected two weeks post immunization and week 0, 14 and 31 sera were analyzed for binding and neutralization activity. (b) represent anti-Env ELISA titer represented as geometric mean titers and (c) represents IC50 values for neutralization of tier I and tier II clade B and clade C HIV-1 viruses, JRCSF N160K and N156K. In group I and II, six rabbits were immunized with pCMVR-16055 gp120 DNA and pCMVR DNA respectively (250 ug/animal/immunization) at week 0, 4 and 12 by electroporation followed by two protein boost (50 ug/animal/immunization) at weeks 20 and 28. Six rabbits in group III were immunized with 16055 gp120 protein at week 0, 4, 12, 20 and 28. All bleeds were collected 2 weeks post immunization except at for the last bleed which was collected 3 weeks post immunization. In group I DNA priming elicited high titer anti-Env antibodies after 1st immunization (~1:5000) which saturated after 2nd DNA EP ($1:2\times10^4$) and did not increase after 3rd DNA EP. Following protein boost the anti-Env titer further increased (~$1:1\times10^5$). In group II no anti-Env antibodies were observed following control DNA EP at week but following protein boost the anti-Env titer of $1:1\times10^5$ was observed. In group III anti-Env titers saturated following three protein immunization. The sera were tested for pseudovirus neutralization assay based on Tzmb1 cells containing Tat controlled luciferase expression. The DNA EP-16055 gp120 protein generated sera showed neutralization of homologous 16055 virus for two out of six rabbits, the other groups did not neutralize 16055 virus. Heterologous tier I clade C MW965 virus was potently neutralized by sera generated at week 14 and 31 by all three group. Similarly potent cross clade-neutralization was observed for tier I clade B SF162 and SS1196 viruses. Heterologous tier II clade C IN905 and MGRM026 were potently neutralized by group I and III sera at week 31. IN905 virus was also neutralized by group I and III sera at week 14. Heterologous cross-clade tier II YU2 virus was resistant to all group sera but JRCSF virus was neutralized weakly by week 14 sera and the neut titers increased at week 31. JRCSF mutant N160K shown to be resistant to PG9 and PG16 anti bodies was resistant to all group sera whereas another mutant N156A was globally sensitive and behaved like a tier I virus. Over all anti-Env sera was elicited that showed cross clade neutralization of Tier I and II homologous and heterologous viruses.

Assays for screening for neutralizing antibodies are known in the art. A neutralization assay approach has been described previously (Binley J M, et al., (2004). Comprehensive Cross-Clade Neutralization Analysis of a Panel of Anti-Human Immunodeficiency Virus Type I Monoclonal Antibodies. *J. Virol.* 78: 13232-13252). Pseudotyped viruses may be generated by co-transfecting cells with at least two plasmids encoding the soluble Env cDNA of the present invention and the rest of the HIV genome separately. In the HIV genome encoding vector, the Env gene may be replaced by the firefly luciferase gene. Transfectant supernatants containing pseudotyped virus may be co-incubated overnight with B cell supernatants derived from activation of an infected donor's primary peripheral blood mononuclear cells (PBMCs). Cells stably transfected with and expressing CD4 plus the CCR5 and CXCR4 coreceptors may be added to the mixture and incubated for 3 days at 37° C. Infected cells may be quantified by luminometry.

The method of U.S. Pat. No. 7,386,232 may also be utilized for the screening of broad neutralizing antibodies. An envelope-enzyme fusion protein may be constructed by attaching an enzyme to the C-terminal end of an envelope protein. Virus particles comprising of the fusion protein and wild type and/or soluble envelope glycoprotein may be generated and used to infect target cells in the presence of a patients' sera. Activities of enzyme measured in such infected cells are measures of virus binding and entry to the target cells that are mediated by the wild type viral envelope protein. Examples of enzymes that can be used to generate the fusion protein include, but are not limited to, luciferase, bacterial or placental alkaline phosphatase, β-galactosidase, and fluorescent proteins such as Green fluorescent protein or toxins. The assay, in general, can also be carried out in 96-well plate. Decreased enzyme activities in the presence of the sera indicate that there are neutralizing antibodies in the sera.

In another embodiment of the present invention, the soluble envelope glycoproteins of the present invention may be crystallized in the combination with PG9 or PG16 or with any other neutralizing antibodies, including those identified by the above methods, to determine the exact molecular surface where the soluble envelope glycoprotein binds with the neutralizing antibody to design novel HIV-1 immunogens.

Crystals of the invention may be obtained by conventional means as are well-known in the art of protein crystallography, including batch, liquid bridge, dialysis, vapor diffusion and hanging drop methods (see, e.g., Johnson et al. Biochemistry. 1982 Sep. 28; 21(20):4839-43; Brayer & McPherson, J Biol. Chem. 1982 Apr. 10; 257(7):3359-61; McPherson & Weickmann, J Biomol Struct Dyn. 1990 April; 7(5):1053-60; and Koszelak et al., J Mol. Biol. 1989 Sep. 20; 209(2):323-5; Weber et al., Acta Crystallogr B. 1991 Feb. 1; 47 (Pt 1):116-27 and Weber, Methods Enzymol. 1991; 202:727-41).

Generally, the crystals of the invention are grown by dissolving a substantially pure neutralizing antibody, such as PG9 or PG16, and soluble envelope glycoprotein in an aqueous buffer containing a precipitant at a concentration just below that necessary to precipitate the protein. Water is removed by controlled evaporation to produce precipitating conditions, which are maintained until crystal growth ceases.

The crystals of the invention, and particularly the atomic structure co-ordinates obtained therefrom, have a wide variety of uses. The crystals and structure co-ordinates are particularly useful for identifying compounds that bind to a neutralizing antibody, such as PG9 or PG16, and thus are useful to elicit anti-HIV antibodies. Such compounds may be useful in eliciting clade B and C anti-HIV antibodies, however variants may be useful in eliciting clade A, D or E anti-HIV antibodies.

The structure co-ordinates may be used as phasing models in determining the crystal structures of a synthetic or mutated neutralizing antibody, such as PG9 or PG16, domains, as well as the structures of co-crystals of such domains with ligands.

The provision of the crystal structure of a neutralizing antibody, such as PG9 or PG16, complexed with a soluble envelope glycoprotein provide the skilled artisan with a detailed insight into the mechanisms of action of a neutralizing antibody, such as PG9 or PG16. This insight provides a means to design compounds that bind to a neutralizing antibody, such as PG9 or PG16, and thus to certain anti-HIV antibodies, and therefore compounds that elicit anti-HIV antibodies, which are useful in diagnosis, treatment, or prevention of HIV in an individual in need thereof.

The provision of the crystal structure of a neutralizing antibody, such as PG9 or PG16, complexed with a soluble envelope glycoprotein allows a novel approach for drug or compound discovery, identification, and design for compounds that bind to a neutralizing antibody, such as PG9 or PG16, and thus to anti-HIV antibodies, and therefore compounds that elicit anti-HIV antibodies, which are useful in diagnosis, treatment, or prevention of HIV in an individual in need thereof. Accordingly, the invention provides a computer-based method of rational drug or compound design or identification which comprises: providing the structure of a neutralizing antibody, such as PG9 or PG16, complex as defined by the co-ordinates or the identifying co-ordinates, providing a structure of a candidate compound; and fitting the structure of the candidate to the structure of a neutralizing antibody, such as PG9 or PG16.

In an alternative aspect, the method may use the co-ordinates of atoms of interest of a neutralizing antibody, such as PG9 or PG16, which are in the vicinity of the active site or binding region in order to model the pocket in which the substrate or ligand binds. These co-ordinates may be used to define a space which is then screened "in silico" against a candidate molecule. Thus, the invention provides a computer-based method of rational drug or compound design or identification which comprises: providing the co-ordinates of at least selected co-ordinates; providing the structure of a candidate compound; and fitting the structure of the candidate to the selected co-ordinates.

In practice, it may be desirable to model a sufficient number of atoms of a neutralizing antibody, such as PG9 or PG16, as defined by its co-ordinates which represent the active site or binding region. Thus, there can be provided the co-ordinates of at least 5, advantageously at least 10, more advantageously at least 50 and even more advantageously at least 100 atoms of the structure.

Accordingly, the methods of the invention can employ a sub-domain of interest of a neutralizing antibody, such as PG9 or PG16, which is in the vicinity of the active site or binding region, and the invention can provide a computer-based method for identifying or rationally designing a compound or drug which comprises: providing the coordinates of at least a sub-domain of; providing the structure of a candidate modulator or inhibitor of a neutralizing antibody, such as PG9 or PG16; and fitting the structure of the candidate to the co-ordinates of the sub-domain provided.

These methods can optionally include synthesizing the candidate and can optionally further include contacting the candidate with a neutralizing antibody, such as PG9 or PG16, to test whether there is binding and/or inhibition and/or administering the compound to an animal capable of eliciting antibodies and testing whether the compound elicits anti-HIV antibodies. Compounds which elicit anti-HIV antibodies are useful for diagnostic purposes, as well as for immunogenic, immunological or even vaccine compositions, as well as pharmaceutical compositions.

"Fitting" can mean determining, by automatic or semi-automatic means, interactions between at least one atom of the candidate and at least one atom of a neutralizing antibody, such as PG9 or PG16, and calculating the extent to which such an interaction is stable. Interactions can include attraction, repulsion, brought about by charge, steric considerations, and the like. A "sub-domain" can mean at least one, e.g., one, two, three, or four, complete element(s) of secondary structure.

The step of providing the structure of a candidate molecule may involve selecting the compound by computationally screening a database of compounds for interaction with the active site. For example, a 3-D descriptor for the potential modulator may be derived, the descriptor including geometric and functional constraints derived from the architecture and chemical nature of the active site. The descriptor may then be used to interrogate the compound database, a potential modulator being a compound that has a good match to the features of the descriptor. In effect, the descriptor can be a type of virtual pharmacophore.

In any event, the determination of the three-dimensional structure of a neutralizing antibody, such as PG9 or PG16, complex provides a basis for the design of new and specific compounds that bind to a neutralizing antibody, such as PG9 or PG16, and are useful for eliciting an immune response. For example, from knowing the three-dimensional structure of a neutralizing antibody, such as PG9 or PG16, complex, computer modelling programs may be used to design or identify different molecules expected to interact with possible or confirmed active sites such as binding sites or other structural or functional features of a neutralizing antibody, such as PG9 or PG16.

More specifically, a compound that potentially binds ("binder") to a neutralizing antibody, such as PG9 or PG16, activity can be examined through the use of computer modeling using a docking program such as GRAM, DOCK or AUTODOCK (see Walters et al. Drug Discovery Today, vol. 3, no. 4 (1998), 160-178, and Dunbrack et al. Folding and Design 2 (1997), 27-42). This procedure can include computer fitting of potential binders to a neutralizing antibody, such as PG9 or PG16, to ascertain how well the shape and the chemical structure of the potential binder will bind to the antibody.

Also, computer-assisted, manual examination of the active site or binding site of a neutralizing antibody, such as PG9 or PG16, may be performed. The use of programs such as GRID (P. Goodford, J. Med. Chem, 1985, 28, 849-57)—program that determines probable interaction sites between molecules with various functional groups and the antibody—may also be used to analyze the active site or binding site to predict partial structures of binding compounds.

Computer programs can be employed to estimate the attraction, repulsion or steric hindrance of the two binding partners, e.g., a neutralizing antibody, such as PG9 or PG16, and a candidate binder. Generally, the tighter the fit, the fewer the steric hindrances, and the greater the attractive forces, the more potent the potential binder, since these properties are consistent with a tighter binding constant. Furthermore, the more specificity in the design of a candidate binder, the more likely it is that it will not interact with other proteins as well.

In a further aspect, the invention provides for a method for determining the structure of a binder of a neutralizing antibody, such as PG9 or PG16, bound to a neutralizing antibody, such as PG9 or PG16, said method comprising, (a) providing a crystal of a neutralizing antibody, such as PG9 or PG16, according to the invention, (b) soaking the crystal or another crystal with said binder; and (c) determining the structure of said a neutralizing antibody-binder complex. Such other crystal may have essentially the same coordinates discussed herein, however due to minor alterations in the polypeptide or sequence, the crystal may form in a different space group.

The invention further involves, in place of or in addition to in silico methods, high throughput screening of compounds to select compounds with binding activity. Those compounds which show binding activity may be selected as possible candidate binders, and further crystallized with a neutralizing antibody, such as PG9 or PG16, e.g., by co-crystallization or by soaking, for X-ray analysis. The resulting X-ray structure may be compared with known coordinates for a variety of purposes. For example, where the contacts made by such compounds overlap with those made by a neutralizing antibody, such as PG9 or PG16, novel molecules comprising residues which contain contacts of a neutralizing antibody, such as PG9 or PG16, and other compounds may be provided.

Having designed, identified, or selected possible binding candidate binders by determining those which have favorable fitting properties, e.g., strong attraction between a candidate and a neutralizing antibody, such as PG9 or PG16, these can then be screened for activity. Consequently, the invention further involves: obtaining or synthesizing the candidate modulator or inhibitor; and contacting the candidate binder with a neutralizing antibody, such as PG9 or PG16, to determine the ability of the candidate to bind with a neutralizing antibody, such as PG9 or PG16. In the latter step, the candidate is advantageously contacted with a neutralizing antibody, such as PG9 or PG16, under conditions to determine its function. Instead of, or in addition to, performing such an assay, the invention may comprise: obtaining or synthesizing the candidate modulator, forming a complex of a neutralizing antibody, such as PG9 or PG16, and the candidate, and analyzing the complex, e.g., by X-ray diffraction or NMR or other means, to determine the ability of the candidate to interact with a neutralizing antibody, such as PG9 or PG16. Detailed structural information can then be obtained about the binding of the candidate to a neutralizing antibody, such as PG9 or PG16, and in light of this information, adjustments can be made to the structure or functionality of the potential modulator, e.g., to improve its binding to a neutralizing antibody, such as PG9 or PG16. These steps may be repeated and re-repeated as necessary. Alternatively or additionally, potential binders can be administered to an animal capable of eliciting an antibody response, to ascertain whether the potential binder elicits anti-HIV antibodies.

Once the amino acid sequence of the polypeptides with known and unknown structures are aligned, the structures of the conserved amino acids in a computer representation of the polypeptide with known structure are transferred to the corresponding amino acids of the polypeptide whose structure is unknown. For example, a tyrosine in the amino acid sequence of known structure may be replaced by a phenylalanine, the corresponding homologous amino acid in the amino acid sequence of unknown structure. The structures of amino acids located in non-conserved regions may be assigned manually using standard peptide geometries or by molecular simulation techniques, such as molecular dynamics. Refining the entire structure can be by molecular dynamics and/or energy minimization.

The aspects of the invention which employ the neutralizing antibody, such as PG9 or PG16, structure in silico may be equally applied to homologue models of a neutralizing antibody, such as PG9 or PG16, obtained by the above aspect of the invention and this forms yet a further embodiment of the invention. Thus, having determined a conformation of a neutralizing antibody, such as PG9 or PG16, by the methods described herein, such a conformation may be used in a computer-based method of rational drug or compound design or identification as described herein.

The invention further provides a method for determining the structure of a binder of a neutralizing antibody, such as PG9 or PG16, bound to a neutralizing antibody, such as PG9 or PG16, comprising: providing a crystal of a neutralizing antibody, such as PG9 or PG16, e.g., according to the invention, soaking the crystal with the binder, and determining the structure of the neutralizing antibody-binder complex. Alternatively or additionally the neutralizing antibody, such as PG9 or PG16, and the binder may be co-crystallized.

The invention further provides systems, such as computer systems, intended to generate structures and/or perform rational drug or compound design for a neutralizing antibody, such as PG9 or PG16, or complex of neutralizing antibody, such as PG9 or PG16, and a potential binder. The system can contain: atomic co-ordinate data, said data defining the three-dimensional structure of a neutralizing antibody, such as PG9 or PG16, or at least one sub-domain thereof; or structure factor data for neutralizing antibody, such as PG9 or PG16, said structure factor data being derivable from the atomic co-ordinate data. The invention also involves computer readable media with: atomic co-ordinate data by homology modeling, said data defining the three-dimensional structure of a neutralizing antibody, such as PG9 or PG16, or at least one sub-domain thereof, or structure factor data for neutralizing antibody, such as PG9 or PG16, said structure factor data being derivable from the atomic co-ordinate data. “Computer readable media” refers to any media which can be read and accessed directly by a computer, and includes, but is not limited to: magnetic storage media such as floppy discs, hard storage medium and magnetic tape; optical storage media such as optical discs or CD-ROM; electrical storage media such as RAM and ROM; and hybrids of these categories, such as magnetic/optical media. By providing such computer readable media, the atomic co-ordinate data can be routinely accessed to model a neutralizing antibody, such as PG9 or PG16, or a sub-domain thereof. For example RASMOL (Sayle et al., TIBS vol. 20 (1995), 374) is a publicly available software package which allows access and analysis of atomic co-ordinate data for structural determination and/or rational drug design. The invention further comprehends methods of doing business by providing access to such computer readable media and/or computer systems and/or atomic co-ordinate data to users; e.g., the media and/or atomic co-ordinate data can be accessible to a user, for instance on a subscription basis, via the Internet or a global communication/computer network; or, the computer system can be available to a user, on a subscription basis. Structure factor data, which are derivable from atomic co-ordinate data. (see, e.g., Blundell et al., in Protein Crystallography, Academic Press, NY, London and San Francisco (1976)), are particularly useful for calculating electron density maps, e.g., difference Fourier electron density maps. Thus, there are additional uses for the computer readable media and/or computer systems and/or atomic co-ordinate data and additional reasons to provide them to users. A “computer system” refers to the hardware means, software means and data storage means used to analyze the atomic co-ordinate data of the present invention. The minimum hardware means of computer-based systems of the invention may comprise a central processing unit (CPU), input means, output means, and data storage means. Desirably, a monitor is provided to visualize structure data. The data storage means may be RAM or other means for accessing computer readable media of the invention. Examples of such systems are microcomputer workstations available from Silicon Graphics Incorporated and Sun Microsystems running Unix based, Linux, Windows NT or IBM OS/2 operating systems.

Accordingly, the invention further comprehends methods of transmitting information obtained in any method or step thereof described herein or any information described herein, e.g., via telecommunications, telephone, mass communications, mass media, presentations, internet, email, etc.

The invention also provides a method of analyzing a complex of a neutralizing antibody, such as PG9 or PG16, and a potential binder comprising: employing X-ray crystallographic diffraction data from the complex and a three-dimensional structure of a neutralizing antibody, such as PG9 or PG16, or at least a sub-domain thereof, to generate a different Fourier electron density map of the complex; advantageously, the three-dimensional structure being as defined by its atomic co-ordinate data.

Such complexes can be crystallized and analyzed using X-ray diffraction methods, e.g., according to the approaches described by Greer et al., 1994, and difference Fourier electron density maps can be calculated based on X-ray diffraction patterns of soaked or co-crystallized neutralizing antibody, such as PG9 or PG16, and the solved structure of an uncomplexed neutralizing antibody, such as PG9 or PG16. These maps can then be used to determine whether and where a particular potential binder binds to a neutralizing antibody, such as PG9 or PG16, and/or changes the conformation of a neutralizing antibody, such as PG9 or PG16. Electron density maps can be calculated using programs such as those from the CCP4 computer package (Collaborative Computing Project, No. 4. The CCP4 Suite: Programs for Protein Crystallography, Acta Crystallographica, D50, 1994, 760-763). For map visualization and model building programs such as “QUANTA” (1994, San Diego, Calif.: Molecular Simulations, Jones et al., 1991) can be used.

Determination of the 3D structure of a neutralizing antibody, such as PG9 or PG16, provides important information about the likely active/binding site(s) of a neutralizing antibody, such as PG9 or PG16. This information may be used for rational design of neutralizing antibody binders, e.g., by computational techniques that identify possible binding ligands for the active site(s), by enabling linked-fragment approaches to drug design, and by enabling the identification and location of bound ligands using analyses such as X-ray crystallographic analysis.

Greer et al., supra, relates to an iterative approach to ligand design based on repeated sequences of computer modeling, protein-ligand complex formation, and X-ray analysis. Thymidylate synthase inhibitors were designed by Greer; and, Fab neutralizing antibody binders may also be designed in this way. Using, for example, GRID (P. Goodford, 1985) or the solved 3D structure of Fab neutralizing antibody, such as PG9 or PG16, a potential binder of a neutralizing antibody, such as PG9 or PG16, may be designed that complements the functionalities of the neutralizing antibody active site(s). The potential binder can be synthesized, formed into a complex with a neutralizing antibody, such as PG9 or PG16, and the complex then analyzed, e.g., by X-ray crystallography, NMR or a combination thereof, to identify the actual position of the bound compound.

Determination of the position of the potential binder compound in the complex allows determination of the interactions of it with a neutralizing antibody, such as PG9 or PG16. This allows the skilled artisan to analyze the affinity and specificity of the compound for a neutralizing antibody, such as PG9 or PG16, and to propose modifications to the compound to increase or decrease either or both of these properties. Thus, the structure and/or functional groups of the compound can then be adjusted, if necessary or desired, in view of the results from the analysis (e.g., X-ray analysis), and the synthesis and analysis sequence repeated until an optimized compound is obtained. Related approaches to structure-based drug and compound design are also discussed in other documents cited herein, as well as in Bohacek et al., 1996.

As a result of the determination of the neutralizing antibody, such as PG9 or PG16, 3D structure, more purely computational techniques for rational drug and compound design may also be used to design neutralizing antibody, such as PG9 or PG16, binders and hence compounds that elicit anti-HIV antibodies; for example, automated ligand-receptor docking programs (see Jones et al., 1995) which require accurate information on the atomic co-ordinates of target receptors, may be used to design or identify potential neutralizing antibody, such as PG9 or PG16, binders.

Linked-fragment approaches to drug or compound design also require accurate information on the atomic co-ordinates of a target. Small compounds that have the potential to bind to regions of a neutralizing antibody, such as PG9 or PG16, which in themselves may not be binder compounds may be assembled by chemical linkage to provide potential binders. Thus, the basic idea behind these approaches is to determine the binding locations of more than one, e.g., plural or a plurality of, ligands to a target molecule, and then construct a molecular scaffold to connect the ligands together in such a way that their relative binding positions are preserved. The ligands may be provided computationally and modeled in a computer system, or provided in an experimental setting, wherein crystals according to the invention are provided and more than one, e.g., plural or a plurality of, ligands soaked separately or in mixed pools into the crystal prior to analysis, e.g., X-ray analysis, and determination of their location.

The binding site of two or more ligands are determined and may be connected to thus form a potential lead compound that can be further refined, e.g., the iterative technique of Greer et al. For a virtual linked-fragment approach, see Verlinde et al., 1992; and for NMR and X-ray approaches, see Skuker et al., 1996; and Stout et al., 1998. The use of these or other approaches to design and/or identify neutralizing antibody, such as PG9 or PG16, binders and hence compounds that elicit anti-HIV antibodies (see, e.g., patent documents cited herein such as in the Background Section and documents cited therein, supra) is made possible by the determination of the neutralizing antibody, such as PG9 or PG16, structure.

Many of the techniques and approaches to structure-based described herein employ X-ray analysis to identify the binding position of a potential modulator in a complex with a protein. A common way of doing this is to perform X-ray crystallography on the complex, produce a difference Fourier electron density map, and associate a particular pattern of electron density with the potential modulator. However, to produce a map (See Blundell et al., supra), it is important to know the 3D structure of the protein beforehand (or at least the protein structure factors). Therefore, determination of the neutralizing antibody, such as PG9 or PC16, structure also allows difference Fourier electron density maps of complexes of neutralizing antibody, such as PG9 or PG16, with a potential modulator to be produced, which can greatly assist in the process of rational compound and/or drug design or identification.

The approaches to structure-based drug or compound design or identification described herein involve initial identification of possible compounds for interaction with the target molecule (in this case a neutralizing antibody, such as PG9 or PG16), and thus elicit anti-HIV antibodies. Sometimes these compounds are known, e.g., from research literature. However, when they are not, or when novel compounds are wanted, a first stage of the drug or compound design or identification program may involve computer-based in silico screening of compound databases (such as the Cambridge Structural Database) with the aim of identifying compounds which interact with the active site or sites of the target bio-molecule (in this case a neutralizing antibody, such as PG9 or PG16). Screening selection criteria may be based on pharmacokinetic properties such as metabolic stability and toxicity. However, determination of the neutralizing antibody, such as PG9 or PG16, structure allows the architecture and chemical nature of each neutralizing antibody, such as PG9 or PG16, active site to be identified, which in turn allows the geometric and functional constraints of a descriptor for the potential binder to be derived. The descriptor can be, therefore, a type of virtual 3D pharmacophore, which can also be used as selection criteria or filter for database screening.

Compounds which have a chemical structure selected using the invention, wherein said compounds are neutralizing antibody, such as PG9 or PG16, binders, form a further aspect of the invention; and, such compounds may be used in methods of medical treatments, such as for diagnosis, preventing or treating HIV or for eliciting antibodies for diagnosis of HIV, including use in vaccines. Further, such compounds may be used in the preparation of medicaments for such treatments or prevention, or compositions for diagnostic purposes. The compounds may be employed alone or in combination with other treatments, vaccines or preventatives; and, the compounds may be used in the preparation of combination medicaments for such treatments or prevention, or in kits containing the compound and the other treatment or preventative.

In yet another embodiment, the present invention also encompassed the use of the soluble envelope glycoproteins described herein as immunogens, advantageously as HIV-1 vaccine components.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, F(ab')$_2$, Fv and scFv which are capable of binding the epitope determinant. These antibody fragments retain some ability to selectively bind with its antigen or receptor and include, for example:

Fab, the fragment which contains a monovalent antigen-binding fragment of an antibody molecule can be produced by digestion of whole antibody with the enzyme papain to yield an intact light chain and a portion of one heavy chain;

Fab', the fragment of an antibody molecule can be obtained by treating whole antibody with pepsin, followed by reduction, to yield an intact light chain and a portion of the heavy chain; two Fab' fragments are obtained per antibody molecule;

F(ab')$_2$, the fragment of the antibody that can be obtained by treating whole antibody with the enzyme pepsin without subsequent reduction; F(ab')$_2$ is a dimer of two Fab' fragments held together by two disulfide bonds;

scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

A "neutralizing antibody" may inhibit the entry of HIV-1 virus for example SF162 and/or JRCSF with a neutralization index >1.5 or >2.0. Broad and potent neutralizing antibodies may neutralize greater than about 50% of HIV-1 viruses (from diverse clades and different strains within a clade) in a neutralization assay. The inhibitory concentration of the monoclonal antibody may be less than about 25 mg/ml to neutralize about 50% of the input virus in the neutralization assay.

It should be understood that the proteins, including the antibodies and/or antigens of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may be used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and Int sequences of the invention may be altered in these ways.

As regards codon optimization, the nucleic acid molecules of the invention have a nucleotide sequence that encodes the antigens of the invention and can be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens can be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention can readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and antibodies and/or antigens of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies and/or antigens of the present invention may be used in accordance with the present invention. In certain embodiments, the antigens and/or antibodies of the present invention may be used in vitro (such as using cell-free expression systems) and/or in cultured cells grown in vitro in order to produce the encoded HIV-antigens and/or antibodies which may then be used for various applications such as in the production of proteinaceous vaccines. For such applications, any vector that allows expression of the antigens and/or antibodies in vitro and/or in cultured cells may be used.

For applications where it is desired that the antibodies and/or antigens be expressed in vivo, for example when the transgenes of the invention are used in DNA or DNA-containing vaccines, any vector that allows for the expression of the antibodies and/or antigens of the present invention and is safe for use in vivo may be used. In preferred embodiments the vectors used are safe for use in humans, mammals and/or laboratory animals.

For the antibodies and/or antigens of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The present invention relates to a recombinant vector expressing a foreign epitope. Advantageously, the epitope is an HIV epitope. In an advantageous embodiment, the HIV epitope is a soluble envelope glycoprotein, however, the present invention may encompass additional HIV antigens, epitopes or immunogens. Advantageously, the HIV epitope is an HIV antigen, HIV epitope or an HIV immunogen, such as, but not limited to, the HIV antigens, HIV epitopes or HIV immunogens of U.S. Pat. Nos. 7,341,731; 7,335,364; 7,329,807; 7,323,553; 7,320,859; 7,311,920; 7,306,798; 7,285,646; 7,285,289; 7,285,271; 7,282,364; 7,273,695; 7,270,997; 7,262,270; 7,244,819; 7,244,575; 7,232,567; 7,232,566; 7,223,844; 7,223,739; 7,223,534; 7,223,368; 7,220,554; 7,214,530; 7,211,659; 7,211,432; 7,205,159; 7,198, 934; 7,195,768; 7,192,555; 7,189,826; 7,189,522; 7,186,507; 7,179,645; 7,175,843; 7,172,761; 7,169,550; 7,157,083; 7,153,509; 7,147,862; 7,141,550; 7,129,219; 7,122,188; 7,118,859; 7,118,855; 7,118,751; 7,118,742; 7,105,655; 7,101,552; 7,097,971; 7,097,842; 7,094,405; 7,091,049; 7,090,648; 7,087,377; 7,083,787; 7,070,787; 7,070,781; 7,060,273; 7,056,521; 7,056,519; 7,049,136; 7,048,929; 7,033,593; 7,030,094; 7,022,326; 7,009,037; 7,008,622; 7,001,759; 6,997,863; 6,995,008; 6,979,535; 6,974,574; 6,972,126; 6,969,609; 6,964,769; 6,964,762; 6,958,158; 6,956,059; 6,953,689; 6,951,648; 6,946,075; 6,927,031; 6,919,319; 6,919,318; 6,919,077; 6,913,752; 6,911,315; 6,908,617; 6,908,612; 6,902,743; 6,900,010; 6,893,869; 6,884,785; 6,884,435; 6,875,435; 6,867,005; 6,861,234; 6,855,539; 6,841,381 6,841,345; 6,838,477; 6,821,955; 6,818,392; 6,818,222; 6,815,217; 6,815,201; 6,812,026; 6,812,025; 6,812,024; 6,808,923; 6,806,055; 6,803,231; 6,800,613; 6,800,288; 6,797,811; 6,780,967; 6,780,598; 6,773,920; 6,764,682; 6,761,893; 6,753,015; 6,750,005; 6,737,239; 6,737,067; 6,730,304; 6,720,310; 6,716,823; 6,713,301; 6,713,070; 6,706,859; 6,699,722; 6,699,656; 6,696,291; 6,692,745; 6,670,181; 6,670,115; 6,664,406; 6,657,055; 6,657,050; 6,656,471; 6,653,066; 6,649,409; 6,649,372; 6,645,732; 6,641,816; 6,635,469; 6,613,530; 6,605,427; 6,602,709; 6,602,705; 6,600,023; 6,596,477; 6,596,172; 6,593,103; 6,593,079; 6,579,673; 6,576,758; 6,573,245; 6,573,040; 6,569,418; 6,569,340; 6,562,800; 6,558,961; 6,551,828; 6,551,824; 6,548,275; 6,544,780; 6,544,752; 6,544,728; 6,534,482; 6,534,312; 6,534,064; 6,531,572; 6,531,313; 6,525,179; 6,525,028; 6,524,582; 6,521,449; 6,518,030; 6,518,015; 6,514,691; 6,514,503; 6,511,845; 6,511,812; 6,511,801; 6,509,313; 6,506,384; 6,503,882; 6,495,676; 6,495,526; 6,495,347; 6,492,123; 6,489,131; 6,489,129; 6,482,614; 6,479,286; 6,479,284; 6,465,634; 6,461,615; 6,458,560; 6,458,527; 6,458,370; 6,451,601; 6,451,592; 6,451,323; 6,436,407; 6,432,633; 6,428,970; 6,428,952; 6,428,790; 6,420,139; 6,416,997; 6,410,318; 6,410,028; 6,410,014; 6,407,221; 6,406,710; 6,403,092; 6,399,295; 6,392,013; 6,391,657; 6,384,198; 6,380,170; 6,376,170; 6,372,426; 6,365,187; 6,358,739; 6,355,248; 6,355,247; 6,348,450; 6,342,372; 6,342,228; 6,338,952; 6,337,179; 6,335,183; 6,335,017; 6,331,404; 6,329,202; 6,329,173; 6,328,976; 6,322,964; 6,319,666; 6,319,665; 6,319,500; 6,319,494; 6,316,205; 6,316,003; 6,309,633; 6,306,625; 6,296,807; 6,294,322; 6,291,239; 6,291,157; 6,287,568; 6,284,456; 6,284,194; 6,274,337; 6,270,956; 6,270,769; 6,268,484; 6,265,562; 6,265,149; 6,262,029; 6,261,762; 6,261,571; 6,261,569; 6,258,599; 6,258,358; 6,248,332; 6,245,331; 6,242,461; 6,241,986; 6,235,526; 6,235,466; 6,232,120; 6,228,361; 6,221,579; 6,214,862; 6,214,804; 6,210,963; 6,210,873; 6,207,185; 6,203,974; 6,197,755; 6,197,531; 6,197,496; 6,194,142; 6,190,871; 6,190,666; 6,168,923; 6,156,302; 6,153,408; 6,153,393; 6,153,392; 6,153,378; 6,153,377; 6,146,635; 6,146,614; 6,143,876 6,140,059; 6,140,043; 6,139,746; 6,132,992; 6,124,306; 6,124,132; 6,121,006; 6,120,990; 6,114,507; 6,114,143; 6,110,466; 6,107,020; 6,103,521; 6,100,234; 6,099,848; 6,099,847; 6,096,291; 6,093,405; 6,090,392; 6,087,476; 6,083,903; 6,080,846; 6,080,725; 6,074,650; 6,074,646; 6,070,126; 6,063,905; 6,063,564; 6,060,256; 6,060,064; 6,048,530; 6,045,788; 6,043,347; 6,043,248; 6,042,831; 6,037,165; 6,033,672; 6,030,772; 6,030,770; 6,030,618; 6,025,141; 6,025,125; 6,020,468; 6,019,979; 6,017,543; 6,017,537; 6,015,694; 6,015,661; 6,013,484; 6,013,432; 6,007,838; 6,004,811; 6,004,807; 6,004,763; 5,998,132; 5,993,819; 5,989,806; 5,985,926; 5,985,641; 5,985,545; 5,981,537; 5,981,505; 5,981,170; 5,976,551; 5,972,339; 5,965,371; 5,962,428; 5,962,318; 5,961,979; 5,961,970; 5,958,765; 5,958,422; 5,955,647; 5,955,342; 5,951,986; 5,951,975; 5,942,237; 5,939,277; 5,939,074; 5,935,580; 5,928,930; 5,928,913; 5,928,644; 5,928,642; 5,925,513; 5,922,550; 5,922,325; 5,919,458; 5,916,806; 5,916,563; 5,914,395; 5,914,109; 5,912,338; 5,912,176; 5,912,170; 5,906,936; 5,895,650; 5,891,623; 5,888,726; 5,885,580 5,885,578; 5,879,685; 5,876,731; 5,876,716; 5,874,226; 5,872,012; 5,871,747; 5,869,058; 5,866,694; 5,866,341; 5,866,320; 5,866,319; 5,866,137; 5,861,290; 5,858,740; 5,858,647; 5,858,646; 5,858,369; 5,858,368; 5,858,366; 5,856,185; 5,854,400; 5,853,736; 5,853,725; 5,853,724; 5,852,186; 5,851,829; 5,851,529; 5,849,475; 5,849,288; 5,843,728; 5,843,723; 5,843,640; 5,843,635; 5,840,480; 5,837,510; 5,837,250; 5,837,242; 5,834,599; 5,834,441; 5,834,429; 5,834,256; 5,830,876; 5,830,641; 5,830,475; 5,830,458; 5,830,457; 5,827,749; 5,827,723; 5,824,497; 5,824,304; 5,821,047; 5,817,767; 5,817,754; 5,817,637; 5,817,470; 5,817,318; 5,814,482; 5,807,707; 5,804,604; 5,804,371; 5,800,822; 5,795,955; 5,795,743; 5,795,572; 5,789,388; 5,780,279; 5,780,038; 5,776,703; 5,773,260; 5,770,572; 5,766,844; 5,766,842; 5,766,625; 5,763,574; 5,763,190; 5,762,965; 5,759,769; 5,756,666; 5,753,258; 5,750,373; 5,747,641; 5,747,526; 5,747,028; 5,736,320; 5,736,146; 5,733,760; 5,731,189; 5,728,385; 5,721,095; 5,716,826; 5,716,637; 5,716,613; 5,714,374; 5,709,879; 5,709,860; 5,709,843; 5,705,331; 5,703,057; 5,702,707 5,698,178; 5,688,914; 5,686,078; 5,681,831; 5,679,784; 5,674,984; 5,672,472; 5,667,964; 5,667,783; 5,665,536; 5,665,355; 5,660,990; 5,658,745; 5,658,569; 5,643,756; 5,641,624; 5,639,854; 5,639,598; 5,637,677; 5,637,455; 5,633,234; 5,629,153; 5,627,025; 5,622,705; 5,614,413; 5,610,035; 5,607,831; 5,606,026; 5,601,819; 5,597,688; 5,593,972; 5,591,829; 5,591,823; 5,589,466; 5,587,285; 5,585,254; 5,585,250; 5,580,773; 5,580,739; 5,580,563; 5,573,916; 5,571,667; 5,569,468; 5,558,865; 5,556,745; 5,550,052; 5,543,328; 5,541,100; 5,541,057; 5,534,406; 5,529,765; 5,523,232; 5,516,895; 5,514,541; 5,510,264; 5,500,161; 5,480,967; 5,480,966; 5,470,701; 5,468,606; 5,462,852; 5,459,127; 5,449,601; 5,447,838; 5,447,837; 5,439,809; 5,439,792; 5,418,136; 5,399,501; 5,397,695; 5,391,479; 5,384,240; 5,374,519; 5,374,518; 5,374,516; 5,364,933; 5,359,046; 5,356,772; 5,354,654; 5,344,755; 5,335,673; 5,332,567; 5,320,940; 5,317,009; 5,312,902; 5,304,466; 5,296,347; 5,286,852; 5,268,265; 5,264,356; 5,264,342; 5,260,308; 5,256,767; 5,256,561; 5,252,556; 5,230,998; 5,230,887; 5,227,159; 5,225,347; 5,221,610 5,217,861; 5,208,321; 5,206,136; 5,198,346; 5,185,147; 5,178,865; 5,173,400; 5,173,399; 5,166,050; 5,156,951; 5,135,864; 5,122,446; 5,120,662; 5,103,836; 5,100,777; 5,100,662; 5,093,230; 5,077,284; 5,070,010; 5,068,174; 5,066,782; 5,055,391; 5,043,262; 5,039,604; 5,039,522; 5,030,718; 5,030,555; 5,030,449; 5,019,387; 5,013,556; 5,008,183; 5,004,697; 4,997,772; 4,983,529; 4,983,387; 4,965,069; 4,945,082; 4,921,787; 4,918,166; 4,900,548; 4,888,290; 4,886,742; 4,885,235; 4,870,003; 4,869,903; 4,861,707; 4,853,326; 4,839,288; 4,833,072 and 4,795,739.

In another embodiment, HIV, or immunogenic fragments thereof, may be utilized as the HIV epitope. For example, the HIV nucleotides of U.S. Pat. Nos. 7,393,949, 7,374,877, 7,306,901, 7,303,754, 7,173,014, 7,122,180, 7,078,516, 7,022,814, 6,974,866, 6,958,211, 6,949,337, 6,946,254, 6,896,900, 6,887,977, 6,870,045, 6,803,187, 6,794,129, 6,773,915, 6,768,004, 6,706,268, 6,696,291, 6,692,955, 6,656,706, 6,649,409, 6,627,442, 6,610,476, 6,602,705, 6,582,920, 6,557,296, 6,531,587, 6,531,137, 6,500,623, 6,448,078, 6,429,306, 6,420,545, 6,410,013, 6,407,077, 6,395,891, 6,355,789, 6,335,158, 6,323,185, 6,316,183, 6,303,293, 6,300,056, 6,277,561, 6,270,975, 6,261,564, 6,225,045, 6,222,024, 6,194,391, 6,194,142, 6,162,631, 6,114,167, 6,114,109, 6,090,392, 6,060,587, 6,057,102, 6,054,565, 6,043,081, 6,037,165, 6,034,233, 6,033,902, 6,030,769, 6,020,123, 6,015,661, 6,010,895, 6,001,555, 5,985,661, 5,980,900, 5,972,596, 5,939,538, 5,912,338, 5,869,339, 5,866,701, 5,866,694, 5,866,320, 5,866,137, 5,864,027, 5,861,242, 5,858,785, 5,858,651, 5,849,475, 5,843,638, 5,840,480, 5,821,046, 5,801,056, 5,786,177, 5,786,145, 5,773,247, 5,770,703, 5,756,674, 5,741,706, 5,705,612, 5,693,752, 5,688,637, 5,688,511, 5,684,147, 5,665,577, 5,585,263, 5,578,715, 5,571,712, 5,567,603, 5,554,528, 5,545,726, 5,527,895, 5,527,894, 5,223,423, 5,204,259, 5,144,019, 5,051,496 and 4,942,122 are useful for the present invention.

Any epitope recognized by an HIV antibody may be used in the present invention. For example, the anti-HIV antibodies of U.S. Pat. Nos. 6,949,337, 6,900,010, 6,821,744, 6,768,004, 6,613,743, 6,534,312, 6,511,830, 6,489,131, 6,242,197, 6,114,143, 6,074,646, 6,063,564, 6,060,254, 5,919,457, 5,916,806, 5,871,732, 5,824,304, 5,773,247, 5,736,320, 5,637,455, 5,587,285, 5,514,541, 5,317,009, 4,983,529, 4,886,742, 4,870,003 and 4,795,739 are useful for the present invention. Furthermore, monoclonal anti-HIV antibodies of U.S. Pat. Nos. 7,074,556, 7,074,554, 7,070,787, 7,060,273, 7,045,130, 7,033,593, RE39,057, 7,008,622, 6,984,721, 6,972,126, 6,949,337, 6,946,465, 6,919,077, 6,916,475, 6,911,315, 6,905,680, 6,900,010, 6,825,217, 6,824,975, 6,818,392, 6,815,201, 6,812,026, 6,812,024, 6,797,811, 6,768,004, 6,703,019, 6,689,118, 6,657,050, 6,608,179, 6,600,023, 6,596,497, 6,589,748, 6,569,143, 6,548,275, 6,525,179, 6,524,582, 6,506,384, 6,498,006, 6,489,131, 6,465,173, 6,461,612, 6,458,933, 6,432,633, 6,410,318, 6,406,701, 6,395,275, 6,391,657, 6,391,635, 6,384,198, 6,376,170, 6,372,217, 6,344,545, 6,337,181, 6,329,202, 6,319,665, 6,319,500, 6,316,003, 6,312,931, 6,309,880, 6,296,807, 6,291,239, 6,261,558, 6,248,514, 6,245,331, 6,242,197, 6,241,986, 6,228,361, 6,221,580, 6,190,871, 6,177,253, 6,146,635, 6,146,627, 6,146,614, 6,143,876, 6,132,992, 6,124,132, RE36,866, 6,114,143, 6,103,238, 6,060,254, 6,039,684, 6,030,772, 6,020,468, 6,013,484, 6,008,044, 5,998,132, 5,994,515, 5,993,812, 5,985,545, 5,981,278, 5,958,765, 5,939,277, 5,928,930, 5,922,325, 5,919,457, 5,916,806, 5,914,109, 5,911,989, 5,906,936, 5,889,158, 5,876,716, 5,874,226, 5,872,012, 5,871,732, 5,866,694, 5,854,400, 5,849,583, 5,849,288, 5,840,480, 5,840,305, 5,834,599, 5,831,034, 5,827,723, 5,821,047, 5,817,767, 5,817,458, 5,804,440, 5,795,572, 5,783,670, 5,776,703, 5,773,225, 5,766,944, 5,753,503, 5,750,373, 5,747,641, 5,736,341, 5,731,189, 5,707,814, 5,702,707, 5,698,178, 5,695,927, 5,665,536, 5,658,745, 5,652,138, 5,645,836, 5,635,345, 5,618,922, 5,610,035, 5,607,847, 5,604,092, 5,601,819, 5,597,896, 5,597,688, 5,591,829, 5,558,865, 5,514,541, 5,510,264, 5,478,753, 5,374,518, 5,374,516, 5,344,755, 5,332,567, 5,300,433, 5,296,347, 5,286,852, 5,264,221, 5,260,308, 5,256,561, 5,254,457, 5,230,998, 5,227,159, 5,223,408, 5,217,895, 5,180,660, 5,173,399, 5,169,752, 5,166,050, 5,156,951, 5,140,105, 5,135,864, 5,120,640, 5,108,904, 5,104,790, 5,049,389, 5,030,718, 5,030,555, 5,004,697, 4,983,529, 4,888,290, 4,886,742 and 4,853,326, are also useful for the present invention.

The vectors used in accordance with the present invention should typically be chosen such that they contain a suitable gene regulatory region, such as a promoter or enhancer, such that the antigens and/or antibodies of the invention can be expressed.

For example, when the aim is to express the antibodies and/or antigens of the invention in vitro, or in cultured cells, or in any prokaryotic or eukaryotic system for the purpose of producing the protein(s) encoded by that antibody and/or antigen, then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the antibodies and/or antigens under the identified circumstances.

When the aim is to express the antibodies and/or antigens of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antibodies and/or antigens of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors.

The nucleotide sequences and vectors of the invention can be delivered to cells, for example if aim is to express and the HIV-1 antigens in cells in order to produce and isolate the expressed proteins, such as from cells grown in culture. For expressing the antibodies and/or antigens in cells any suitable transfection, transformation, or gene delivery methods can be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies and/or antigens can be carried out in any suitable type of host cells, such as bacterial cells, yeast, insect cells, and mammalian cells. The antibodies and/or antigens of the invention can also be expressed using including in vitro transcription/translation systems. All of such methods are well known by those skilled in the art, and one of skill in the art would readily be able to select a suitable method depending on the nature of the nucleotide sequences, vectors, and cell types used.

In preferred embodiments, the nucleotide sequences, antibodies and/or antigens of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences, antibodies and/or antigens of the invention are preferably administered as a component of an immunogenic composition comprising the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antibodies and/or antigens of the invention to a subject, such as a human, such that the antibodies and/or antigens are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri (caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, Calif.).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., AlK(SO$_4$)$_2$, AlNa(SO$_4$)$_2$, AlNH(SO$_4$)$_2$, silica, alum, Al(OH)$_3$, Ca$_3$(PO$_4$)$_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the 34$^{th}$ Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D from *Mycobacteriumn tuberculosis*, substances found in *Cornyebacterium parvum, Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, A. K. et al (2004) 22(13-14): 1791-8), and the CCR5 inhibitor CMPD167 (see Veazey, R. S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA1-DD/ISCOMs (see Mowat, A. M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or α-galactosyl ceramide; see Green, T. D. et al, (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the antigens of the invention or on separate expression vectors.

In an advantageous embodiment, the adjuvants may be lecithin combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced BioAdjuvants (ABA)).

The immunogenic compositions can be designed to introduce the nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention (collectively, the immunogens) in the immunogenic composition of the invention can be readily determined by those of skill in the art. For example, the dosage of the immunogens can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions can serve to provide protective immunity of a subject against HIV-1 infection or to prevent or attenuate the progression of AIDS in a subject already infected with HIV-1. When provided therapeutically, the immunogenic compositions can serve to ameliorate and treat AIDS symptoms and are advantageously used as soon after infection as possible, preferably before appearance of any symptoms of AIDS but may also be used at (or after) the onset of the disease symptoms.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes can be oral, intranasal or by any other suitable route. Delivery also be accomplished via a mucosal surface such as the anal, vaginal or oral mucosa.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, for example DNA prime-Adenovirus boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

A specific embodiment of the invention provides methods of inducing an immune response against HIV in a subject by administering an immunogenic composition of the invention, preferably comprising an adenovirus vector containing DNA encoding one or more of the epitopes of the invention, one or more times to a subject wherein the epitopes are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such preferred immunogen is HIVA (described in WO 01/47955), which can be administered as a protein, on a plasmid (e.g., pTHr.HIVA) or in a viral vector (e.g., MVA-.HIVA). Another such HIV immunogen is RENTA (described in PCT/US2004/037699), which can also be administered as a protein, on a plasmid (e.g., pTHr.RENTA) or in a viral vector (e.g., MVA.RENTA).

For example, one method of inducing an immune response against HIV in a human subject comprises administering at least one priming dose of an HIV immunogen and at least one boosting dose of an HIV immunogen, wherein the immunogen in each dose can be the same or different, provided that at least one of the immunogens is an epitope of the present invention, a nucleic acid encoding an epitope of the invention or an expression vector, preferably a VSV vector, encoding an epitope of the invention, and wherein the immunogens are administered in an amount or expressed at a level sufficient to induce an HIV-specific immune response in the subject. The IV-specific immune response can include an HIV-specific T-cell immune response or an HIV-specific B-cell immune response. Such immunizations can be done at intervals, preferably of at least 2-6 or more weeks.

The invention will now be further described by way of the following non-limiting examples.

EXAMPLES

Example 1

Identification of Soluble HIV-1 Envs with Better Binding to PG9/PG16

Shed gp120 were screened as follows. More than 50 HIV-1 Envs from Tier II Clade B, C, Indian clade C panel, some tier I clade B and few founder virus envelopes were tested.

The method for screening shed gp120 was as follows:
Transfect 293T cells with NL4-3 back bond and HIV-1 Env plasmids;
Collect supernatant;
Capture shed gp120 on ELISA plate coated with D7324 (anti-C5 polyclonal); and
Probe the captured Env for binding to b12, PG9 and PG16.

Applicants have codon optimized gp120 and gp140 versions of all the four Indian Clade C strains that show exceptional binding to PG9. Applicants have tested the Envs by transient transfection and they maintain the property of binding as seen on shed gp20. Applicants may use these Envs for immunogenicity studies, to generate tools for mapping of PG9-like antibodies in sera and/or generate resurfaced gp120 for better presentation of a PG9 epitope.

Example 2

Stabilizing Mutation BG505 L111A for HIV Envelope Proteins

The Example relates to a way to stabilize a recombinant Clade A HIV Envelope (Env) protein. It is a mutation L111A that eliminates aggregates but also further stabilizes proteins. The mutation was described earlier as reducing the formation of dimers in a Clade B protein (Finzi A et al. J Virol Methods. 2010 September; 168(1-2):155-61). The same mutation introduced into Clade A Env protein not only did that but also allowed purification of HIV gp120 proteins that was not possible before, thus increasing overall stability of the protein. Further analysis of proteins carrying this mutation confirmed that these proteins retain full antigenicity of the wild type protein, i.e. binding of neutralizing antibodies associated with resistance to HIV. Applicants have tested antibody binding for several conformation variants of Envelope protein: gp120 secreted and purified from mammalian cells, gp140 with an artificial trimerization motif, and gp160 on a cell surface. Also an HIV pseudovirus was tested in a neutralization assay as well as cells infected with a recombinant VSV virus. For a vaccine application it is important to retain the properties of an immunogen in a formulation that can be delivered to vaccinated subjects. For that purpose Applicants confirmed that the mutated Clade A envelope protein adsorbed on the surface of Alum (aluminum phosphate) particles (widely used vaccine adjuvant) retains its ability to interact with neutralizing antibodies. Clade A L111A gp120 was used for immunization of rabbits in a DNA prime—protein boost immunization experiment.

The resulting sera from immunized animals showed antibody binding to cognate and alternative Envelope proteins. It also was capable of neutralizing Tier 1 and Tier 2 HIV pseudoviruses.

The universal value of this mutation was confirmed by creating another envelope protein, Clade C, with improved aggregation properties.

Original wild type sequences were aligned with HxB2 reference strain of HIV Envelope protein. The Leucine in the position corresponding to 111 in HxB2 was replaced by Alanine. Actual mutagenesis was performed by GeneArt (Life Technologies) and DNA was delivered in pCI-Neo or pcDNA plasmid. Several versions of Clade A BG505 were made: gp120, gp140, gp140 with GCN4 trimerization motif, and gp160 delta CT (without cytoplasmic tail).

Envelope proteins carrying L111A mutation and non-mutated (wild type) versions were produced by DNA transient transfection of HEK 293T or HEK 293S cells. 293T and 293 S cells differ in the type of glycosylation of secreted recombinant proteins. The former producing proteins with complex oligosaccharides, while the latter producing proteins with oligomannose-type glycans.

Proteins secreted to the cell culture media were purified by using affinity chromatography on Galanthus nivalis (snowdrop) lectin (GNL) column. (Gilljam G. AIDS Res Hum Retroviruses. 1993 May; 9(5):431-8)

Antigenicity (antibody binding) was measured with multiple human antibodies isolated from HIV-infected subjects. Methods used to measure antigenicity: ELISA for soluble recombinant Envs captured through His-tags, and flow cytometry (FACS) for gp160 Envs expressed on the cell surface.

For neutralization assay HIV pseudo viruses were generated in 293T cells with Clade A gp160 on the virus surface. Neutralizing antibody activity was measured by monitoring reduction in Luciferase reporter expression after a single cycle of virus infection in TZM-b1 cells (Li M et al. J. Virol. 2005 August; 79(16):10108-25).

Immunogenicity studies were conducted in rabbits. With DNA prime for Clade A L111A gp120, followed by protein boost with purified Clade A L111A gp120. For this study protein was purified from HEK 293S cells. Blood was collected and analyzed for overall anti-HIV gp120 titers by ELISA with JR-CSF gp120 as a standard. Further analysis was done by measuring neutralization of a panel of Tier 1 and Tier 2 pseudoviruses in TZM-b1 assay by rabbit sera (Li M et al. Virol. 2005 August; 79(16):10108-25 and Mascola J R et al. Virol. 2005 August; 79(16):10103-7).

Figure 3:
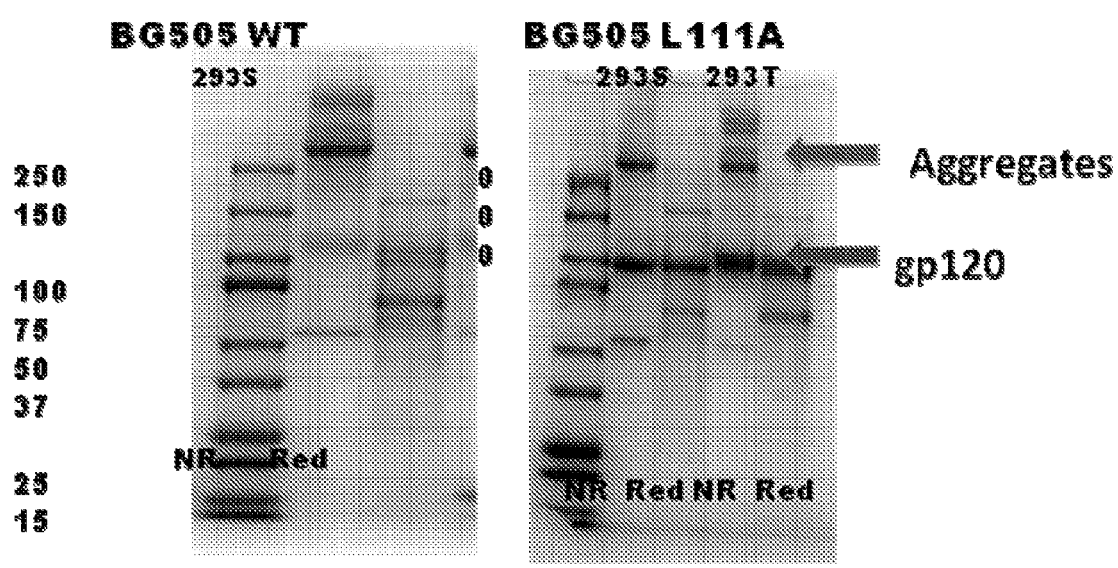
FIG. 3 depicts a BG505 L111A mutant which has lower aggregation than the original protein. Samples in non-reduced (NR) or reduced (Red) form were separated by SDS-PAGE (poly acrylamide gel electrophoresis). Each sample contains 5 μg of protein. Applicants attempted purification of BG505 gp120 but came up with a protein that was highly aggregated and with low activity. A mutant of the BG505 with a predicted lower aggregation pattern (Finzi A et al., J Virol Methods. 2010 September; 168(1-2):155-61) was made and expressed in both HEK 293S and 293T cells.

FIG. 3 depicts a BG505 L111A mutant which has lower aggregation than the original protein. Samples in non-reduced (NR) or reduced (Red) form were separated by SDS-PAGE (poly acrylamide gel electrophoresis). Each sample contains 5 µg of protein. Applicants attempted purification of BG505 gp120 but came up with a protein that was highly aggregated and with low activity. A mutant of the BG505 with a predicted lower aggregation pattern (Finzi A et al., J Virol Methods. 2010 September; 168(1-2):155-61) was made and expressed in both HEK 293S and 293T cells.

Figure 4:
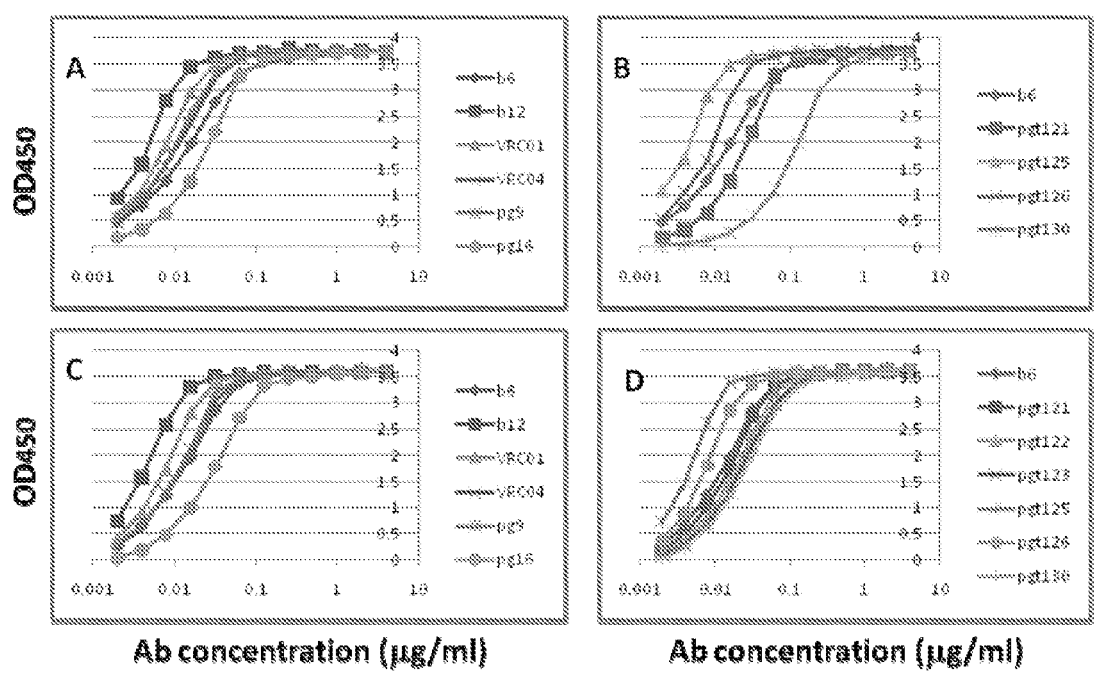
FIG. 4A-D depicts binding to BG505 L111A gp120 in cell culture supernatants. Binding of antibody to BG505 L111A gp120 secreted into cell culture media was measured by Enzyme-linked immunosorbent assay (ELISA) in 96-well microplates. The set of antibodies used to characterize antigenicity included trimer-specific antibodies (PG9, PG16), CD4 binding site (CD4bs) specific antibodies (b6, b12, VRC01, VRC04/PGV04), and PGT series (PGT121-130).

FIG. 4 depicts binding to BG505 L111A gp120 in cell culture supernatants. Binding of antibody to BG505 L111A gp120 secreted into cell culture media was measured by Enzyme-linked immunosorbent assay (ELISA) in 96-well microplates. The set of antibodies used to characterize antigenicity included trimer-specific antibodies (PG9, PG16), CD4 binding site (CD4bs) specific antibodies (b6, b12, VRC01, VRC04/PGV04), and PGT series (PGT121-130).

Figure 5:
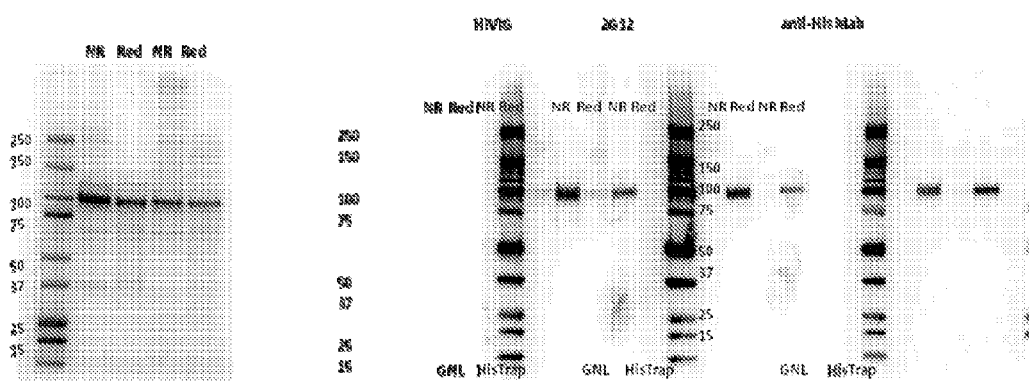
FIG. 5 depicts BG3505 Purification on Lectin and His-Trap Columns. Modified protein can be purified by two different affinity chromatography methods without being damaged and preserving its antigenic capacity. The test was done by western immune blotting with anti-His antibody, broadly neutralizing mannose specific IgG, 2G12, and a pool of immune globulins from HIV-positive individuals (HIVIG). SDS-PAGE: Protein staining (5 micrograms of protein per well) and Western (0.5 micrograms of protein per well)—HIVIG, 2G12 and Anti-His detection. BG505 L111A gp120 was from 293S cells.

FIG. 5 depicts BG505 Purification on Lectin and His-Trap Columns. Modified protein can be purified by two different affinity chromatography methods without being damaged and preserving its antigenic capacity. The test was done by western immune blotting with anti-His antibody, broadly neutralizing mannose specific IgG, 2G12, and a pool of immune globulins from HIV-positive individuals (HIVIG). SDS-PAGE: Protein staining (5 micrograms of protein per well) and Western (0.5 micrograms of protein per well)— HIVIG, 2G12 and Anti-His detection. BG505 L111A gp120 was from 293S cells.

FIG. 6 depicts an antigenicity profile by ELISA of BG505 L111A purified by 2 different chromatographic approaches. Subsequent binding of antibodies proved undistinguishable by ELISA.

FIG. 7 depicts antibody binding to the purified BG505 L111A gp120 protein. Proteins carrying L111A mutation were successfully purified both from 293S and 293T cells by GNL column and preserved their antigenicity which was confirmed by ELISA of purified proteins. With the exception of a few PGT antibodies most broadly neutralizing antibodies bind to BG505 L111A gp120. PGT135, 136 and 141 do not bind to BG505 gp20.

Figure 8:
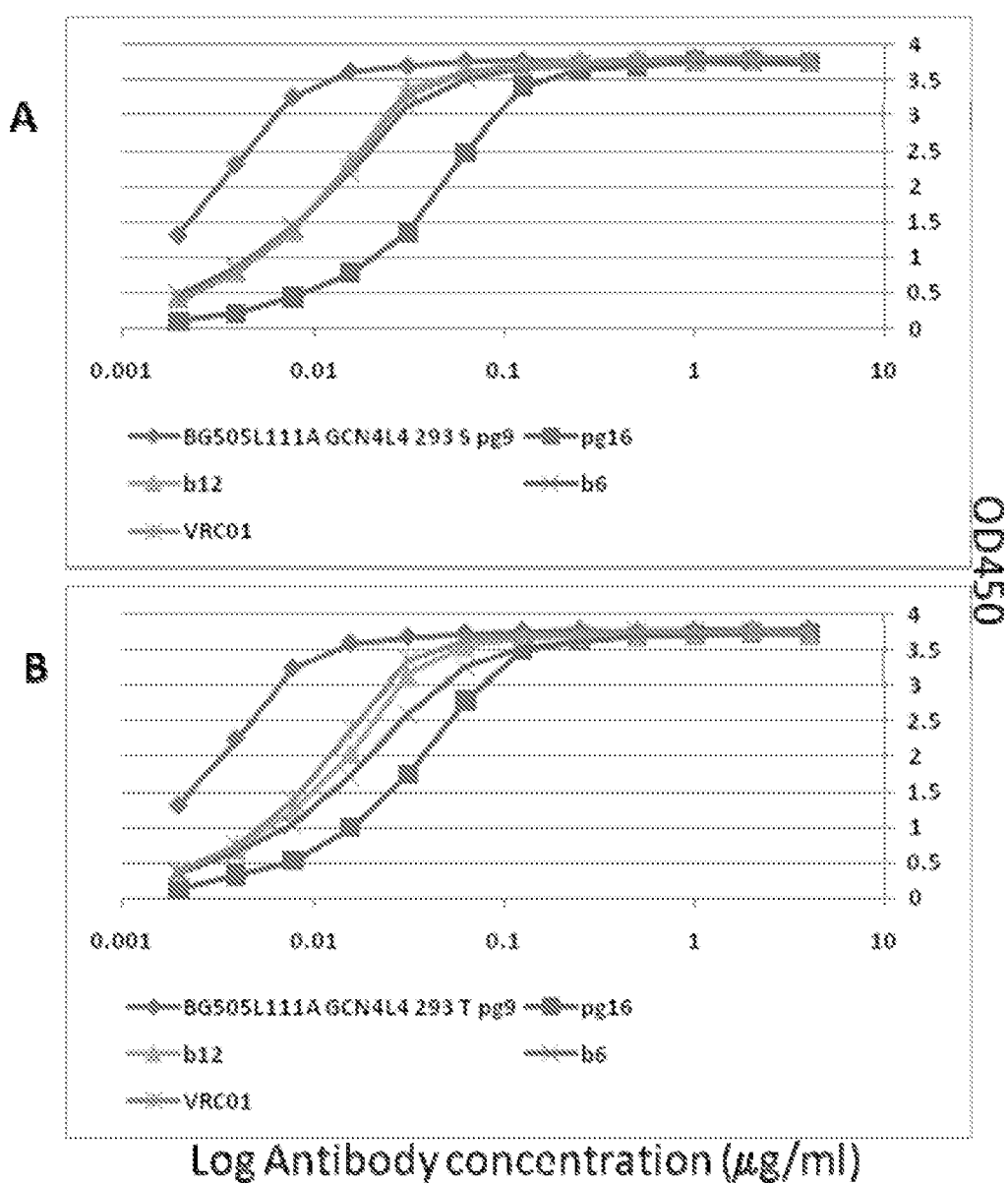
FIG. 8A-B depicts primer-specific and CD4bs—specific Antibody Binding to recombinant BG505 Trimer. Because native HIV Envelope proteins exist as trimer spike on the virus surface Applicants made recombinant trimers to test the effect of the mutation. This figure shows that BG505 L111A preserves the ability to bind anti-gp120 antibodies in a trimer conformation. The trimer was made by adding GCN4 trimerization motif to BG505 L111A gp140 molecule.

FIG. 8 depicts primer-specific and CD4bs—specific Antibody Binding to recombinant BG505 Trimer. Because native HIV Envelope proteins exist as trimer spike on the virus surface Applicants made recombinant trimers to test the effect of the mutation. This figure shows that BG505 L111A preserves the ability to bind anti-gp120 antibodies in a trimer conformation. The trimer was made by adding GCN4 trimerization motif to BG505 L111A gp140 molecule.

Figure 9:
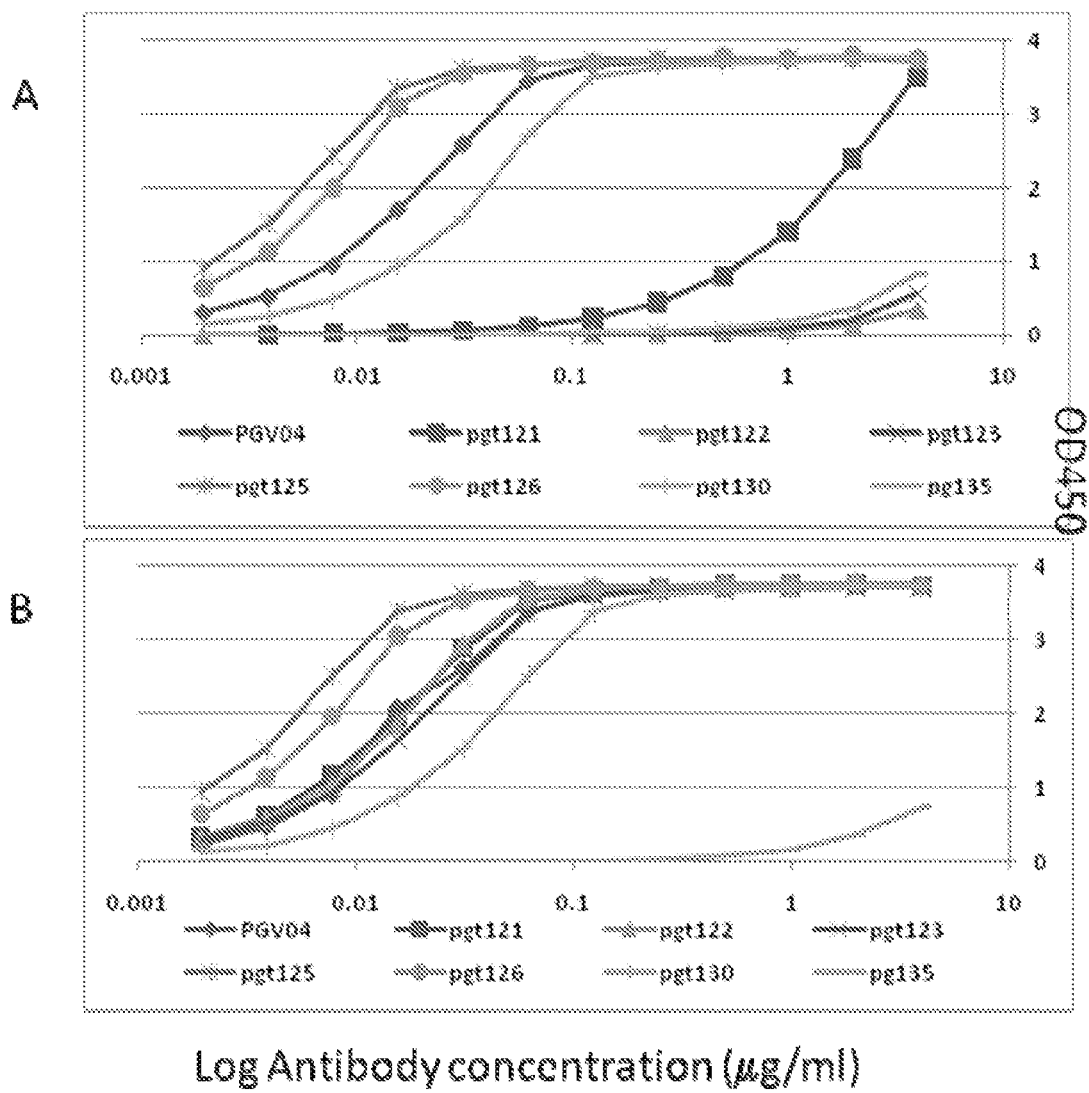
FIG. 9A-B depicts PGT antibodies binding to BG505 L111A gp140 GCN4L4 trimer. A similar observation was true for a group of PGT broadly neutralizing antibodies.

FIG. 9 depicts PGT antibodies binding to BG505 L111A gp140 GCN4L4 trimer. A similar observation was true for a group of PGT broadly neutralizing antibodies.

FIG. 10 depicts a neutralization assay (comparison of BG505 WT and BG505 L111A pseudoviruses). The neutralization assay was done with BG505 WT and L111A pseudoviruses and a panel of human broadly neutralizing antibodies. Most antibodies neutralize both forms of virus to the same extent. That is a clear indication that L111A mutation does not jeopardize fully functional gp160.

Figure 11:
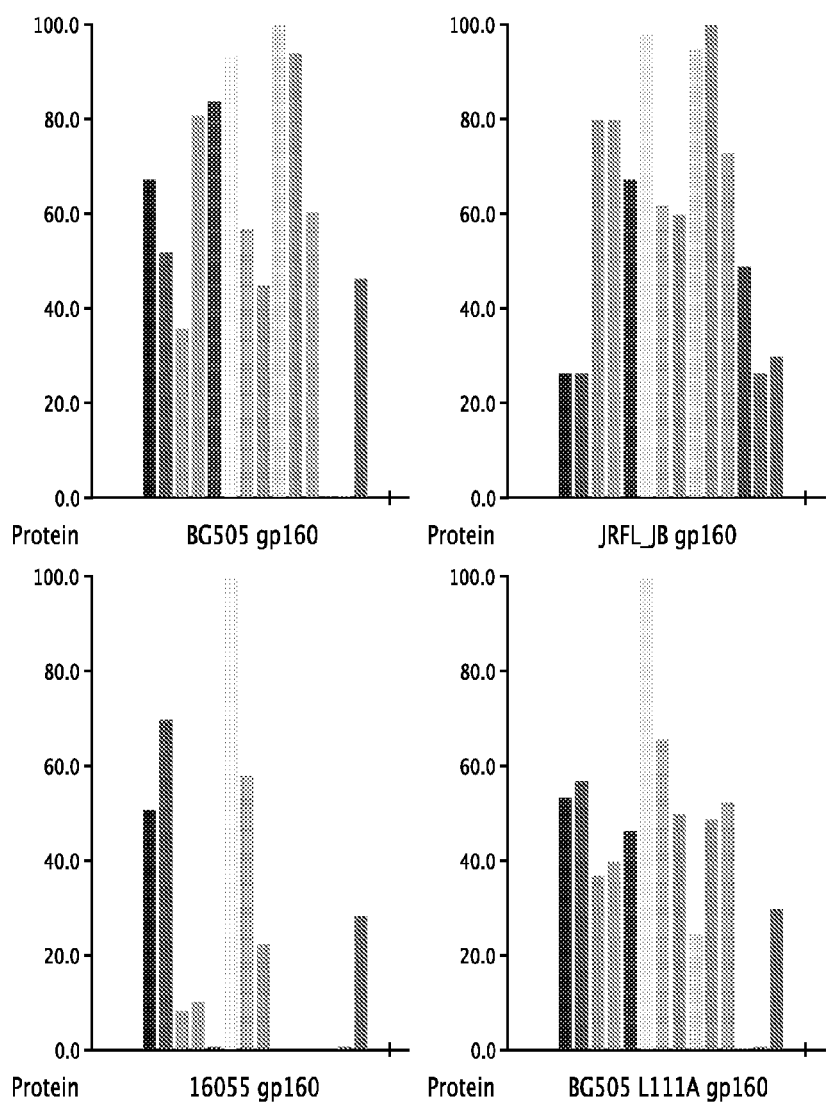

FIG. 11 depicts a Clade and Mutant Specific Binding Profiles by cytofluorimetry Another test for the integrity of gp160 Envelope protein with L111A mutation was done with gp160 expressed in HEK 293T cells by transient transfection with a plasmid DNA. In this study binding of a panel of neutralizing antibodies was measured by using cytofluorimetry (FACS). BG505 had the broadest binding pattern compare to Clade B (JR-FL), and Clade C (16055). Binding pattern to BG505WT and L111A was similar.

Figure 12:
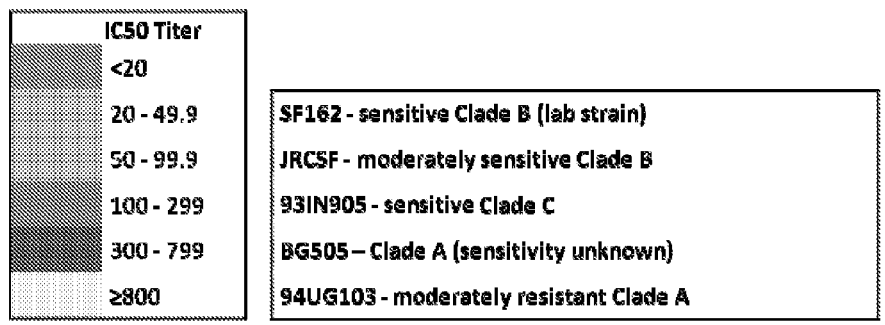
FIG. 12 depicts a Neutralization assay with sera from rabbits immunized with BG505 L111A gp120. This study was done by immunizing rabbits using prime-boost approach. In this experiment Applicants used two DNA immunizations (2× prime) and a protein boost with BG505 L111A gp20. Antisera from the rabbits the experiment was diluted and applied to pseudovirus neutralization assay. The results are reported as IC50 titers. Rabbits that were primed by DNA and boosted by protein developed neutralization activity against Clade A, B and C pseudoviruses.

FIG. 12 depicts a Neutralization assay with sera from rabbits immunized with BG505 L111A gp120. This study was done by immunizing rabbits using prime-boost approach. In this experiment Applicants used two DNA immunizations (2× prime) and a protein boost with BG505 L111A gp120. Antisera from the rabbits the experiment was diluted and applied to pseudovirus neutralization assay. The results are reported as IC50 titers. Rabbits that were primed by DNA and boosted by protein developed neutralization activity against Clade A, B and C pseudoviruses.

The proteins of this Example may be useful for the production of soluble stable recombinant Envelope proteins as components of HIV vaccine, as bait for identification of neutralizing antibodies. The purified proteins of this Example may be useful as an analytical standard for passive immunization with antibodies, to characterize the type of neutralizing antibodies induced by HIV vaccines or for crystallization to identify epitopes for neutralizing antibodies and design of new immunogens. The proteins of this Example may be useful in the design of genetic immunogens (DNA, viral vector) carrying Envelopes with the stabilizing mutation or of Virus-like particles carrying Envelopes with the stabilizing mutation.

Example 3

Stabilizing Mutation BG505 L111A T7332N for HIV Envelope Proteins

The Example relates to methods for improving binding of certain PGT antibodies to a recombinant Clade A HIV Envelope (Env) protein. Mutation T332N that introduces a potential glycosylation site important as a part of epitopes for some PGT antibodies (Walker L M et al. Nature. 2011, 477(7365):466-70 and Pejchal R et al. Science. 2011, 334 (6059):1097-103). The protein was expressed as BG505 L111A T332N gp120. Further analysis of proteins carrying this mutation confirmed that these proteins retain fill antigenicity of the wild type protein, i.e. binding of neutralizing antibodies associated with resistance to HIV. In addition to those antibodies a family of antibodies PGT135 and PGT136 were binding to the mutant protein. Other antibodies, for example PGT121 family, improved their binding properties. Binding to T332N mutant protein does not depend on the cell line used for expression. We used both HEK 293T cells (producing complex oligosaccharides) and HEK 293S cells (highly mannosylated oligosaccharides) with no change of binding properties.

Original wild type sequences were aligned with HxB2 reference strain of HIV Envelope protein. The Threonine in the position corresponding to 332 in HxB2 was replaced by Alanine. Actual mutagenesis was performed by GeneArt (Life Technologies) and DNA was delivered in pCI-Neo or pcDNA plasmid. Clade A BG505 gp120 was made.

Envelope proteins carrying T332N mutation and non-mutated (wild type) versions were produced by DNA transient transfection of HEK 293T or HEK 293S cells. 293T and 293 S cells differ in the type of glycosylation of secreted recombinant proteins. The former producing proteins with complex oligosaccharides, while the latter producing proteins with oligomannose-type glycans.

Proteins secreted to the cell culture media were purified by using affinity chromatography on Galanthus nivalis (snowdrop) lectin (GNL) column.

Antigenicity (antibody binding) was measured with multiple human antibodies isolated from HIV-infected subjects. Methods used to measure antigenicity: ELISA for soluble recombinant Envs captured through His-tags.

FIG. 13 depicts Binding to BG505 L111A gp120. Binding of antibody to BG505 L111A gp120 secreted into cell culture media was measured by Enzyme-linked immunosorbent assay (ELISA) in 96-well microplates. The set of antibodies used to characterize antigenicity included trimer-specific antibodies (PG9, PG16), CD4 binding site (CD4bs) specific antibodies (b6, b12, VRC01, VRC04/PGV04), and PGT series (PGT121-136). Antibodies that demonstrated difference in binding properties are shown in red.

The proteins of this Example may be useful for the production of soluble recombinant Envelope proteins as components of HIV vaccine, as bait for identification of neutralizing antibodies. The purified proteins of this Example may be useful as an analytical standard for passive immunization with antibodies, to characterize the type of neutralizing antibodies induced by HIV vaccines or for crystallization to identify epitopes for neutralizing antibodies and design of new immunogens. The proteins of this Example may be useful in the design of genetic immunogens (DNA, viral vector) or Virus-like particles carrying Envelopes with improved antigenic and immunogenic properties.

The invention is further described by the following numbered paragraphs:

1. An isolated or non-naturally occurring soluble HIV-1 envelope glycoprotein.

2. The glycoprotein of paragraph 1, wherein the glycoprotein is isolated from a HIV-1 Clade A virus, HIV-1 Clade B virus, HIV-1 Clade C virus, a HIV-1 Clade A pseudo-virus, HIV-1 Clade B pseudo-virus or a HIV-1 Clade C pseudo-virus.

3. The glycoprotein of paragraph 1 or 2, wherein the glycoprotein binds a broadly neutralizing antibody.

4. The glycoprotein of paragraph 3, wherein the antibody is PG9 and/or PG16.

5. The glycoprotein of any one of paragraphs 1-4, wherein the soluble envelope glycoproteins of the present invention is isolated from a HIV-1 Clade A virus, HIV-1 Clade B virus, HIV-1 Clade C virus, a HIV-1 Clade A pseudo-virus, HIV-1 Clade B pseudo-virus, a HIV-1 Clade C pseudo-virus, the 6535 virus, the 13095 virus, the 16055 virus, the 25710 virus, the 25925 virus, the CAAN virus or the Zm109F virus.

6. The glycoprotein of any one of paragraphs 1-5, wherein an amino acid sequence of the glycoprotein has a substantially similar consensus sequence to the consensus sequence depicted in FIGS. 2A-2J.

7. A method for screening broad neutralizing antibodies comprising contacting the glycoprotein of any one of paragraphs 1-6 with an animal or human sera, isolating the glycoprotein complexed to the broad neutralizing antibodies, thereby screening for a broad neutralizing antibody.

8. A method for identifying a binding site of a soluble HIV-1 envelope glycoprotein to a broadly neutralizing antibody comprising contacting the glycoprotein of any one of paragraphs 1-6 with a broadly neutralizing antibody, isolating the glycoprotein complexed to the antibody, and determining the crystal structure of the glycoprotein-antibody complex, wherein the crystal structure identifies the binding site of the glycoprotein and the antibody, thereby identifying a binding site of a soluble HIV-1 envelope glycoprotein to a broadly neutralizing antibody.

9. The method of paragraph 6, wherein the antibody is PG9 and/or PG16.

10. A method of producing an immune response comprising administering to a mammal the glycoprotein of any one of paragraphs 1-6.

11. A method of eliciting an immune response comprising administering to a mammal the vector of any one of paragraphs 1-6.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for screening broad neutralizing antibodies comprising contacting a non-naturally occurring soluble HIV-1 envelope glycoprotein isolated from a 16055 virus comprising a L111A, T332N or L111A/T332N mutation(s), wherein said numbering scheme is based upon alignment with HXB2 reference strain of HIV-1 envelope glycoprotein, with an animal or human sera, isolating the glycoprotein complexed to the broad neutralizing antibodies, and testing the activity of the broad neutralizing antibodies in a neutralization assay or a pseudoneutralization assay to determine if the sera is neutralizing, thereby screening for a broad neutralizing antibody.

2. The glycoprotein of claim 1, wherein the mutation is L111A.

3. The glycoprotein of claim 1, wherein the mutation is T332N.

4. The glycoprotein of claim 1, wherein the mutation is L111A/T332N.

5. A method for screening broad neutralizing antibodies comprising contacting a non-naturally occurring soluble HIV-1 envelope glycoprotein isolated from 6535 virus, a 13095 virus, a 25710 virus, a 25925 virus, a CAAN virus or a Zm109F virus comprising a L111A, T332N or L111A/T332N mutation(s), wherein said numbering scheme is based upon alignment with HXB2 reference strain of HIV-1 envelope glycoprotein, with an animal or human sera, isolating the glycoprotein complexed to the broad neutralizing antibodies, and testing the activity of the broad neutralizing antibodies in a neutralization assay or a pseudoneutralization assay to determine if the sera is neutralizing, thereby screening for a broad neutralizing antibody.

6. The glycoprotein of claim 1, wherein the mutation is L111A.

7. The glycoprotein of claim 1, wherein the mutation is T332N.

8. The glycoprotein of claim 1, wherein the mutation is L111A/T332N.

* * * * *

SEQUENCE LISTING

<160> NUMBER OF SEQ ID NOS: 38

<210> SEQ ID NO 1
<211> LENGTH: 471
<212> TYPE: PRT
<213> ORGANISM: Human immunodeficiency virus

<400> SEQUENCE: 1

```
Leu Trp Val Thr Val Tyr Tyr Gly Val Pro Val Trp Lys Glu Ala Lys
1               5                   10                  15

Thr Thr Leu Phe Cys Ala Ser Asp Ala Lys Ala Tyr Glu Lys Glu Val
            20                  25                  30

His Asn Val Trp Ala Thr His Ala Cys Val Pro Thr Asp Pro Asn Pro
        35                  40                  45

Gln Glu Met Val Leu Glu Asn Val Thr Glu Asn Phe Asn Met Trp Glu
    50                  55                  60

Asn Asp Val Val Asp Gln Met His Glu Asp Val Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Ser Lys Ala Lys Asn Ile Thr Glu Glu Val Ile Lys Asn Asn
            100                 105                 110

Thr Tyr Lys Glu Asp Ile Arg Asn Cys Ser Phe Asn Ala Thr Thr Glu
        115                 120                 125

Val Lys Asp Lys Gln Lys Val His Ala Leu Phe Tyr Arg Leu Asp
    130                 135                 140

Ile Val Pro Leu Asn Lys Arg Asn Ser Ser Glu Ser Glu Glu Glu Asn
145                 150                 155                 160

Ser Ser Gly Tyr Tyr Arg Leu Ile Asn Cys Asn Thr Ser Ala Val Thr
                165                 170                 175

Gln Ala Cys Pro Lys Val Thr Phe Asp Pro Ile Pro Ile His Tyr Cys
            180                 185                 190

Thr Pro Ala Gly Tyr Ala Ile Leu Lys Cys Asn Glu Glu Thr Phe Asn
        195                 200                 205

Gly Thr Gly Pro Cys His Asn Val Ser Thr Val Gln Cys Thr His Gly
    210                 215                 220

Ile Lys Pro Val Val Ser Thr Gln Leu Leu Leu Asn Gly Ser Leu Ala
225                 230                 235                 240

Glu Gly Glu Ile Ile Ile Arg Ser Lys Asn Leu Thr Asp Asn Ala Lys
                245                 250                 255

Thr Ile Ile Val His Leu Asn Gln Ser Val Glu Ile Val Cys Thr Arg
            260                 265                 270

Pro Asn Glu Asn Arg Arg Lys Ser Ile Arg Ile Gly Pro Gly Gln Ala
        275                 280                 285

Phe Tyr Ala Thr Gly Asp Ile Ile Gly Asp Ile Arg Gln Ala Arg Cys
    290                 295                 300

Asn Ile Ser Glu Glu Lys Trp Asn Glu Thr Leu Gln Arg Val Gly Arg
305                 310                 315                 320

Lys Leu Ala Glu His Phe Pro Asn Lys Thr Ile Lys Phe Lys Ser Ser
                325                 330                 335

Ser Gly Gly Asp Leu Glu Ile Thr Thr His Ser Phe Asn Cys Arg Gly
            340                 345                 350

Glu Phe Phe Tyr Cys Asn Thr Ser Gly Leu Phe Asn Gly Thr Tyr Met
        355                 360                 365
```

```
Pro Thr Tyr Met Pro Asn Ser Thr Asn Ser Asn Ser Ser Asn Ile
    370             375             380

Thr Ile Pro Cys Arg Ile Lys Gln Val Ile Asn Met Trp Gln Glu Val
385             390             395             400

Gly Arg Ala Met Tyr Ala Pro Pro Ile Glu Gly Glu Ile Thr Cys Lys
                405             410             415

Ser Asn Ile Thr Gly Leu Leu Val Arg Asp Gly Gly Asn Gly Asn
            420             425             430

Asp Thr Asn Lys Thr Glu Ile Phe Arg Pro Gly Gly Asp Met Arg
            435             440             445

Asp Asn Trp Arg Ser Glu Leu Tyr Lys Tyr Lys Val Val Glu Ile Lys
450             455             460

Pro Leu Gly Ile Ala Pro Thr
465             470

<210> SEQ ID NO 2
<211> LENGTH: 459
<212> TYPE: PRT
<213> ORGANISM: Human immunodeficiency virus

<400> SEQUENCE: 2

Leu Trp Val Thr Val Tyr Tyr Gly Val Pro Val Trp Lys Glu Ala Thr
1               5               10              15

Thr Thr Leu Phe Cys Ala Ser Asp Ala Lys Ala Tyr Asp Lys Glu Val
                20              25              30

His Asn Val Trp Ala Thr His Ala Cys Val Pro Thr Asp Pro Asn Pro
            35              40              45

Gln Glu Met Val Leu Gly Asn Val Thr Glu Asn Phe Asn Met Trp Lys
50              55              60

Asn Glu Met Val Asn Gln Met His Glu Asp Val Ile Ser Leu Trp Asp
65              70              75              80

Gln Ser Leu Lys Pro Cys Val Lys Leu Thr Pro Leu Cys Val Thr Leu
                85              90              95

Glu Cys Ser Asn Val Thr Tyr Asn Glu Ser Met Lys Glu Val Lys Asn
                100             105             110

Cys Ser Phe Asn Leu Thr Thr Glu Leu Arg Asp Lys Lys Gln Lys Val
            115             120             125

His Ala Leu Phe Tyr Arg Leu Asp Ile Val Pro Leu Asn Asp Thr Glu
    130             135             140

Lys Lys Asn Ser Ser Arg Pro Tyr Arg Leu Ile Asn Cys Asn Thr Ser
145             150             155             160

Ala Ile Thr Gln Ala Cys Pro Lys Val Thr Phe Asp Pro Ile Pro Ile
                165             170             175

His Tyr Cys Thr Pro Ala Gly Tyr Ala Ile Leu Lys Cys Asn Asp Lys
            180             185             190

Lys Phe Asn Gly Thr Gly Pro Cys His Lys Val Ser Thr Val Gln Cys
        195             200             205

Thr His Gly Ile Lys Pro Val Val Ser Thr Gln Leu Leu Leu Asn Gly
    210             215             220

Ser Leu Ala Glu Gly Glu Ile Ile Ile Arg Ser Glu Asn Leu Thr Asn
225             230             235             240

Asn Ala Lys Thr Ile Ile Val His Leu Asn Gln Ser Val Glu Ile Val
                245             250             255

Cys Ala Arg Pro Ser Asn Asn Thr Arg Thr Ser Ile Arg Ile Gly Pro
            260             265             270
```

-continued

```
Gly Gln Thr Phe Tyr Ala Thr Gly Ala Ile Thr Gly Asp Ile Arg Gln
            275                 280                 285

Ala His Cys Asn Ile Ser Lys Asp Lys Trp Asn Glu Thr Leu Gln Arg
290                 295                 300

Val Gly Glu Lys Leu Ala Glu His Phe Pro Asn Lys Thr Ile Lys Phe
305                 310                 315                 320

Asn Ser Ser Gly Gly Asp Leu Glu Ile Thr Thr His Ser Phe Asn
                325                 330                 335

Cys Arg Gly Glu Phe Phe Tyr Cys Asn Thr Ser Gly Leu Phe Asn Gly
                340                 345                 350

Thr Phe Asn Gly Thr Tyr Val Ser Pro Asn Ser Thr Asp Ser Asn Ser
            355                 360                 365

Ser Ser Ile Ile Thr Ile Pro Cys Arg Ile Lys Gln Ile Ile Asn Met
            370                 375                 380

Trp Gln Glu Val Gly Arg Ala Met Tyr Ala Pro Pro Ile Ala Gly Asn
385                 390                 395                 400

Ile Thr Cys Lys Ser Asn Ile Thr Gly Leu Leu Leu Val Arg Asp Gly
                405                 410                 415

Gly Thr Gly Ser Glu Ser Asn Lys Thr Glu Ile Phe Arg Pro Gly Gly
            420                 425                 430

Gly Asp Met Arg Asp Asn Trp Arg Ser Glu Leu Tyr Lys Tyr Lys Val
            435                 440                 445

Val Glu Ile Lys Pro Leu Gly Val Ala Pro Thr
450                 455

<210> SEQ ID NO 3
<211> LENGTH: 472
<212> TYPE: PRT
<213> ORGANISM: Human immunodeficiency virus

<400> SEQUENCE: 3

Leu Trp Val Thr Val Tyr Tyr Gly Val Pro Val Trp Lys Glu Ala Lys
1               5                   10                  15

Ala Thr Leu Phe Cys Ala Ser Asp Ala Lys Ala Tyr Glu Thr Glu Val
            20                  25                  30

His Asn Val Trp Ala Thr His Ala Cys Val Pro Thr Asp Pro Asn Pro
        35                  40                  45

Gln Glu Ile Val Leu Glu Asn Val Thr Glu Asn Phe Asn Met Trp Glu
    50                  55                  60

Asn Asp Met Val Asn Gln Met His Glu Asp Val Ile Ser Leu Trp Asp
65                  70                  75                  80

Gln Ser Leu Lys Pro Cys Val Lys Leu Thr Pro Leu Cys Val Thr Leu
                85                  90                  95

Asp Cys Glu Asn Val Asp Gly Asn Asp Thr Tyr Asn Gly Thr Asn Glu
            100                 105                 110

Met Lys Asn Cys Ser Phe Asn Thr Thr Glu Leu Arg Asp Lys Lys
        115                 120                 125

Gln Lys Val Ser Ala Leu Phe Tyr Arg Leu Asp Ile Val Pro Leu Asn
    130                 135                 140

Arg Ser Ser Ser Asn Ser Ser Asp Tyr Tyr Arg Leu Ile Ser Cys
145                 150                 155                 160

Asn Thr Ser Ala Ile Thr Gln Ala Cys Pro Lys Val Thr Phe Asp Pro
                165                 170                 175

Ile Pro Ile His Tyr Cys Ala Pro Ala Gly Phe Ala Ile Leu Lys Cys
```

```
            180                 185                 190
Asn Asn Lys Thr Phe Asn Gly Thr Gly Pro Cys His Asn Val Ser Thr
            195                 200                 205

Val Gln Cys Thr His Gly Ile Lys Pro Val Val Ser Thr Gln Leu Leu
            210                 215                 220

Leu Asn Gly Ser Leu Ala Glu Lys Glu Ile Ile Arg Ser Lys Asn
225                 230                 235                 240

Leu Ser Asp Asn Val Lys Thr Ile Ile Val His Leu Asn Glu Ser Val
                    245                 250                 255

Glu Ile Val Cys Thr Arg Pro Asn Asn Asn Thr Arg Lys Ser Ile Arg
                260                 265                 270

Ile Gly Pro Gly Gln Thr Phe Tyr Ala Thr Gly Ala Ile Ile Gly Asn
            275                 280                 285

Ile Arg Glu Ala His Cys Asn Ile Ser Arg Asp Lys Trp Asn Glu Thr
            290                 295                 300

Leu Gln Arg Val Gly Lys Lys Leu Glu Glu Gln Phe Pro Asn Lys Thr
305                 310                 315                 320

Ile Asn Phe Thr Ser Ser Gly Gly Asp Leu Glu Ile Thr Thr His
                    325                 330                 335

Ser Phe Asn Cys Arg Gly Glu Phe Phe Tyr Cys Asn Thr Ser Lys Leu
                340                 345                 350

Phe Asn Ser Thr Tyr Ile Pro Thr Tyr Arg Pro Asn Asn Thr Gln Gly
            355                 360                 365

Asn Ser Ser Ser Thr Ile Thr Ile Pro Cys Arg Ile Lys Gln Ile Ile
            370                 375                 380

Asn Met Trp Gln Glu Val Gly Arg Ala Met Tyr Ala Pro Pro Ile Ala
385                 390                 395                 400

Gly Asn Ile Thr Cys Lys Ser His Ile Thr Gly Leu Leu Leu Val Arg
                    405                 410                 415

Asp Gly Gly Thr Gly Leu Asn Ser Ser Thr Glu Thr Phe Arg Pro Gly
                420                 425                 430

Gly Gly Asp Met Arg Asp Asn Trp Arg Ser Glu Leu Tyr Lys Tyr Lys
            435                 440                 445

Val Val Glu Ile Lys Pro Leu Gly Val Ala Pro Thr Ala Ala Lys Arg
            450                 455                 460

Arg Val Val Gln Arg Glu Lys Arg
465                 470

<210> SEQ ID NO 4
<211> LENGTH: 456
<212> TYPE: PRT
<213> ORGANISM: Human immunodeficiency virus

<400> SEQUENCE: 4

Leu Trp Val Thr Val Tyr Tyr Gly Val Pro Val Trp Lys Glu Ala Lys
1               5                   10                  15

Thr Thr Leu Phe Cys Ala Ser Asp Ala Lys Ala His Glu Arg Glu Val
                20                  25                  30

His Asn Val Trp Ala Thr Tyr Ala Cys Val Pro Thr Asp Pro Asn Pro
            35                  40                  45

Gln Glu Ile Val Leu Lys Asn Val Thr Glu Asn Phe Asn Met Trp Glu
        50                  55                  60

Asn Asp Met Val Asp Gln Met Gln Glu Asp Val Ile Ser Leu Trp Asp
65                  70                  75                  80
```

Gln Ser Leu Lys Pro Cys Ile Lys Leu Thr Pro Leu Cys Val Thr Leu
                85                  90                  95

Glu Cys Thr Asn Val Asn Ile Ile Asn Gly Thr Ile His Asn Glu Thr
            100                 105                 110

Tyr Glu Ser Met Lys Asn Cys Ser Phe Asn Thr Thr Glu Leu Lys
        115                 120                 125

Asp Lys Lys Gln Ser Val Tyr Ala Leu Phe Tyr Arg Leu Asp Ile Val
        130                 135                 140

Pro Leu Asn Asn Ser Asn Glu Tyr Tyr Arg Leu Ile Asn Cys Asn Thr
145                 150                 155                 160

Ser Ala Ile Lys Gln Ala Cys Pro Lys Val Thr Phe Asp Pro Ile Pro
                165                 170                 175

Ile His Tyr Cys Ala Pro Ala Gly Tyr Ala Ile Leu Lys Cys Asn Asp
            180                 185                 190

Lys Thr Phe Ser Gly Thr Gly Pro Cys His Asn Val Ser Thr Val Gln
        195                 200                 205

Cys Thr His Gly Ile Lys Pro Val Val Ser Thr Gln Leu Leu Leu Asn
        210                 215                 220

Gly Ser Leu Ala Glu Gly Glu Ile Ile Ile Arg Ser Lys Lys Leu Asp
225                 230                 235                 240

Asp Asn Ala Asn Thr Ile Ile Val His Leu Asp Glu Pro Val Lys Ile
                245                 250                 255

Glu Cys Thr Arg Pro Asn Asn Asn Thr Arg Lys Ser Ile Arg Ile Gly
            260                 265                 270

Pro Gly Gln Thr Phe Tyr Ala Thr Gly Glu Ile Gly Asn Ile Arg
        275                 280                 285

Gln Ala His Cys Asp Ile Ser Glu Asp Gln Trp Asn Glu Thr Leu Gln
        290                 295                 300

Arg Val Gly Lys Lys Leu Ala Glu Leu Phe Pro Asn Lys Thr Ile Thr
305                 310                 315                 320

Phe Asn Ser Ser Ser Gly Gly Asp Leu Glu Ile Thr Thr His Ser Phe
                325                 330                 335

Asn Cys Arg Gly Glu Phe Phe Tyr Cys Asn Thr Ser Ser Leu Phe Lys
            340                 345                 350

Gly Thr Tyr Arg Pro Asn Gly Thr Ser Asn Ser Thr Ser Gly Ser Ile
        355                 360                 365

Ile Thr Leu Pro Cys Tyr Ile Lys Gln Val Ile Asn Leu Trp Gln Glu
        370                 375                 380

Val Gly Arg Ala Ile Tyr Ala Pro Pro Ile Glu Gly Asn Ile Thr Cys
385                 390                 395                 400

Ile Ser Asn Ile Thr Gly Leu Leu Leu Val Arg Asp Gly Gly Asn His
                405                 410                 415

Glu Glu Ala Asn Thr Thr Glu Thr Phe Arg Pro Gly Gly Gly Asn Met
            420                 425                 430

Arg Asp Asn Trp Arg Ser Glu Leu Tyr Lys Tyr Lys Val Val Glu Ile
        435                 440                 445

Lys Pro Leu Gly Val Ala Pro Thr
        450                 455

<210> SEQ ID NO 5
<211> LENGTH: 464
<212> TYPE: PRT
<213> ORGANISM: Human immunodeficiency virus

<400> SEQUENCE: 5

-continued

```
Leu Trp Val Thr Val Tyr Tyr Gly Val Pro Val Trp Lys Glu Ala Lys
1               5                   10                  15

Thr Thr Leu Phe Cys Ala Ser Asp Ala Lys Ala Tyr Glu Lys Glu Val
                20                  25                  30

His Asn Val Trp Ala Thr His Ala Cys Val Pro Thr Asp Pro Asn Pro
            35                  40                  45

Gln Glu Met Val Leu Glu Asn Val Thr Glu Asn Phe Asn Met Trp Lys
        50                  55                  60

Asn Asp Met Val Glu Gln Met His Glu Asp Val Ile Ser Leu Trp Asp
65                  70                  75                  80

Gln Ser Leu Lys Pro Cys Val Lys Leu Thr Pro Leu Cys Val Thr Leu
                85                  90                  95

Glu Cys Arg Gln Val Asn Thr Thr Asn Ala Thr Ser Ser Val Asn Val
            100                 105                 110

Thr Asn Gly Glu Glu Ile Lys Asn Cys Ser Phe Asn Ala Thr Thr Glu
        115                 120                 125

Ile Arg Asp Lys Lys Gln Lys Val Tyr Ala Leu Phe Tyr Arg Leu Asp
        130                 135                 140

Ile Val Pro Leu Glu Glu Arg Lys Gly Asn Ser Ser Lys Tyr Arg
145                 150                 155                 160

Leu Ile Asn Cys Asn Thr Ser Ala Ile Thr Gln Ala Cys Pro Lys Val
                165                 170                 175

Thr Phe Asp Pro Ile Pro Ile His Tyr Cys Ala Pro Ala Gly Tyr Ala
            180                 185                 190

Ile Leu Lys Cys Asn Asn Lys Thr Phe Asn Gly Thr Gly Pro Cys Asn
        195                 200                 205

Asn Val Ser Thr Val Gln Cys Thr His Gly Ile Lys Pro Val Val Ser
210                 215                 220

Thr Gln Leu Leu Leu Asn Gly Ser Leu Ala Glu Gly Glu Ile Ile Ile
225                 230                 235                 240

Arg Ser Glu Asn Leu Thr Asn Asn Val Lys Thr Ile Ile Val His Leu
                245                 250                 255

Asn Glu Ser Val Glu Ile Val Cys Thr Arg Pro Asn Asn Asn Thr Arg
            260                 265                 270

Lys Ser Ile Arg Ile Gly Pro Gly Gln Thr Phe Tyr Ala Thr Gly Asp
        275                 280                 285

Ile Ile Gly Asn Ile Arg Gln Ala Tyr Cys Asn Ile Lys Lys Asp Asp
290                 295                 300

Trp Ile Arg Thr Leu Gln Arg Val Gly Lys Lys Leu Ala Glu His Phe
305                 310                 315                 320

Pro Arg Arg Ile Ile Asn Phe Thr Ser Pro Ala Gly Gly Asp Leu Glu
                325                 330                 335

Ile Thr Thr His Ser Phe Asn Cys Arg Gly Glu Phe Phe Tyr Cys Asn
            340                 345                 350

Thr Ser Ser Leu Phe Asn Ser Thr Tyr Asn Pro Asn Asp Thr Asn Ser
        355                 360                 365

Asn Ser Ser Ser Ser Asn Ser Ser Leu Asp Ile Thr Ile Pro Cys Arg
370                 375                 380

Ile Lys Gln Ile Ile Asn Met Trp Gln Glu Val Gly Arg Ala Met Tyr
385                 390                 395                 400

Ala Pro Pro Ile Glu Gly Asn Ile Thr Cys Lys Ser Asn Ile Thr Gly
                405                 410                 415
```

```
Leu Leu Leu Val Arg Asp Gly Gly Val Glu Ser Asn Glu Thr Glu Ile
            420                 425                 430

Phe Arg Pro Gly Gly Gly Asp Met Arg Asn Asn Trp Arg Ser Glu Leu
            435                 440                 445

Tyr Lys Tyr Lys Val Val Glu Ile Lys Pro Leu Gly Ile Ala Pro Thr
450                 455                 460

<210> SEQ ID NO 6
<211> LENGTH: 469
<212> TYPE: PRT
<213> ORGANISM: Human immunodeficiency virus

<400> SEQUENCE: 6

Leu Trp Val Thr Val Tyr Tyr Gly Val Pro Val Trp Lys Glu Ala Arg
1               5                   10                  15

Thr Thr Leu Phe Cys Ala Ser Asp Ala Lys Ala Tyr Glu Thr Glu Val
            20                  25                  30

His Asn Val Trp Ala Thr His Ala Cys Val Pro Thr Asp Pro Asn Pro
        35                  40                  45

Gln Glu Met Val Leu Gly Asn Val Thr Glu Asn Phe Asn Met Trp Lys
    50                  55                  60

Asn Asp Met Val Asp Gln Met His Glu Asp Val Ile Ser Leu Trp Ala
65                  70                  75                  80

Gln Ser Leu Lys Pro Cys Val Lys Leu Thr Pro Leu Cys Val Thr Leu
                85                  90                  95

Glu Cys Thr Gln Val Asn Ala Thr Gln Gly Asn Thr Thr Gln Val Asn
            100                 105                 110

Val Thr Gln Val Asn Gly Asp Glu Met Lys Asn Cys Ser Phe Asn Thr
        115                 120                 125

Thr Thr Glu Ile Arg Asp Lys Lys Gln Lys Ala Tyr Ala Leu Phe Tyr
    130                 135                 140

Arg Leu Asp Leu Val Pro Leu Glu Arg Glu Asn Arg Gly Asp Ser Asn
145                 150                 155                 160

Ser Ala Ser Lys Tyr Ile Leu Ile Asn Cys Asn Thr Ser Ala Ile Thr
                165                 170                 175

Gln Ala Cys Pro Lys Val Asn Phe Asp Pro Ile Pro Ile His Tyr Cys
            180                 185                 190

Thr Pro Ala Gly Tyr Ala Ile Leu Lys Cys Asn Asn Lys Thr Phe Asn
        195                 200                 205

Gly Thr Gly Ser Cys Asn Asn Val Ser Thr Val Gln Cys Thr His Gly
    210                 215                 220

Ile Lys Pro Val Val Ser Thr Gln Leu Leu Leu Asn Gly Ser Leu Ala
225                 230                 235                 240

Glu Glu Glu Ile Ile Ile Arg Ser Glu Asn Leu Thr Asp Asn Val Lys
                245                 250                 255

Thr Ile Ile Val His Leu Asp Gln Ser Val Glu Ile Val Cys Thr Arg
            260                 265                 270

Pro Asn Asn Asn Thr Arg Lys Ser Ile Arg Ile Gly Pro Gly Gln Thr
        275                 280                 285

Phe Tyr Ala Thr Gly Asp Ile Ile Gly Asn Ile Arg Glu Ala His Cys
    290                 295                 300

Asn Ile Ser Glu Lys Lys Trp His Glu Met Leu Arg Arg Val Ser Glu
305                 310                 315                 320

Lys Leu Ala Glu His Phe Pro Asn Lys Thr Ile Lys Phe Thr Ser Ser
                325                 330                 335
```

```
Ser Gly Gly Asp Leu Glu Ile Thr Thr His Ser Phe Asn Cys Arg Gly
            340                 345                 350

Glu Phe Phe Tyr Cys Asn Thr Ser Gly Leu Phe Asn Ser Thr Tyr Met
        355                 360                 365

Pro Asn Gly Thr Tyr Met Pro Asn Gly Thr Asn Ser Asn Ser Thr
370                 375                 380

Ile Ile Leu Pro Cys Arg Ile Lys Gln Ile Ile Asn Met Trp Gln Glu
385                 390                 395                 400

Val Gly Arg Ala Met Tyr Ala Pro Pro Ile Ala Gly Asn Ile Thr Cys
                405                 410                 415

Asn Ser Asn Ile Thr Gly Leu Leu Leu Val Arg Asp Gly Gly Lys Asn
            420                 425                 430

Asn Asn Thr Glu Ile Phe Arg Pro Gly Gly Gly Asp Met Arg Asp Asn
        435                 440                 445

Trp Arg Ser Glu Leu Tyr Lys Tyr Lys Val Val Glu Ile Lys Pro Leu
    450                 455                 460

Gly Val Ala Pro Thr
465

<210> SEQ ID NO 7
<211> LENGTH: 456
<212> TYPE: PRT
<213> ORGANISM: Human immunodeficiency virus

<400> SEQUENCE: 7

Leu Trp Val Thr Val Tyr Tyr Gly Val Pro Val Trp Lys Glu Ala Lys
1               5                  10                  15

Thr Thr Leu Phe Cys Ala Ser Asp Ala Lys Ala Tyr Glu Thr Glu Val
            20                  25                  30

His Asn Val Trp Ala Thr His Ala Cys Val Pro Thr Asp Pro Asn Pro
        35                  40                  45

Gln Glu Leu Val Leu Glu Asn Val Thr Glu Asn Phe Asn Met Trp Arg
    50                  55                  60

Asn Asp Met Val Asp Gln Met His Glu Asp Val Ile Ser Leu Trp Asp
65                  70                  75                  80

Gln Ser Leu Lys Pro Cys Val Lys Leu Thr Pro Leu Cys Val Thr Leu
                85                  90                  95

Glu Cys Arg Asn Ala Thr Ser Lys Met Val Asn Asp Thr Arg Asn Val
            100                 105                 110

Glu Glu Met Lys Asn Cys Ser Phe Asn Thr Thr Thr Glu Leu Arg Asp
        115                 120                 125

Arg Lys Gln Thr Val Tyr Ala Ser Phe Tyr Lys Leu Asp Ile Val Pro
    130                 135                 140

Leu Asn Glu Asn Lys Ser Thr Ser Ser Glu Asn Tyr Arg Leu Ile Asn
145                 150                 155                 160

Cys Asn Thr Ser Ala Ile Thr Gln Ala Cys Pro Lys Val Asn Phe Asp
                165                 170                 175

Pro Ile Pro Ile His Tyr Cys Thr Pro Ala Gly Tyr Ala Ile Leu Lys
            180                 185                 190

Cys Asn Asn Lys Thr Phe Asn Gly Thr Gly Pro Cys Ser Asn Val Ser
        195                 200                 205

Thr Val Gln Cys Thr His Gly Ile Lys Pro Val Val Ser Thr Gln Leu
    210                 215                 220

Leu Leu Asn Gly Ser Leu Ala Glu Glu Gly Ile Ile Ile Arg Ser Glu
```

```
                225                 230                 235                 240
Asn Leu Thr Asp Asn Val Lys Thr Ile Ile Val His Leu Glu Glu Pro
            245                 250                 255
Val Glu Ile Val Cys Thr Arg Pro Asn Asn Asn Thr Arg Lys Ser Val
            260                 265                 270
Arg Ile Gly Pro Gly Gln Thr Phe Tyr Ala Thr Gly Glu Ile Ile Gly
            275                 280                 285
Asp Ile Arg Gln Ala His Cys Asn Ile Ser Glu Ala Lys Trp Asn Glu
        290                 295                 300
Thr Leu Gln Asn Val Thr Lys Lys Leu Lys Glu His Phe Pro Asn Lys
305                 310                 315                 320
Thr Ile Ile Phe Asn Ser Ser Gly Gly Asp Leu Glu Ile Thr Thr
                325                 330                 335
His Ser Phe Asn Cys Arg Gly Glu Phe Phe Tyr Cys Asn Thr Ser Lys
            340                 345                 350
Leu Phe Asn Gly Ile Tyr Asn Gly Thr Gln Ser Asn Ser Ser Asn Ser
            355                 360                 365
Asn Ser Thr Ile Ile Ile Pro Cys Lys Ile Lys Gln Ile Val Asn Met
        370                 375                 380
Trp Gln Lys Val Gly Arg Ala Met Tyr Ala Pro Pro Ile Ala Gly Asn
385                 390                 395                 400
Ile Thr Cys Thr Ser Asn Ile Thr Gly Leu Leu Leu Val Arg Asp Gly
                405                 410                 415
Gly Pro Asp Asn Val Thr Glu Ile Phe Arg Pro Gly Gly Gly Asp Met
            420                 425                 430
Arg Asp Asn Trp Arg Ser Glu Leu Tyr Lys Tyr Lys Val Val Glu Ile
            435                 440                 445
Lys Pro Leu Gly Ile Ala Pro Thr
        450                 455

<210> SEQ ID NO 8
<211> LENGTH: 489
<212> TYPE: PRT
<213> ORGANISM: Human immunodeficiency virus

<400> SEQUENCE: 8

Leu Trp Val Thr Val Tyr Tyr Gly Val Pro Val Trp Arg Glu Ala Lys
1               5                   10                  15
Thr Thr Leu Phe Cys Ala Ser Asp Ala Lys Ala Tyr Glu Lys Glu Val
                20                  25                  30
His Asn Val Trp Ala Thr His Ala Cys Val Pro Thr Asp Pro Asn Pro
            35                  40                  45
Gln Glu Ile Asp Leu Asn Val Thr Glu Asn Phe Asn Met Trp Lys Asn
        50                  55                  60
Asp Met Val Glu Gln Met His Glu Asp Val Ile Ser Leu Trp Asp Gln
65                  70                  75                  80
Ser Leu Lys Pro Cys Val Lys Leu Thr Pro Ile Cys Val Thr Leu Glu
                85                  90                  95
Cys Thr Asp Ala Asn Ile Thr Cys Asn Ser Thr Thr Ser Ser Asn Asn
                100                 105                 110
Cys Thr Ser Tyr Glu Ile Asn Lys Glu Asp Met Gly Glu Ile Lys Asn
            115                 120                 125
Cys Ser Phe Asn Thr Thr Thr Glu Leu Ile Asp Lys Gln Lys Lys Val
        130                 135                 140
```

```
His Ala Leu Phe Tyr Arg Leu Asp Ile Val Ser Leu Glu Lys Asp Asn
145                 150                 155                 160

Ser Ser Lys Lys Asn Asp Ser Asn Glu Tyr Tyr Arg Leu Ile Asn Cys
                165                 170                 175

Asn Thr Ser Ala Ile Thr Gln Ala Cys Pro Lys Val Thr Phe Asp Pro
            180                 185                 190

Ile Pro Ile His Tyr Cys Ala Pro Ala Gly Tyr Ala Ile Leu Lys Cys
        195                 200                 205

Lys Asn Lys Thr Phe Asn Gly Thr Gly Pro Cys Asn Asn Val Ser Thr
    210                 215                 220

Val Gln Cys Thr His Gly Ile Lys Pro Val Val Ser Thr Gln Leu Leu
225                 230                 235                 240

Leu Asn Gly Ser Leu Ala Glu Glu Ile Ile Ile Arg Ser Glu Asn
                245                 250                 255

Leu Thr Asn Asn Ala Lys Ile Ile Val His Leu Asn Gln Ala Val
        260                 265                 270

Glu Ile Val Cys Thr Arg Pro Gly Asn Asn Thr Arg Lys Ser Ile Arg
            275                 280                 285

Ile Gly Pro Gly Gln Thr Phe Tyr Ala Thr Gly Asp Ile Ile Gly Asp
290                 295                 300

Ile Arg Gln Ala His Cys Asn Ile Ser Glu Ala Lys Trp Asn Lys Thr
305                 310                 315                 320

Leu Arg Glu Val Ser Lys Lys Leu Ala Glu His Phe Pro Asn Lys Thr
                325                 330                 335

Ile Ile Phe Asn Ser Ser Ser Gly Gly Asp Leu Glu Ile Thr Thr His
            340                 345                 350

Ser Phe Asn Cys Gly Gly Glu Phe Phe Tyr Cys Asn Thr Ser Ser Leu
        355                 360                 365

Phe Asn Ser Thr Phe Asn Ser Thr Tyr Met Thr Asn Asp Thr Asp Met
    370                 375                 380

Asn Ser Asn Ser Thr Ile Ser Ile Pro Cys Arg Ile Lys Gln Ile Ile
385                 390                 395                 400

Asn Met Trp Gln Glu Val Gly Arg Ala Met Tyr Ala Pro Pro Ile Ala
                405                 410                 415

Gly Asn Ile Thr Cys Lys Ser Asn Ile Thr Gly Leu Leu Leu Val Arg
            420                 425                 430

Asp Gly Gly Asn Ser Asn Asp Thr Asn Glu Pro Glu Ile Phe Arg Pro
        435                 440                 445

Gln Gly Gly Asp Met Arg Asp Asn Trp Arg Ser Glu Leu Tyr Lys Tyr
    450                 455                 460

Lys Val Val Glu Ile Lys Pro Leu Gly Val Ala Pro Thr Ala Ala Lys
465                 470                 475                 480

Arg Arg Val Val Gly Arg Glu Lys Arg
                485

<210> SEQ ID NO 9
<211> LENGTH: 463
<212> TYPE: PRT
<213> ORGANISM: Human immunodeficiency virus

<400> SEQUENCE: 9

Leu Trp Val Thr Val Tyr Tyr Gly Val Pro Val Trp Lys Glu Ala Lys
1               5                   10                  15

Thr Thr Leu Phe Cys Ala Ser Asp Ala Lys Ala Tyr Glu Lys Glu Val
            20                  25                  30
```

```
His Asn Val Trp Ala Thr His Ala Cys Val Pro Thr Asp Pro Asn Pro
        35                  40                  45

Gln Glu Ile Val Leu Gly Asn Val Thr Glu Asp Phe Asn Met Trp Lys
 50                  55                  60

Asn Asp Met Val Asp Gln Met His Glu Asp Val Ile Ser Leu Trp Asp
 65                  70                  75                  80

Gln Ser Leu Lys Pro Cys Val Lys Leu Thr Pro Leu Cys Val Thr Leu
                 85                  90                  95

Asp Cys Ala Asn Val Thr Ser Asn Ile Thr Asn Gly Glu Glu Ile Lys
                100                 105                 110

Asn Cys Ser Phe Asn Ala Thr Thr Asp Val Arg Asp Lys Lys Lys Thr
             115                 120                 125

Val Tyr Ser Leu Phe Tyr Arg Leu Asp Ile Val Gln Leu Asp Gly Arg
 130                 135                 140

Ser Asn Thr Ser Asn Tyr Arg Leu Ile Asn Cys Asn Thr Ser Thr Ile
145                 150                 155                 160

Thr Gln Ala Cys Pro Lys Val Ser Phe Asp Pro Ile Pro Ile His Tyr
                 165                 170                 175

Cys Ala Pro Ala Gly Tyr Ala Ile Leu Lys Cys Asn Asn Lys Thr Phe
             180                 185                 190

Asn Gly Lys Gly Pro Cys His Asn Ile Ser Thr Val Gln Cys Thr His
             195                 200                 205

Gly Ile Lys Pro Val Val Ser Thr Gln Leu Leu Leu Asn Gly Ser Leu
 210                 215                 220

Ala Glu Glu Glu Ile Ile Arg Ser Glu Asn Leu Thr Asn Asn Val
225                 230                 235                 240

Lys Thr Ile Ile Val His Leu Asn Lys Pro Val Lys Ile Val Cys Thr
                 245                 250                 255

Arg Pro Gly Asn Asn Thr Arg Lys Ser Ile Arg Ile Gly Pro Gly Gln
             260                 265                 270

Thr Phe Tyr Ala Thr Gly Glu Ile Ile Gly Asn Ile Arg Gln Ala His
     275                 280                 285

Cys Asn Ile Ser Lys Glu Glu Trp Asn Lys Thr Leu Gln Gly Val Gly
 290                 295                 300

Glu Lys Leu Ala Glu His Phe Pro Asn Lys Thr Ile Glu Phe Thr Ser
305                 310                 315                 320

Pro Ser Gly Gly Asp Leu Glu Ile Thr Thr His Ser Phe Asn Cys Arg
                 325                 330                 335

Gly Glu Phe Phe Tyr Cys Asn Thr Ser Asp Leu Phe Asn Gly Ile Tyr
             340                 345                 350

Asn Gly Thr Tyr Ile Pro Lys Gly Asn Leu Asn Ser Thr Ile Thr Ile
             355                 360                 365

Gln Cys Lys Ile Lys Gln Phe Ile Asn Met Trp Gln Glu Val Gly Arg
 370                 375                 380

Ala Met Tyr Ala Pro Pro Ile Gln Gly Asn Ile Thr Cys Glu Ser Asn
385                 390                 395                 400

Ile Thr Gly Leu Leu Leu Val Arg Asp Gly Gly Asn Ser Asn Ser Thr
                 405                 410                 415

Glu Glu Ile Phe Arg Pro Gly Gly Gly Asp Met Arg Asp Asn Trp Arg
             420                 425                 430

Ser Glu Leu Tyr Lys Tyr Lys Val Val Glu Ile Lys Pro Leu Gly Val
             435                 440                 445
```

```
Ala Pro Thr Asp Ala Lys Arg Arg Val Val Glu Arg Gly Lys Arg
    450                 455                 460
```

<210> SEQ ID NO 10
<211> LENGTH: 446
<212> TYPE: PRT
<213> ORGANISM: Human immunodeficiency virus
<400> SEQUENCE: 10

```
Leu Trp Val Thr Val Tyr Tyr Gly Val Pro Val Trp Arg Glu Ala Lys
1               5                   10                  15

Thr Thr Leu Phe Cys Ala Ser Asp Ala Lys Ala Tyr Glu Arg Glu Val
            20                  25                  30

His Asn Val Trp Ala Thr His Ala Cys Val Pro Thr Asp Pro Asn Pro
        35                  40                  45

Gln Glu Met Val Leu Glu Asn Val Thr Glu Asn Phe Asn Met Trp Lys
    50                  55                  60

Asn Asp Met Val Asp Gln Met Gln Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Ser Lys Leu Asn Asn Ala Thr Asp Gly Glu Met Lys Asn Cys
            100                 105                 110

Ser Phe Asn Ala Thr Thr Glu Leu Arg Asp Lys Lys Lys Gln Val Tyr
        115                 120                 125

Ala Leu Phe Tyr Lys Leu Asp Ile Val Pro Leu Asp Gly Arg Asn Asn
    130                 135                 140

Ser Ser Glu Tyr Arg Leu Ile Asn Cys Asn Thr Ser Thr Ile Thr Gln
145                 150                 155                 160

Ala Cys Pro Lys Val Ser Phe Asp Pro Ile Pro Ile His Tyr Cys Ala
                165                 170                 175

Pro Ala Gly Tyr Ala Ile Leu Lys Cys Asn Asn Lys Thr Phe Asn Gly
            180                 185                 190

Thr Gly Pro Cys His Asn Val Ser Thr Val Gln Cys Thr His Gly Ile
        195                 200                 205

Lys Pro Val Ile Ser Thr Gln Leu Leu Leu Asn Gly Ser Thr Ala Glu
    210                 215                 220

Glu Asp Ile Ile Ile Arg Ser Glu Asn Leu Thr Asn Asn Ala Lys Thr
225                 230                 235                 240

Ile Ile Val His Leu Asn Glu Ser Ile Glu Ile Glu Cys Thr Arg Pro
                245                 250                 255

Gly Asn Asn Thr Arg Lys Ser Ile Arg Ile Gly Pro Gly Gln Ala Phe
            260                 265                 270

Phe Ala Thr Thr Asn Ile Ile Gly Asp Ile Arg Gln Ala Tyr Cys Ile
        275                 280                 285

Ile Asn Lys Ala Asn Trp Thr Asn Thr Leu His Arg Val Ser Lys Lys
    290                 295                 300

Leu Glu Glu His Phe Pro Asn Lys Thr Ile Asn Phe Asn Ser Ser Ser
305                 310                 315                 320

Gly Gly Asp Leu Glu Ile Thr Thr His Ser Phe Asn Cys Gly Gly Glu
                325                 330                 335

Phe Phe Tyr Cys Asn Thr Ser Ser Leu Phe Asn Gly Thr Tyr Asn Asp
            340                 345                 350

Thr Asp Ile Tyr Asn Ser Thr Asp Ile Ile Leu Leu Cys Arg Ile Lys
        355                 360                 365
```

-continued

```
Gln Ile Ile Asn Met Trp Gln Glu Val Gly Arg Ala Met Tyr Ala Pro
    370                 375                 380
Pro Ile Glu Gly Asn Ile Thr Cys Ser Ser Asn Ile Thr Gly Leu Leu
385                 390                 395                 400
Leu Thr Arg Asp Gly Gly Leu Thr Asn Glu Ser Lys Glu Thr Phe Arg
            405                 410                 415
Pro Gly Gly Gly Asp Met Arg Asp Asn Trp Arg Ser Glu Leu Tyr Lys
        420                 425                 430
Tyr Lys Val Val Glu Ile Lys Pro Leu Gly Ile Ala Pro Thr
    435                 440                 445

<210> SEQ ID NO 11
<211> LENGTH: 466
<212> TYPE: PRT
<213> ORGANISM: Human immunodeficiency virus

<400> SEQUENCE: 11

Leu Trp Val Thr Val Tyr Tyr Gly Val Pro Val Trp Lys Glu Ala Lys
1               5                   10                  15
Thr Thr Leu Phe Cys Ala Ser Asp Ala Lys Gly Tyr Asp Lys Glu Val
            20                  25                  30
His Asn Val Trp Ala Thr His Ala Cys Val Pro Thr Asp Pro Asn Pro
        35                  40                  45
Gln Glu Met Pro Leu Glu Asn Val Thr Glu Asn Phe Asn Met Trp Glu
    50                  55                  60
Asn Asp Met Val Asn Gln Met His Glu Asp Val Ile Ser Leu Trp Asp
65                  70                  75                  80
Glu Ser Leu Lys Pro Cys Val Lys Leu Thr Pro Leu Cys Val Thr Leu
                85                  90                  95
Asn Cys Thr Asp Val Asn Lys Asn Val Ser Ser Asp Thr Asp Asn
            100                 105                 110
Tyr Lys Glu Thr Met Lys Glu Arg Lys Asn Cys Thr Phe Asn Met Thr
        115                 120                 125
Thr Glu Leu Arg Asp Lys Asn Gln Lys Lys Tyr Ala Leu Phe Tyr Lys
    130                 135                 140
Leu Asp Ile Val Pro Leu Asp Asp Asn Asp Asn Ala Ser Tyr Arg Leu
145                 150                 155                 160
Ile Asn Cys Asn Thr Ser Thr Leu Thr Gln Ala Cys Pro Lys Val Ser
                165                 170                 175
Phe Asp Pro Ile Pro Ile His Tyr Cys Ala Pro Ala Gly Tyr Ala Ile
            180                 185                 190
Leu Lys Cys Lys Asn Lys Thr Phe Asn Gly Ile Gly Pro Cys Asn Lys
        195                 200                 205
Val Ser Thr Val Gln Cys Thr His Gly Ile Lys Pro Val Val Ser Thr
    210                 215                 220
Gln Leu Leu Leu Asn Gly Ser Leu Ala Glu Glu Asp Ile Val Ile Arg
225                 230                 235                 240
Ser Glu Asn Ile Thr Asp Asn Ala Lys Thr Ile Ile Val His Leu Asn
                245                 250                 255
Glu Ser Val Glu Ile Val Cys Ile Arg Pro Asn Asn Thr Arg Lys
            260                 265                 270
Ser Ile Arg Ile Gly Pro Gly Gln Thr Phe Tyr Ala Thr Gly Asp Ile
        275                 280                 285
Val Gly Asp Ile Arg Gln Ala Tyr Cys Asn Ile Ser Glu Gly Lys Trp
```

```
                290                 295                 300
Asn Lys Thr Leu Gln Arg Val Ser Glu Lys Leu Ala Glu His Phe Pro
305                 310                 315                 320

Asn Ser Thr Ile Asn Phe Asn Ser Ser Gly Gly Asp Leu Glu Ile
                325                 330                 335

Thr Thr His Ser Phe Asn Cys Gly Gly Glu Phe Phe Tyr Cys Asn Thr
                340                 345                 350

Ser Gly Leu Phe Asn Gly Thr Tyr Met Asn Asn Asp Thr Lys Ser Asn
                355                 360                 365

Asp Thr Lys Ser Asn Ser Ser Ile Ile Thr Ile Pro Cys Arg Ile
                370                 375                 380

Lys Gln Ile Ile Asn Met Trp Gln Glu Val Gly Arg Ala Val Tyr Ala
385                 390                 395                 400

Pro Pro Ile Ala Gly Asn Ile Thr Cys Lys Ser Asn Ile Thr Gly Ile
                405                 410                 415

Leu Leu Thr Arg Asp Gly Gly Arg Gly Glu Glu Val Lys Asn Asp Thr
                420                 425                 430

Glu Thr Phe Arg Pro Gly Gly Gly Asn Met Lys Asp Asn Trp Arg Ser
                435                 440                 445

Glu Leu Tyr Lys Tyr Lys Val Val Glu Ile Lys Pro Leu Gly Val Ala
                450                 455                 460

Pro Thr
465
```

<210> SEQ ID NO 12
<211> LENGTH: 472
<212> TYPE: PRT
<213> ORGANISM: Human immunodeficiency virus

<400> SEQUENCE: 12

```
Leu Trp Val Thr Val Tyr Tyr Gly Val Pro Val Trp Lys Glu Ala Lys
1               5                   10                  15

Thr Thr Leu Phe Cys Ala Ser Asp Ala Lys Ala Tyr Asp Lys Glu Val
                20                  25                  30

His Asn Val Trp Ala Thr His Ala Cys Val Pro Thr Asp Pro Asn Pro
                35                  40                  45

Gln Glu Ile Val Leu Glu Asn Val Thr Glu Asn Phe Asn Met Trp Lys
                50                  55                  60

Asn Asp Met Val Asp Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Lys Asn Val Asn Ile Ser Ala Asn Ala Asn Ala Thr Ala Thr
                100                 105                 110

Leu Asn Ser Ser Met Asn Gly Glu Ile Lys Asn Cys Ser Phe Asn Thr
                115                 120                 125

Thr Thr Glu Leu Arg Asp Lys Lys Gln Lys Val Tyr Ala Leu Phe Tyr
                130                 135                 140

Lys Pro Asp Val Val Pro Leu Asn Gly Gly Glu His Asn Glu Thr Gly
145                 150                 155                 160

Glu Tyr Ile Leu Ile Asn Cys Asn Ser Ser Thr Ile Thr Gln Ala Cys
                165                 170                 175

Pro Lys Val Ser Phe Asp Pro Ile Pro Ile His Tyr Cys Ala Pro Ala
                180                 185                 190
```

Gly Tyr Ala Ile Leu Lys Cys Asn Asn Lys Thr Phe Asn Gly Thr Gly
              195                 200                 205

Pro Cys Asn Asn Val Ser Thr Val Gln Cys Thr His Gly Ile Lys Pro
    210                 215                 220

Val Val Ser Thr Gln Leu Leu Leu Asn Gly Ser Leu Ala Glu Glu Glu
225                 230                 235                 240

Ile Ile Val Arg Ser Glu Asn Leu Thr Asn Asn Ile Lys Thr Ile Ile
                245                 250                 255

Val His Leu Asn Lys Ser Val Glu Ile Lys Cys Thr Arg Pro Asn Asn
                260                 265                 270

Asn Thr Arg Lys Ser Val Arg Ile Gly Pro Gly Gln Thr Phe Tyr Ala
        275                 280                 285

Thr Gly Glu Ile Ile Gly Asp Ile Arg Glu Ala His Cys Asn Ile Ser
290                 295                 300

Arg Glu Thr Trp Asn Ser Thr Leu Ile Gln Val Lys Glu Lys Leu Arg
305                 310                 315                 320

Glu His Tyr Asn Lys Thr Ile Lys Phe Glu Pro Ser Ser Gly Gly Asp
                325                 330                 335

Leu Glu Val Thr Thr His Ser Phe Asn Cys Arg Gly Glu Phe Phe Tyr
                340                 345                 350

Cys Asp Thr Thr Lys Leu Phe Asn Glu Thr Lys Leu Phe Asn Glu Ser
        355                 360                 365

Glu Tyr Val Asp Asn Lys Thr Ile Ile Leu Pro Cys Arg Ile Lys Gln
        370                 375                 380

Ile Ile Asn Met Trp Gln Glu Val Gly Arg Ala Met Tyr Ala Pro Pro
385                 390                 395                 400

Ile Glu Gly Asn Ile Thr Cys Lys Ser Asn Ile Thr Gly Leu Leu Leu
                405                 410                 415

Thr Trp Asp Gly Gly Glu Asn Ser Thr Glu Gly Val Phe Arg Pro Gly
                420                 425                 430

Gly Gly Asn Met Lys Asp Asn Trp Arg Ser Glu Leu Tyr Lys Tyr Lys
                435                 440                 445

Val Val Glu Ile Lys Pro Leu Gly Val Ala Pro Thr Lys Ser Lys Arg
450                 455                 460

Lys Val Val Gly Arg Glu Lys Arg
465                 470

<210> SEQ ID NO 13
<211> LENGTH: 448
<212> TYPE: PRT
<213> ORGANISM: Human immunodeficiency virus

<400> SEQUENCE: 13

Leu Trp Val Thr Val Tyr Tyr Gly Val Pro Val Trp Lys Glu Ala Lys
1               5                   10                  15

Ala Thr Leu Phe Cys Ala Ser Asp Ala Arg Ala Tyr Glu Lys Glu Val
                20                  25                  30

His Asn Val Trp Ala Thr His Ala Cys Val Pro Thr Asp Pro Asn Pro
            35                  40                  45

Gln Glu Ile Tyr Leu Gly Asn Val Thr Glu Asn Phe Asn Met Trp Lys
        50                  55                  60

Asn Asp Met Val Asp Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

-continued

Arg Cys Thr Asn Ala Thr Ile Asn Gly Ser Leu Thr Glu Glu Val Lys
              100                 105                 110

Asn Cys Ser Phe Asn Ile Thr Thr Glu Leu Arg Asp Lys Lys Gln Lys
              115                 120                 125

Ala Tyr Ala Leu Phe Tyr Arg Pro Asp Val Val Pro Leu Asn Lys Asn
              130                 135                 140

Ser Pro Ser Gly Asn Ser Ser Glu Tyr Ile Leu Ile Asn Cys Asn Thr
145                 150                 155                 160

Ser Thr Ile Thr Gln Ala Cys Pro Lys Val Ser Phe Asp Pro Ile Pro
              165                 170                 175

Ile His Tyr Cys Ala Pro Ala Gly Tyr Ala Ile Leu Lys Cys Asn Asn
              180                 185                 190

Lys Thr Phe Asn Gly Thr Gly Pro Cys Asn Asn Val Ser Thr Val Gln
              195                 200                 205

Cys Thr His Gly Ile Lys Pro Val Val Ser Thr Gln Leu Leu Leu Asn
              210                 215                 220

Gly Ser Leu Ala Glu Glu Asp Ile Ile Ile Lys Ser Glu Asn Leu Thr
225                 230                 235                 240

Asn Asn Ile Lys Thr Ile Ile Val His Leu Asn Lys Ser Val Glu Ile
              245                 250                 255

Val Cys Arg Arg Pro Asn Asn Asn Thr Arg Lys Ser Ile Arg Ile Gly
              260                 265                 270

Pro Gly Gln Ala Phe Tyr Ala Thr Asn Asp Ile Ile Gly Asp Ile Arg
              275                 280                 285

Gln Ala His Cys Asn Ile Asn Asn Ser Thr Trp Asn Arg Thr Leu Glu
              290                 295                 300

Gln Ile Lys Lys Lys Leu Arg Glu His Phe Leu Asn Arg Thr Ile Glu
305                 310                 315                 320

Phe Glu Pro Pro Ser Gly Gly Asp Leu Glu Val Thr Thr His Ser Phe
              325                 330                 335

Asn Cys Gly Gly Glu Phe Phe Tyr Cys Asn Thr Thr Arg Leu Phe Lys
              340                 345                 350

Trp Ser Ser Asn Val Thr Asn Asp Thr Ile Thr Ile Pro Cys Arg Ile
              355                 360                 365

Lys Gln Phe Ile Asn Met Trp Gln Gly Ala Gly Arg Ala Met Tyr Ala
              370                 375                 380

Pro Pro Ile Glu Gly Asn Ile Thr Cys Asn Ser Ser Ile Thr Gly Leu
385                 390                 395                 400

Leu Leu Thr Arg Asp Gly Gly Lys Thr Asp Arg Asn Asp Thr Glu Ile
              405                 410                 415

Phe Arg Pro Gly Gly Gly Asn Met Lys Asp Asn Trp Arg Asn Glu Leu
              420                 425                 430

Tyr Lys Tyr Lys Val Val Glu Ile Lys Pro Leu Gly Val Ala Pro Thr
              435                 440                 445

<210> SEQ ID NO 14
<211> LENGTH: 459
<212> TYPE: PRT
<213> ORGANISM: Human immunodeficiency virus

<400> SEQUENCE: 14

Leu Trp Val Thr Val Tyr Tyr Gly Val Pro Val Trp Arg Glu Ala Lys
1               5                   10                  15

Thr Thr Leu Phe Cys Ala Ser Asp Ala Lys Ala Tyr Glu Lys Glu Val

```
            20                  25                  30
His Asn Val Trp Val Thr His Ala Cys Val Pro Thr Asp Pro Asn Pro
        35                  40                  45

Gln Glu Met Asn Leu Glu Asn Val Thr Glu Asn Phe Asn Met Trp Lys
    50                  55                  60

Asn Asp Met Val Asp Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Asn Asn Val Asn Val Thr His Asn Ser Thr Tyr Asn Asn Thr
            100                 105                 110

Glu Gly Glu Gln Ile Lys Asn Cys Ser Phe Asn Ile Thr Thr Glu Leu
        115                 120                 125

Arg Asp Lys Lys Gln Lys Val Tyr Ala Leu Phe Tyr Lys Leu Asp Ile
    130                 135                 140

Leu Pro Leu Asn Gly Asn Asn Asp Ser Asn Glu Tyr Arg Leu Ile Asn
145                 150                 155                 160

Cys Asn Thr Ser Ala Ile Thr Gln Ala Cys Pro Lys Val Ser Phe Asp
                165                 170                 175

Pro Ile Pro Ile His Tyr Cys Ala Pro Ala Gly Tyr Ala Ile Leu Lys
            180                 185                 190

Cys Asn Asn Lys Thr Phe Asn Gly Lys Gly Pro Cys Asn Asn Val Ser
        195                 200                 205

Thr Val Gln Cys Thr His Gly Ile Lys Pro Val Val Ser Thr Gln Leu
    210                 215                 220

Leu Leu Asn Gly Ser Leu Ala Glu Lys Glu Ile Ile Ile Arg Ser Glu
225                 230                 235                 240

Asn Ile Thr Asp Asn Val Lys Ile Ile Ile Val His Leu Asn Glu Ser
                245                 250                 255

Val Glu Ile Asn Cys Thr Arg Pro Asn Asn Asn Thr Arg Lys Ser Ile
            260                 265                 270

Arg Ile Gly Pro Gly Gln Thr Phe Tyr Ala Thr Gly Glu Ile Ile Gly
        275                 280                 285

Lys Ile Arg Glu Ala His Cys Asn Ile Ser Lys Glu Lys Trp Asn Lys
    290                 295                 300

Thr Leu Leu Arg Val Ala Lys Lys Leu Arg Glu His Phe Pro Gly Lys
305                 310                 315                 320

Ala Ile Lys Phe Glu Pro Ser Ser Gly Gly Asp Leu Glu Ile Thr Thr
                325                 330                 335

His Ser Phe Asn Cys Arg Gly Glu Phe Phe Tyr Cys Thr Thr Ser Lys
            340                 345                 350

Leu Phe Asn Ser Thr Tyr Asn Pro Asn Asp Thr Glu Ser Asn Ser Asn
        355                 360                 365

Asn Ser Asn Glu Thr Leu Thr Leu Thr Cys Lys Ile Lys Gln Ile Ile
    370                 375                 380

Asn Met Trp Gln Gly Val Gly Arg Ala Met Tyr Ala Pro Pro Ile Glu
385                 390                 395                 400

Gly Ser Ile Thr Cys Asn Ser Thr Ile Thr Gly Leu Leu Leu Thr Arg
                405                 410                 415

Asp Gly Gly Ser Lys Asn Asn Thr Glu Glu Ile Phe Arg Pro Gly Gly
            420                 425                 430

Gly Asn Met Lys Asp Asn Trp Arg Ser Glu Leu Tyr Lys Tyr Lys Val
        435                 440                 445
```

```
Val Glu Ile Lys Pro Leu Gly Val Ala Pro Thr
    450                 455

<210> SEQ ID NO 15
<211> LENGTH: 478
<212> TYPE: PRT
<213> ORGANISM: Human immunodeficiency virus

<400> SEQUENCE: 15

Leu Trp Val Thr Val Tyr Tyr Gly Val Pro Val Trp Arg Glu Ala Lys
1               5                   10                  15

Thr Thr Leu Phe Cys Ala Ser Asp Ala Lys Ala Tyr Glu Lys Glu Val
            20                  25                  30

His Asn Val Trp Ala Thr His Ala Cys Val Pro Thr Asp Pro Asn Pro
        35                  40                  45

Gln Glu Leu Val Leu Glu Asn Val Thr Glu Asn Phe Asn Met Trp Lys
    50                  55                  60

Asn Asp Met Val Asn Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Ser Asn Val Asn Ile Asn Glu Thr Ser Ile Asp Phe Asn Val
            100                 105                 110

Thr Ser Asn Ile Ser Met Lys Glu Glu Met Lys Asn Cys Ser Phe Lys
        115                 120                 125

Val Asn Ser Glu Leu Arg Asp Lys Asn Arg Arg Glu His Ala Leu Phe
    130                 135                 140

Tyr Lys Leu Asp Ile Val Gln Leu Asn Asp Glu Gly Asn Asp Ser Tyr
145                 150                 155                 160

Ser Tyr Arg Leu Ile Asn Cys Asn Thr Ser Thr Ile Lys Gln Ala Cys
                165                 170                 175

Pro Lys Val Ser Phe Glu Pro Ile Pro Ile His Tyr Cys Ala Pro Ala
            180                 185                 190

Gly Tyr Ala Ile Leu Lys Cys Asn Asn Glu Thr Phe Asn Gly Ser Gly
        195                 200                 205

Pro Cys Asn Asn Val Ser Thr Val Gln Cys Thr His Gly Ile Lys Pro
    210                 215                 220

Val Val Ser Thr Gln Leu Leu Leu Asn Gly Ser Leu Ala Glu Lys Glu
225                 230                 235                 240

Ile Met Ile Arg Ser Glu Asn Leu Thr Asn Asn Ala Lys Thr Ile Ile
                245                 250                 255

Val Gln Leu Thr Glu Ala Val Asn Ile Thr Cys Met Arg Pro Gly Asn
            260                 265                 270

Asn Thr Arg Arg Ser Val Arg Ile Gly Pro Gly Gln Thr Phe Tyr Ala
        275                 280                 285

Thr Gly Glu Ile Ile Gly Asp Ile Arg Gln Ala His Cys Asn Ile Ser
    290                 295                 300

Lys Asp Lys Trp Asn Gln Ile Leu Gln Asn Val Arg Ala Lys Leu Gly
305                 310                 315                 320

Glu His Phe His Asp Lys Thr Ile Lys Phe Glu Pro Ser Ser Gly Gly
                325                 330                 335

Asp Leu Glu Ile Thr Thr His Ser Phe Asn Cys Gly Gly Glu Phe Phe
            340                 345                 350

Tyr Cys Asn Thr Thr Asn Leu Phe Ser Arg Thr Tyr Thr Asn Gly Ser
```

```
            355                 360                 365
Asn Ser Asn Val Asn Ile Thr Ser Ala Thr Ile Thr Leu Pro Cys Arg
    370                 375                 380

Ile Lys Gln Ile Ile Asn Met Trp Gln Glu Val Gly Arg Ala Met Tyr
385                 390                 395                 400

Ala Pro Pro Ile Ala Gly Asn Ile Thr Cys Ile Ser Asn Ile Thr Gly
                405                 410                 415

Leu Leu Leu Thr Arg Asp Gly Gly Asn Gly Asn Asp Thr Asn Asp Thr
            420                 425                 430

Glu Thr Phe Arg Pro Ala Gly Gly Asp Met Arg Asp Asn Trp Arg Ser
            435                 440                 445

Glu Leu Tyr Lys Tyr Lys Val Val Glu Ile Lys Pro Leu Gly Ile Ala
            450                 455                 460

Pro Thr Lys Ala Lys Arg Arg Val Val Gly Arg Glu Lys Arg
465                 470                 475

<210> SEQ ID NO 16
<211> LENGTH: 446
<212> TYPE: PRT
<213> ORGANISM: Human immunodeficiency virus

<400> SEQUENCE: 16

Leu Trp Val Thr Val Tyr Tyr Gly Val Pro Val Trp Arg Glu Ala Lys
1               5                   10                  15

Thr Thr Leu Phe Cys Ala Ser Asp Ala Lys Ala Tyr Glu Thr Glu Ala
                20                  25                  30

His Ser Val Trp Ala Thr His Ala Cys Val Pro Thr Asp Pro Asn Pro
            35                  40                  45

Gln Glu Met Val Leu Glu Asn Val Thr Glu Asn Phe Asn Met Trp Lys
        50                  55                  60

Asn Asp Met Val Asp Gln Met His Glu Asp Val Ile Ser Ile Trp Asp
65                  70                  75                  80

Gln Ser Leu Lys Pro Cys Val Lys Leu Thr Pro Leu Cys Val Thr Leu
                85                  90                  95

Asp Cys Ser Thr Tyr Asn Asn Thr His Asn Ile Ser Lys Glu Met Lys
                100                 105                 110

Ile Cys Ser Phe Asn Met Thr Thr Glu Leu Arg Asp Lys Lys Arg Lys
            115                 120                 125

Val Asn Val Leu Phe Tyr Lys Leu Asp Leu Val Pro Leu Thr Asn Ser
130                 135                 140

Ser Asn Thr Thr Asn Tyr Arg Leu Ile Ser Cys Asn Thr Ser Thr Ile
145                 150                 155                 160

Thr Gln Ala Cys Pro Lys Val Ser Phe Asp Pro Ile Pro Ile His Tyr
                165                 170                 175

Cys Ala Pro Ala Gly Tyr Ala Ile Leu Lys Cys Asn Asn Lys Thr Phe
            180                 185                 190

Asn Gly Thr Gly Pro Cys Asn Asn Val Ser Thr Val Gln Cys Thr His
        195                 200                 205

Gly Ile Lys Pro Val Val Ser Thr Gln Leu Leu Leu Asn Gly Ser Leu
    210                 215                 220

Ala Glu Glu Glu Ile Ile Ile Arg Phe Glu Asn Leu Thr Asp Asn Val
225                 230                 235                 240

Lys Ile Ile Ile Val Gln Leu Asn Glu Thr Ile Asn Ile Thr Cys Thr
                245                 250                 255
```

-continued

```
Arg Pro Asn Asn Asn Thr Arg Lys Ser Ile Arg Ile Gly Pro Gly Gln
                260                 265                 270

Ser Phe Tyr Ala Thr Gly Glu Ile Val Gly Asn Ile Arg Glu Ala His
            275                 280                 285

Cys Asn Ile Ser Ala Ser Lys Trp Asn Lys Thr Leu Glu Arg Val Arg
        290                 295                 300

Thr Lys Leu Lys Glu His Phe Pro Asn Lys Thr Ile Glu Phe Glu Pro
305                 310                 315                 320

Ser Ser Gly Gly Asp Leu Glu Ile Thr Thr His Ser Phe Asn Cys Gly
                325                 330                 335

Gly Glu Phe Phe Tyr Cys Asn Thr Ser Gly Leu Phe Asn Ser Ala Ile
            340                 345                 350

Asn Gly Thr Leu Thr Ser Asn Val Thr Leu Pro Cys Arg Ile Lys Gln
        355                 360                 365

Ile Ile Asn Met Trp Gln Glu Val Gly Arg Ala Met Tyr Ala Pro Pro
370                 375                 380

Ile Ala Gly Asn Ile Thr Cys Lys Ser Asn Ile Thr Gly Leu Leu Leu
385                 390                 395                 400

Thr Arg Asp Gly Gly Glu Asn Ser Ser Thr Thr Glu Thr Phe Arg
                405                 410                 415

Pro Thr Gly Gly Asp Met Lys Asn Asn Trp Arg Ser Glu Leu Tyr Lys
            420                 425                 430

Tyr Lys Val Val Glu Ile Lys Pro Leu Gly Ile Ala Pro Thr
            435                 440                 445

<210> SEQ ID NO 17
<211> LENGTH: 469
<212> TYPE: PRT
<213> ORGANISM: Human immunodeficiency virus

<400> SEQUENCE: 17

Leu Trp Val Thr Val Tyr Tyr Gly Val Pro Val Trp Lys Glu Ala Lys
1               5                   10                  15

Thr Thr Leu Phe Cys Ala Ser Asp Ala Lys Gly Tyr Asp Thr Glu Val
            20                  25                  30

His Asn Val Trp Ala Thr His Ala Cys Val Pro Thr Asp Pro Asn Pro
        35                  40                  45

Gln Glu Ile Val Leu Glu Asn Val Thr Glu Asn Phe Asn Met Trp Lys
    50                  55                  60

Asn Asp Met Val Asp Gln Met His Gln Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Ser Asp Ala Thr Tyr Asn Asn Gly Thr Asn Ser Thr Asp Thr
            100                 105                 110

Met Lys Ile Cys Ser Phe Asn Ala Thr Thr Glu Leu Arg Asp Lys Lys
        115                 120                 125

Lys Lys Glu Tyr Ala Leu Phe Tyr Arg Leu Asp Ile Val Pro Leu Lys
    130                 135                 140

Asn Glu Ser Glu Ser Gln Asn Phe Ser Glu Tyr Ile Leu Ile Asn Cys
145                 150                 155                 160

Asn Thr Ser Thr Ile Ala Gln Ala Cys Pro Lys Val Ser Phe Asp Pro
                165                 170                 175

Ile Pro Ile His Tyr Cys Ala Pro Ala Gly Tyr Ala Ile Leu Lys Cys
            180                 185                 190
```

-continued

```
Asn Asn Lys Thr Phe Asn Gly Thr Gly Pro Cys Asn Asn Val Ser Thr
            195                 200                 205
Val Gln Cys Thr His Gly Ile Lys Pro Val Val Ser Thr Gln Leu Leu
210                 215                 220
Leu Asn Gly Ser Leu Ala Glu Glu Val Val Ile Arg Ser Glu Asn
225                 230                 235                 240
Ile Ser Asn Asn Val Lys Thr Ile Ile Val His Leu Asn Glu Ser Val
                245                 250                 255
Asn Ile Thr Cys Ile Arg Pro Gly Asn Asn Thr Arg Arg Ser Ile Arg
            260                 265                 270
Ile Gly Pro Gly Gln Ala Phe Tyr Ala Met Gly Asp Ile Ile Gly Asn
            275                 280                 285
Ile Arg Glu Ala His Cys Asn Ile Ser Glu Lys Ala Trp Asn Glu Thr
290                 295                 300
Leu Lys Lys Val Val Glu Lys Leu Val Lys Tyr Phe Pro Asn Lys Thr
305                 310                 315                 320
Ile Glu Phe Ala Pro Pro Val Gly Gly Asp Leu Glu Ile Thr Thr His
                325                 330                 335
Ser Phe Asn Cys Gly Gly Glu Phe Phe Tyr Cys Asn Thr Thr Lys Leu
            340                 345                 350
Phe Asn Ser Thr His Asn Ser Thr Asp Ser Thr Val Asn Ser Thr Asp
            355                 360                 365
Ser Thr Ala Glu Thr Gly Asn Ser Thr Asn Thr Asn Ile Thr Leu Pro
370                 375                 380
Cys Arg Ile Arg Gln Ile Ile Asn Met Trp Gln Glu Val Gly Arg Ala
385                 390                 395                 400
Met Tyr Ala Pro Pro Ser Lys Gly Asn Ile Thr Cys Ile Ser Asn Ile
                405                 410                 415
Thr Gly Leu Leu Leu Thr Arg Asp Gly Gly Glu Asn Lys Thr Glu Asn
            420                 425                 430
Asn Asp Thr Glu Ile Phe Arg Pro Gly Gly Gly Asp Met Lys Asp Asn
            435                 440                 445
Trp Arg Ser Glu Leu Tyr Lys Tyr Lys Val Val Glu Ile Lys Pro Leu
450                 455                 460
Gly Val Ala Pro Thr
465

<210> SEQ ID NO 18
<211> LENGTH: 463
<212> TYPE: PRT
<213> ORGANISM: Human immunodeficiency virus

<400> SEQUENCE: 18

Leu Trp Val Thr Val Tyr Tyr Gly Val Pro Val Trp Lys Glu Ala Lys
1               5                   10                  15
Thr Thr Leu Phe Cys Ala Ser Asp Ala Lys Ala His Lys Glu Glu Val
                20                  25                  30
His Asn Ile Trp Ala Thr His Ala Cys Val Pro Thr Asp Pro Asn Pro
            35                  40                  45
Gln Glu Ile Val Leu Lys Asn Val Thr Glu Asn Phe Asn Met Trp Lys
        50                  55                  60
Asn Asp Met Val Asp Gln Met His Glu Asp Ile Ile Ser Leu Trp Asp
65                  70                  75                  80
Gln Ser Leu Lys Pro Cys Val Lys Leu Thr Pro Leu Cys Val Thr Leu
```

```
                    85                  90                  95
Asn Cys Ser Asp Val Lys Ile Lys Gly Thr Asn Ala Thr Tyr Asn Asn
                100                 105                 110

Ala Thr Tyr Asn Asn Asn Thr Ile Ser Asp Met Lys Asn Cys Ser
            115                 120                 125

Phe Asn Thr Thr Thr Glu Ile Thr Asp Lys Lys Lys Glu Tyr Ala
        130                 135                 140

Leu Phe Tyr Lys Leu Asp Val Val Ala Leu Asp Gly Lys Glu Thr Asn
145                 150                 155                 160

Ser Thr Asn Ser Ser Glu Tyr Arg Leu Ile Asn Cys Asn Thr Ser Ala
                165                 170                 175

Val Thr Gln Ala Cys Pro Lys Val Ser Phe Asp Pro Ile Pro Ile His
            180                 185                 190

Tyr Cys Ala Pro Ala Gly Tyr Ala Ile Leu Lys Cys Asn Asn Lys Thr
        195                 200                 205

Phe Asn Gly Thr Gly Pro Cys Asn Asn Val Ser Thr Val Gln Cys Thr
    210                 215                 220

His Gly Ile Lys Pro Val Val Ser Thr Gln Leu Leu Leu Asn Gly Ser
225                 230                 235                 240

Leu Ala Glu Glu Glu Val Val Ile Arg Phe Glu Asn Leu Thr Asn Asn
                245                 250                 255

Ala Lys Ile Ile Ile Val His Leu Asn Glu Ser Val Glu Ile Asn Cys
            260                 265                 270

Thr Arg Pro Ser Asn Asn Thr Arg Lys Ser Val Arg Ile Gly Pro Gly
        275                 280                 285

Gln Thr Phe Phe Ala Thr Gly Asp Ile Ile Gly Asp Ile Arg Gln Ala
    290                 295                 300

His Cys Asn Ile Ser Arg Lys Lys Trp Asn Thr Thr Leu Gln Arg Val
305                 310                 315                 320

Lys Glu Lys Leu Lys Glu Lys Phe Pro Asn Lys Thr Ile Gln Phe Ala
                325                 330                 335

Pro Ser Ser Gly Gly Asp Leu Glu Ile Thr Thr His Ser Phe Asn Cys
            340                 345                 350

Arg Gly Glu Phe Phe Tyr Cys Tyr Thr Ser Asp Leu Phe Asn Ser Thr
        355                 360                 365

Tyr Met Ser Asn Asn Thr Gly Gly Ala Asn Ile Thr Leu Gln Cys Arg
    370                 375                 380

Ile Lys Gln Ile Ile Arg Met Trp Gln Gly Val Gly Gln Ala Met Tyr
385                 390                 395                 400

Ala Pro Pro Ile Ala Gly Asn Ile Thr Cys Lys Ser Asn Ile Thr Gly
                405                 410                 415

Leu Leu Leu Thr Arg Asp Gly Gly Lys Glu Lys Asn Asp Thr Glu Thr
            420                 425                 430

Phe Arg Pro Gly Gly Gly Asp Met Arg Asp Asn Trp Arg Ser Glu Leu
        435                 440                 445

Tyr Lys Tyr Lys Val Val Glu Ile Lys Pro Leu Gly Ile Ala Pro
    450                 455                 460

<210> SEQ ID NO 19
<211> LENGTH: 494
<212> TYPE: PRT
<213> ORGANISM: Human immunodeficiency virus

<400> SEQUENCE: 19
```

```
Leu Trp Val Thr Val Tyr Tyr Gly Val Pro Val Trp Lys Glu Ala Lys
1               5                   10                  15

Ala Thr Leu Phe Cys Ala Ser Asp Ala Lys Ala Tyr Glu Lys Glu Val
            20                  25                  30

His Asn Val Trp Ala Thr His Ala Cys Val Pro Thr Asp Pro Asn Pro
                35                  40                  45

Gln Glu Ile Pro Leu Gly Asn Val Thr Glu Asn Phe Asn Met Trp Lys
50                  55                  60

Asn Asp Met Ala Asp Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Ser Asp Ala Thr Ser Asn Thr Thr Lys Asn Ala Thr Asn Thr
                100                 105                 110

Asn Thr Thr Ser Thr Asp Asn Arg Asn Ala Thr Ser Asn Asp Thr Glu
                115                 120                 125

Met Lys Gly Glu Ile Lys Asp Cys Thr Phe Asn Ile Thr Thr Glu Val
            130                 135                 140

Arg Asp Arg Lys Thr Lys Gln Arg Ala Leu Phe Tyr Lys Leu Asp Val
145                 150                 155                 160

Val Pro Leu Glu Glu Glu Lys Asn Ser Ser Lys Asn Ser Ser Tyr
                165                 170                 175

Lys Glu Tyr Arg Leu Ile Ser Cys Asn Thr Ser Thr Ile Thr Gln Ala
                180                 185                 190

Cys Pro Lys Val Ser Phe Asp Pro Ile Pro Ile His Tyr Cys Ala Pro
                195                 200                 205

Ala Gly Tyr Ala Ile Leu Lys Cys Asn Asn Lys Thr Phe Asn Gly Thr
            210                 215                 220

Gly Pro Cys His Asn Val Ser Thr Val Gln Cys Thr His Gly Ile Lys
225                 230                 235                 240

Pro Val Val Ser Thr Gln Leu Leu Leu Asn Gly Ser Leu Ala Glu Glu
                245                 250                 255

Glu Ile Ile Ile Arg Ser Glu Asn Leu Thr Asp Asn Thr Lys Thr Ile
                260                 265                 270

Ile Val His Leu Asn Glu Ser Val Glu Ile Glu Cys Val Arg Pro Asn
            275                 280                 285

Asn Asn Thr Arg Lys Ser Val Arg Ile Gly Pro Gly Gln Thr Phe Phe
            290                 295                 300

Ala Thr Gly Glu Ile Ile Gly Asp Ile Arg Gln Ala His Cys Asp Leu
305                 310                 315                 320

Ser Lys Ser Asn Trp Thr Thr Thr Leu Lys Arg Ile Glu Lys Lys Leu
                325                 330                 335

Lys Glu His Phe Asn Asn Ala Thr Ile Lys Phe Glu Ser Ser Ala Gly
                340                 345                 350

Gly Asp Leu Glu Ile Thr Thr His Ser Phe Asn Cys Arg Gly Glu Phe
            355                 360                 365

Phe Tyr Cys Asn Thr Ser Gly Leu Phe Asn Ser Ser Leu Leu Asn Asp
            370                 375                 380

Thr Asp Gly Thr Ser Asn Ser Thr Ser Asn Ala Thr Ile Thr Leu Pro
385                 390                 395                 400

Cys Arg Ile Lys Gln Ile Ile Asn Met Trp Gln Glu Val Gly Arg Ala
                405                 410                 415

Met Tyr Ala Ser Pro Ile Ala Gly Ile Ile Thr Cys Lys Ser Asn Ile
```

```
                420             425             430
Thr Gly Leu Leu Leu Thr Arg Asp Gly Gly Asn Lys Ser Ala Gly Ile
            435                 440             445

Glu Thr Phe Arg Pro Gly Gly Gly Asn Met Lys Asp Asn Trp Arg Ser
450                 455                 460

Glu Leu Tyr Lys Tyr Lys Val Val Glu Ile Lys Pro Leu Gly Ile Ala
465                 470                 475                 480

Pro Thr Ser Ala Lys Arg Arg Val Val Glu Arg Glu Lys Arg
                485                 490

<210> SEQ ID NO 20
<211> LENGTH: 458
<212> TYPE: PRT
<213> ORGANISM: Human immunodeficiency virus

<400> SEQUENCE: 20

Leu Trp Val Thr Val Tyr Tyr Gly Val Pro Val Trp Arg Glu Ala Lys
1               5                   10                  15

Thr Thr Leu Phe Cys Ala Ser Asp Ala Lys Ala Tyr Glu Lys Glu Val
            20                  25                  30

His Asn Val Trp Ala Thr His Ala Cys Val Pro Thr Asp Pro Asn Pro
        35                  40                  45

Gln Glu Leu Val Leu Gly Asn Val Thr Glu Asn Phe Asn Met Trp Glu
    50                  55                  60

Asn Asp Met Val Asp Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Glu Cys Lys Asn Ala Thr Arg Ser Asn Gln Thr Thr Tyr Tyr Asp Asn
            100                 105                 110

Met Asp Lys Glu Ile Lys Asn Cys Ser Phe Asn Val Thr Thr Glu Leu
        115                 120                 125

Thr Asp Lys Lys Lys Asn Met Arg Ala Leu Phe Tyr Arg Ala Asp Ile
    130                 135                 140

Glu Pro Leu Asp Gly Asn Ser Asn Glu Ser Ile Asn Ser Ser Glu Gly
145                 150                 155                 160

Asp Lys Tyr Ile Leu Ile Asn Cys Asn Thr Ser Thr Ile Ala Gln Ala
                165                 170                 175

Cys Pro Lys Val Thr Phe Asp Pro Ile Pro Ile His Tyr Cys Ala Pro
            180                 185                 190

Ala Gly Tyr Ala Ile Leu Lys Cys Asn Asn Lys Thr Phe Asn Gly Ile
        195                 200                 205

Gly Pro Cys Lys Asn Val Ser Thr Val Gln Cys Thr His Gly Ile Lys
    210                 215                 220

Pro Val Val Ser Thr Gln Leu Leu Leu Asn Gly Ser Leu Ser Glu Glu
225                 230                 235                 240

Gly Ile Ile Ile Arg Ser Lys Asn Leu Thr Asp Asn Thr Lys Thr Ile
                245                 250                 255

Ile Val His Leu Asn Glu Ser Val Ala Ile Val Cys Thr Arg Pro Asn
            260                 265                 270

Asn Asn Thr Arg Lys Ser Ile Arg Ile Gly Pro Gly Gln Thr Phe Tyr
        275                 280                 285

Ala Thr Gly Glu Val Ile Gly Asp Ile Arg Gln Ala His Cys Asn Ile
    290                 295                 300
```

-continued

```
Ser Gly Glu Gln Trp Asn Arg Thr Leu Glu Arg Ile Lys Asp Lys Leu
305                 310                 315                 320

Thr Glu Tyr Phe Pro Asp Lys Ile Ile Lys Phe Asn His Ser Ser Gly
            325                 330                 335

Gly Asp Leu Glu Ile Thr Thr His Thr Phe Asn Cys Arg Gly Glu Phe
            340                 345                 350

Phe Tyr Cys Asn Thr Ser Ile Leu Phe Thr Glu Asn Glu Asn Ser Ser
            355                 360                 365

Asp Asn Ile Thr Leu Pro Cys Arg Ile Lys Gln Phe Val Asn Met Trp
            370                 375                 380

Gln Glu Val Gly Arg Ala Met Tyr Ala Pro Pro Ile Ala Gly Asn Ile
385                 390                 395                 400

Thr Cys Asn Ser Ser Ile Thr Gly Leu Leu Leu Thr Arg Asp Gly Gly
            405                 410                 415

Leu Asn Asn Lys Glu Asn Gly Thr Glu Thr Phe Arg Pro Gln Gly Gly
            420                 425                 430

Asp Met Arg Asp Asn Trp Arg Ser Glu Leu Tyr Lys Tyr Lys Val Val
            435                 440                 445

Glu Ile Arg Pro Leu Gly Val Ala Pro Thr
450                 455

<210> SEQ ID NO 21
<211> LENGTH: 457
<212> TYPE: PRT
<213> ORGANISM: Human immunodeficiency virus

<400> SEQUENCE: 21

Leu Trp Val Thr Val Tyr Tyr Gly Val Pro Val Trp Lys Glu Ala Lys
1               5                   10                  15

Thr Thr Leu Phe Cys Ala Ser Asp Ala Lys Ser Tyr Glu Arg Glu Val
            20                  25                  30

His Asn Val Trp Ala Thr His Ala Cys Val Pro Thr Asp Pro Asp Pro
        35                  40                  45

Gln Glu Leu Val Met Ala Asn Val Thr Glu Asn Phe Asn Met Trp Lys
    50                  55                  60

Asn Asp Met Val Asp Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Thr Ser Pro Ala Ala His Asn Glu Ser Glu Thr Arg Val Lys
            100                 105                 110

His Cys Ser Phe Asn Ile Thr Thr Asp Val Lys Asp Arg Lys Gln Lys
        115                 120                 125

Val Asn Ala Thr Phe Tyr Asp Leu Asp Ile Val Pro Leu Ser Ser Ser
    130                 135                 140

Asp Asn Ser Ser Asn Ser Ser Leu Tyr Arg Leu Ile Ser Cys Asn Thr
145                 150                 155                 160

Ser Thr Ile Thr Gln Ala Cys Pro Lys Val Ser Phe Asp Pro Ile Pro
                165                 170                 175

Ile His Tyr Cys Ala Pro Ala Gly Tyr Ala Ile Leu Lys Cys Asn Asn
            180                 185                 190

Lys Thr Phe Ser Gly Lys Gly Pro Cys Ser Asn Val Ser Thr Val Gln
        195                 200                 205

Cys Thr His Gly Ile Arg Pro Val Val Ser Thr Gln Leu Leu Leu Asn
    210                 215                 220
```

Gly Ser Leu Ala Glu Glu Ile Val Ile Arg Ser Glu Asn Leu Thr
225                 230                 235                 240

Asp Asn Ala Lys Thr Ile Ile Val His Leu Asn Lys Ser Val Glu Ile
            245                 250                 255

Glu Cys Ile Arg Pro Gly Asn Asn Thr Arg Lys Ser Ile Arg Leu Gly
260                 265                 270

Pro Gly Gln Thr Phe Tyr Ala Thr Gly Asp Val Ile Gly Asp Ile Arg
        275                 280                 285

Lys Ala Tyr Cys Lys Ile Asn Gly Ser Glu Trp Asn Glu Thr Leu Thr
290                 295                 300

Lys Val Ser Glu Lys Leu Lys Glu Tyr Phe Asn Lys Thr Ile Arg Phe
305                 310                 315                 320

Ala Gln His Ser Gly Gly Asp Leu Glu Val Thr Thr His Ser Phe Asn
            325                 330                 335

Cys Arg Gly Glu Phe Phe Tyr Cys Asn Thr Ser Glu Leu Phe Asn Ser
        340                 345                 350

Asn Ala Thr Glu Ser Asn Ile Thr Leu Pro Cys Arg Ile Lys Gln Ile
        355                 360                 365

Ile Asn Met Trp Gln Val Gly Arg Ala Met Tyr Ala Pro Pro Ile
370                 375                 380

Arg Gly Glu Ile Lys Cys Thr Ser Asn Ile Thr Gly Leu Leu Leu Thr
385                 390                 395                 400

Arg Asp Gly Gly Asn Asn Asn Ser Thr Glu Glu Ile Phe Arg Pro
        405                 410                 415

Glu Gly Gly Asn Met Arg Asp Asn Trp Arg Ser Glu Leu Tyr Lys Tyr
            420                 425                 430

Lys Val Val Glu Ile Lys Pro Leu Gly Ile Ala Pro Thr Glu Ala Lys
            435                 440                 445

Arg Arg Val Val Gln Arg Glu Lys Arg
    450                 455

<210> SEQ ID NO 22
<211> LENGTH: 477
<212> TYPE: PRT
<213> ORGANISM: Human immunodeficiency virus

<400> SEQUENCE: 22

Leu Trp Val Thr Val Tyr Tyr Gly Val Pro Val Trp Lys Glu Ala Thr
1               5                   10                  15

Thr Thr Leu Phe Cys Ala Ser Glu Ala Lys Ala Tyr Asp Thr Glu Val
            20                  25                  30

His Asn Val Trp Ala Thr His Ala Cys Val Pro Thr Asp Pro Asn Pro
        35                  40                  45

Gln Glu Val Glu Leu Gly Asn Val Thr Glu Asn Phe Asn Met Trp Lys
    50                  55                  60

Asn Asp Met Val Glu Gln Met His Glu Asp Ile Ile Ser Leu Trp Asp
65                  70                  75                  80

Gln Ser Leu Lys Pro Cys Val Arg Leu Thr Pro Leu Cys Val Thr Leu
                85                  90                  95

Asp Cys Thr Asp Leu Asn Asn Thr Thr Asn Thr Asn Thr Thr Asn
            100                 105                 110

Thr Asn Ser Ser Lys Ile Glu Gly Gly Glu Met Lys Asn Cys Ser Phe
        115                 120                 125

Asn Ile Thr Thr Asn Arg Gly Asp Lys Arg Gln Lys Glu Tyr Ala Leu

```
                    130                 135                 140
Leu Tyr Arg Thr Asp Ile Val Ser Ile Glu Asn Thr Ser Ser Tyr
145                 150                 155                 160

Arg Leu Ile Ser Cys Asn Thr Ser Val Ile Thr Gln Ala Cys Pro Lys
                165                 170                 175

Val Thr Phe Glu Pro Ile Pro Ile His Tyr Cys Ala Pro Ala Gly Phe
            180                 185                 190

Ala Ile Leu Lys Cys Asn Glu Asp Lys Phe Asn Gly Thr Gly Pro Cys
            195                 200                 205

Lys Asn Val Ser Thr Val Gln Cys Thr His Gly Ile Arg Pro Thr Val
210                 215                 220

Ser Thr Gln Leu Leu Leu Asn Gly Ser Leu Ala Lys Glu Glu Val Ile
225                 230                 235                 240

Ile Arg Ser Ala Asn Leu Ser Asp Asn Ala Lys Ile Ile Ile Val Gln
                245                 250                 255

Leu Lys Asp Pro Val Glu Ile Asn Cys Thr Arg Pro Asn Asn Asn Thr
            260                 265                 270

Arg Lys Ser Ile Asn Leu Gly Pro Gly Arg Ala Phe Tyr Ala Thr Gly
            275                 280                 285

Asp Ile Ile Gly Asp Ile Arg Gln Ala His Cys Asn Ile Ser Arg Ala
290                 295                 300

Lys Trp Asn Asp Thr Leu Arg Glu Ile Ala Lys Lys Leu Ala Glu Gln
305                 310                 315                 320

Phe Asn Asn Arg Thr Ile Val Phe Asn Gln Ser Ser Gly Gly Asp Pro
                325                 330                 335

Glu Ile Val Met His Ser Phe Asn Cys Ala Gly Glu Phe Phe Tyr Cys
            340                 345                 350

Asp Thr Ser Gln Leu Phe Asn Ser Thr Trp Asn Ser Asn Ser Thr Trp
            355                 360                 365

Asn Asp Thr Asn Asn Asn Ser Thr Glu Lys Ile Ile Leu Ser Cys
370                 375                 380

Arg Ile Arg Gln Ile Ile Asn Arg Trp Gln Glu Val Gly Lys Ala Met
385                 390                 395                 400

Tyr Ala Pro Pro Ile Ser Gly Pro Ile Lys Cys Ser Ser Asn Ile Thr
                405                 410                 415

Gly Leu Leu Leu Ala Arg Asp Gly Gly Asn Glu Thr Asn Val Thr Glu
            420                 425                 430

Thr Phe Arg Pro Ala Gly Gly Asp Met Arg Asp Asn Trp Arg Ser Glu
            435                 440                 445

Leu Tyr Lys Tyr Lys Val Val Gln Ile Glu Pro Leu Gly Ile Ala Pro
450                 455                 460

Thr Lys Ala Lys Arg Arg Val Val Gln Arg Glu Lys Arg
465                 470                 475

<210> SEQ ID NO 23
<211> LENGTH: 477
<212> TYPE: PRT
<213> ORGANISM: Human immunodeficiency virus

<400> SEQUENCE: 23

Leu Trp Val Thr Val Tyr Tyr Gly Val Pro Val Trp Lys Glu Ala Thr
1               5                   10                  15

Thr Thr Leu Phe Cys Ala Ser Asp Ala Lys Ala Tyr Glu Thr Glu Val
            20                  25                  30
```

-continued

```
His Asn Val Trp Ala Thr His Ala Cys Val Pro Thr Asp Pro Asn Pro
        35                  40                  45

Gln Glu Leu Val Leu Glu Asn Val Thr Glu Tyr Phe Asp Met Trp Lys
    50                  55                  60

Asn Asn Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Thr Asp Trp Thr Asn Gly Thr Asp Trp Asn Thr Thr Asn Ser
            100                 105                 110

Asn Asn Thr Thr Ile Ser Lys Glu Glu Thr Ile Glu Gly Gly Glu Met
        115                 120                 125

Lys Asn Cys Ser Phe Asn Ile Thr Thr Ala Thr Gly Asp Lys Lys Lys
    130                 135                 140

Glu Arg Ala Phe Phe Tyr Lys Leu Asp Val Ala Pro Ile Asp Asn Ser
145                 150                 155                 160

Asn Thr Ser Tyr Arg Leu Ile Ser Cys Asn Thr Ser Val Ile Thr Gln
                165                 170                 175

Ala Cys Pro Lys Ile Ser Phe Glu Pro Ile Pro Ile His Tyr Cys Ala
            180                 185                 190

Pro Ala Gly Phe Ala Ile Leu Lys Cys Asn Asp Lys Lys Phe Asn Gly
        195                 200                 205

Thr Gly Ser Cys Thr Asn Val Ser Thr Val Gln Cys Thr His Gly Ile
    210                 215                 220

Arg Pro Val Val Ser Thr Gln Leu Leu Leu Asn Gly Ser Leu Ala Glu
225                 230                 235                 240

Glu Glu Val Val Ile Arg Ser Lys Asn Phe Ser Asp Asn Ala Lys Ile
                245                 250                 255

Ile Ile Val Gln Leu Asn Glu Ser Val Pro Ile Asn Cys Thr Arg Pro
            260                 265                 270

His Asn Asn Thr Arg Lys Ser Ile His Ile Gly Pro Gly Arg Ala Trp
        275                 280                 285

Tyr Ala Thr Gly Asp Ile Ile Gly Asp Ile Arg Lys Ala Tyr Cys Asn
    290                 295                 300

Ile Ser Glu Ala Lys Trp Asn Asn Thr Leu Lys Gln Ile Thr Glu Lys
305                 310                 315                 320

Leu Lys Glu Gln Phe Asn Lys Thr Ile Ile Val Phe Asn Gln Pro Ser
                325                 330                 335

Gly Gly Asp Pro Glu Val Thr Met His Ser Phe Asn Cys Gly Gly Glu
            340                 345                 350

Phe Phe Tyr Cys Asn Thr Ser Lys Leu Phe Asn Gly Thr Trp Asn Ser
        355                 360                 365

Thr Lys Arg Ala Asn Asn Thr Glu Gly Ile Ile Ile Leu Gln Cys Arg
    370                 375                 380

Ile Lys Gln Ile Ile Asn Arg Trp Gln Glu Val Gly Lys Ala Met Tyr
385                 390                 395                 400

Ala Pro Pro Ile Glu Gly Gln Ile Lys Cys Ser Ser Asn Ile Thr Gly
                405                 410                 415

Leu Leu Leu Thr Arg Asp Gly Gly Lys Thr Ala Asn Asn Thr Thr Glu
            420                 425                 430

Phe Phe Arg Pro Gly Gly Gly Asn Met Lys Asp Asn Trp Arg Ser Glu
        435                 440                 445

Leu Tyr Lys Tyr Lys Val Val Arg Ile Glu Pro Leu Gly Val Ala Pro
```

```
                        450                     455                     460
Thr Lys Ala Lys Arg Arg Val Val Gln Arg Glu Lys Arg
465                     470                     475

<210> SEQ ID NO 24
<211> LENGTH: 478
<212> TYPE: PRT
<213> ORGANISM: Human immunodeficiency virus

<400> SEQUENCE: 24

Leu Trp Val Thr Val Tyr Tyr Gly Val Pro Val Trp Lys Glu Ala Thr
1               5                   10                  15

Thr Thr Leu Phe Cys Ala Ser Asp Ala Lys Ala Tyr Asp Gln Glu Ile
            20                  25                  30

His Asn Ile Trp Ala Thr His Ala Cys Val Pro Thr Asp Pro Asn Pro
        35                  40                  45

Gln Glu Val Glu Leu Lys Asn Val Thr Glu Asn Phe Asn Met Trp Lys
    50                  55                  60

Ser Asn Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Lys Cys Thr Asp Leu Asn Val Thr Asn Ser Asn Ser Thr Asp His Ser
            100                 105                 110

Thr Asn Ser Ser Leu Glu Ala Lys Gly Glu Ile Lys Asn Cys Ser Phe
        115                 120                 125

Asn Ile Thr Thr Thr Pro Arg Asp Lys Ile Gln Lys Glu Tyr Ala Ile
130                 135                 140

Phe Tyr Lys Gln Asp Val Val Pro Ile Lys Asn Asp Asn Ile Ser Tyr
145                 150                 155                 160

Arg Leu Ile Ser Cys Asn Thr Ser Val Ile Thr Gln Ala Cys Pro Lys
                165                 170                 175

Val Thr Phe Glu Pro Ile Pro Ile His Tyr Cys Ala Pro Ala Gly Phe
            180                 185                 190

Ala Ile Leu Lys Cys Asn Asp Lys Gly Phe Asn Gly Thr Gly Pro Cys
        195                 200                 205

Thr Asn Val Ser Thr Val Gln Cys Thr His Gly Ile Arg Pro Ala Ile
    210                 215                 220

Ser Thr Gln Leu Leu Leu Asn Gly Ser Leu Ala Glu Asp Lys Val Val
225                 230                 235                 240

Ile Arg Ser Glu Asn Phe Thr Asp Asn Ala Lys Ile Ile Ile Val His
                245                 250                 255

Leu Asn Glu Thr Val Lys Ile Asn Cys Thr Arg Pro Asn Asn Asn Thr
            260                 265                 270

Arg Lys Ser Ile His Ile Ala Pro Gly Arg Ala Phe Tyr Ala Thr Gly
        275                 280                 285

Glu Ile Ile Gly Asp Ile Arg Lys Ala Tyr Cys Thr Ile Asn Glu Ser
    290                 295                 300

Glu Trp Asn Asn Thr Leu Gln Lys Ile Val Val Thr Leu Arg Glu Gln
305                 310                 315                 320

Phe Arg Asn Lys Thr Ile Val Phe Asn Gln Ser Ser Gly Gly Asp Pro
                325                 330                 335

Glu Val Thr Met His Thr Phe Asn Cys Gly Gly Glu Phe Phe Tyr Cys
            340                 345                 350
```

-continued

Asn Thr Ala Gln Leu Phe Asn Ser Ser Trp Asp Thr Asn Thr Asn Gly
            355                 360                 365

Asn Asp Thr Gln Gly Pro Ser Glu Asn Asn Thr Ile Ile Leu Pro Cys
    370                 375                 380

Arg Ile Lys Gln Ile Ile Asn Met Trp Gln Arg Val Gly Lys Ala Ile
385                 390                 395                 400

Tyr Ala Pro Pro Ile Ser Gly Gln Ile Arg Cys Leu Ser Asn Ile Thr
            405                 410                 415

Gly Leu Ile Leu Thr Arg Asp Gly Gly Asn Ser Ser Leu Ser Ser Pro
            420                 425                 430

Glu Ile Phe Arg Pro Gly Gly Gly Asp Met Arg Asp Asn Trp Arg Ser
            435                 440                 445

Glu Leu Tyr Lys Tyr Lys Val Val Gln Ile Glu Pro Leu Gly Ile Ala
    450                 455                 460

Pro Thr Arg Ala Lys Arg Arg Ala Val Gln Arg Glu Lys Arg
465                 470                 475

<210> SEQ ID NO 25
<211> LENGTH: 484
<212> TYPE: PRT
<213> ORGANISM: Human immunodeficiency virus

<400> SEQUENCE: 25

Leu Trp Val Thr Val Tyr Tyr Gly Val Pro Val Trp Lys Asp Ala Ser
1               5                   10                  15

Thr Thr Leu Phe Cys Ala Ser Asp Ala Lys Ala Tyr Asp Thr Glu Val
            20                  25                  30

His Asn Val Trp Ala Thr His Ala Cys Val Pro Thr Asp Pro Asn Pro
        35                  40                  45

Gln Glu Val Val Leu Gly Asn Val Thr Glu Asn Phe Asn Met Trp Lys
    50                  55                  60

Asn Asn Met Val Asp Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Thr Asp Asn Ile Thr Asn Thr Asn Thr Asn Ser Ser Lys Asn
            100                 105                 110

Ser Ser His Ser Tyr Asn Asn Ser Leu Glu Gly Glu Met Lys Asn
        115                 120                 125

Cys Ser Phe Asn Ile Thr Ala Gly Ile Arg Asp Lys Val Lys Lys Glu
    130                 135                 140

Tyr Ala Leu Phe Tyr Lys Leu Asp Val Val Pro Ile Glu Glu Asp Lys
145                 150                 155                 160

Asp Thr Asn Lys Thr Thr Tyr Arg Leu Arg Ser Cys Asn Thr Ser Val
                165                 170                 175

Ile Thr Gln Ala Cys Pro Lys Val Thr Phe Glu Pro Ile Pro Ile His
            180                 185                 190

Tyr Cys Ala Pro Ala Gly Phe Ala Ile Leu Lys Cys Asn Asp Lys Lys
        195                 200                 205

Phe Asn Gly Thr Gly Pro Cys Thr Asn Val Ser Thr Val Gln Cys Thr
    210                 215                 220

His Gly Ile Arg Pro Val Val Ser Thr Gln Leu Leu Leu Asn Gly Ser
225                 230                 235                 240

Leu Ala Glu Glu Glu Val Val Ile Arg Ser Glu Asn Phe Thr Asn Asn
                245                 250                 255

Ala Lys Thr Ile Ile Val Gln Leu Asn Glu Ser Ile Ala Ile Asn Cys
            260                 265                 270

Thr Arg Pro Asn Asn Thr Arg Ser Ile His Ile Gly Pro Gly
        275                 280                 285

Arg Ala Phe Tyr Ala Thr Gly Asp Ile Ile Gly Asp Ile Arg Gln Ala
        290                 295                 300

His Cys Asn Ile Ser Arg Thr Glu Trp Asn Ser Thr Leu Arg Gln Ile
305                 310                 315                 320

Val Thr Lys Leu Arg Glu Gln Leu Gly Asp Pro Asn Lys Thr Ile Ile
                325                 330                 335

Phe Asn Gln Ser Ser Gly Gly Asp Thr Glu Ile Thr Met His Ser Phe
                340                 345                 350

Asn Cys Gly Gly Glu Phe Phe Tyr Cys Asn Thr Thr Lys Leu Phe Asn
                355                 360                 365

Ser Thr Trp Asn Gly Asn Asn Thr Thr Glu Ser Asp Ser Thr Gly Glu
        370                 375                 380

Asn Ile Thr Leu Pro Cys Arg Ile Lys Gln Ile Ile Asn Leu Trp Gln
385                 390                 395                 400

Glu Val Gly Lys Ala Met Tyr Ala Pro Pro Ile Lys Gly Gln Ile Ser
                405                 410                 415

Cys Ser Ser Asn Ile Thr Gly Leu Leu Leu Thr Arg Asp Gly Gly Asn
                420                 425                 430

Asn Asn Ser Ser Gly Pro Glu Thr Phe Arg Pro Gly Gly Gly Asn Met
            435                 440                 445

Lys Asp Asn Trp Arg Ser Glu Leu Tyr Lys Tyr Lys Val Ile Lys Ile
450                 455                 460

Glu Pro Leu Gly Val Ala Pro Thr Arg Ala Lys Arg Arg Val Val Gln
465                 470                 475                 480

Arg Glu Lys Arg

<210> SEQ ID NO 26
<211> LENGTH: 477
<212> TYPE: PRT
<213> ORGANISM: Human immunodeficiency virus

<400> SEQUENCE: 26

Leu Trp Val Thr Val Tyr Tyr Gly Val Pro Val Trp Lys Glu Ala Asn
1               5                   10                  15

Thr Thr Leu Phe Cys Ala Ser Asp Ala Lys Ala Tyr Asp Thr Glu Ala
                20                  25                  30

His Asn Val Trp Ala Thr His Ala Cys Val Pro Thr Asp Pro Asn Pro
            35                  40                  45

Gln Glu Val Val Leu Glu Asn Val Thr Glu Asn Phe Asn Met Trp Lys
        50                  55                  60

Asn His Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Thr Asp Leu Val Asn Ser Asn Ile Thr Arg Val Asp Asn Thr
            100                 105                 110

Thr Glu Lys Glu Met Lys Asn Cys Ser Phe Asn Val Thr Ser Gly Ile
        115                 120                 125

Arg Asp Lys Val Gln Lys Glu Tyr Ala Leu Leu Tyr Lys Leu Asp Ile
130                 135                 140

```
Val Gln Ile Asp Asn Asp Asn Thr Ser His Arg Asp Asn Thr Ser Tyr
145                 150                 155                 160

Arg Leu Ile Ser Cys Asn Thr Ser Val Ile Thr Gln Ala Cys Pro Lys
            165                 170                 175

Ile Ser Phe Glu Pro Ile Pro Ile His Phe Cys Ala Pro Ala Gly Phe
        180                 185                 190

Ala Ile Leu Lys Cys Asn Asp Lys Lys Phe Asn Gly Thr Gly Pro Cys
        195                 200                 205

Thr Asn Val Ser Thr Val Gln Cys Thr His Gly Ile Arg Pro Val Val
    210                 215                 220

Ser Thr Gln Leu Leu Leu Asn Gly Ser Leu Ala Glu Glu Val Val
225                 230                 235                 240

Ile Arg Ser Glu Asn Phe Thr Asn Asn Val Lys Asn Ile Ile Val Gln
                245                 250                 255

Leu Asn Glu Ser Val Gln Ile Asn Cys Thr Arg His Asn Asn Asn Thr
            260                 265                 270

Arg Lys Ser Ile Asn Ile Gly Pro Gly Arg Ala Phe Tyr Ala Thr Gly
        275                 280                 285

Lys Ile Ile Gly Asp Ile Arg Gln Ala His Cys Asn Ile Ser Arg Glu
        290                 295                 300

Lys Trp Gln Asn Thr Leu Lys Gln Ile Val Lys Lys Leu Arg Glu Gln
305                 310                 315                 320

Phe Lys Asn Lys Thr Ile Ala Phe Ala Pro Ser Ser Gly Gly Asp Pro
                325                 330                 335

Glu Ile Val Met His Ser Phe Asn Cys Asn Gly Glu Phe Phe Tyr Cys
            340                 345                 350

Asn Thr Thr Lys Leu Phe Thr Ser Thr Trp Asn Ser Thr Trp Asn Ser
        355                 360                 365

Thr Trp Asn Asn Thr Glu Gly Ser Asn Ser Thr Val Ile Thr Leu Pro
        370                 375                 380

Cys Arg Ile Arg Gln Ile Ile Asn Met Trp Gln Glu Val Gly Lys Ala
385                 390                 395                 400

Met Tyr Ala Pro Pro Ile Gln Gly Gln Ile Lys Cys Ser Ser Asn Ile
                405                 410                 415

Thr Gly Leu Leu Leu Thr Arg Asp Gly Gly Val Asp Thr Thr Lys Glu
            420                 425                 430

Thr Phe Arg Pro Gly Gly Gly Asn Met Lys Asp Asn Trp Arg Ser Glu
        435                 440                 445

Leu Tyr Lys Tyr Lys Val Val Arg Ile Glu Pro Leu Gly Val Ala Pro
        450                 455                 460

Thr Lys Ala Lys Arg Arg Val Val Gln Arg Glu Lys Arg
465                 470                 475

<210> SEQ ID NO 27
<211> LENGTH: 472
<212> TYPE: PRT
<213> ORGANISM: Human immunodeficiency virus

<400> SEQUENCE: 27

Leu Trp Val Thr Val Tyr Tyr Gly Val Pro Val Trp Arg Glu Ala Asn
1               5                   10                  15

Thr Thr Leu Phe Cys Ala Ser Asp Ala Lys Ala Tyr Asp Thr Glu Val
            20                  25                  30

His Asn Val Trp Ala Thr His Ala Cys Val Pro Thr Asp Pro Asn Pro
```

```
                35                  40                  45
Gln Glu Val Val Met Gly Asn Val Thr Glu Asp Phe Asn Met Trp Lys
 50                  55                  60

Asn Asn Met Val Glu Gln Met His Glu Asp Ile Ile Ser Leu Trp Asp
 65                  70                  75                  80

Gln Ser Leu Lys Pro Cys Val Lys Leu Thr Pro Leu Cys Val Thr Leu
                 85                  90                  95

His Cys Thr Asn Val Thr Ile Ser Ser Thr Asn Gly Ser Thr Ala Asn
                100                 105                 110

Val Thr Met Arg Glu Glu Met Lys Asn Cys Ser Phe Asn Thr Thr Thr
                115                 120                 125

Val Ile Arg Asp Lys Ile Gln Lys Glu Tyr Ala Leu Phe Tyr Lys Leu
                130                 135                 140

Asp Ile Val Pro Ile Glu Gly Lys Asn Thr Asn Thr Gly Tyr Arg Leu
145                 150                 155                 160

Ile Asn Cys Asn Thr Ser Val Ile Thr Gln Ala Cys Pro Lys Val Ser
                165                 170                 175

Phe Glu Pro Ile Pro Ile His Tyr Cys Ala Pro Ala Gly Phe Ala Ile
                180                 185                 190

Leu Lys Cys Asn Asn Lys Thr Phe Asn Gly Lys Gly Pro Cys Arg Asn
                195                 200                 205

Val Ser Thr Val Gln Cys Thr His Gly Ile Lys Pro Val Val Ser Thr
210                 215                 220

Gln Leu Leu Leu Asn Gly Ser Leu Ala Glu Glu Asp Ile Ile Ile Arg
225                 230                 235                 240

Ser Glu Asn Phe Thr Asn Asn Gly Lys Asn Ile Ile Val Gln Leu Lys
                245                 250                 255

Glu Pro Val Lys Ile Asn Cys Thr Arg Pro Gly Asn Asn Thr Arg Arg
                260                 265                 270

Ser Ile Asn Ile Gly Pro Gly Arg Ala Phe Tyr Ala Thr Gly Ala Ile
                275                 280                 285

Ile Gly Asp Ile Arg Lys Ala His Cys Asn Ile Ser Thr Glu Gln Trp
                290                 295                 300

Asn Asn Thr Leu Thr Gln Ile Val Asp Lys Leu Arg Glu Gln Phe Gly
305                 310                 315                 320

Asn Lys Thr Ile Ile Phe Asn Gln Ser Ser Gly Gly Asp Pro Glu Val
                325                 330                 335

Val Met His Thr Phe Asn Cys Gly Gly Glu Phe Phe Tyr Cys Asn Ser
                340                 345                 350

Thr Gln Leu Phe Asn Ser Thr Trp Phe Asn Asn Gly Thr Ser Thr Trp
                355                 360                 365

Asn Ser Thr Ala Asp Asn Ile Thr Leu Pro Cys Arg Ile Lys Gln Val
                370                 375                 380

Ile Asn Met Trp Gln Glu Val Gly Lys Ala Met Tyr Ala Pro Pro Ile
385                 390                 395                 400

Arg Gly Gln Ile Asp Cys Ser Ser Asn Ile Thr Gly Leu Ile Leu Thr
                405                 410                 415

Arg Asp Gly Gly Ser Asn Ser Ser Gln Asn Glu Thr Phe Arg Pro Gly
                420                 425                 430

Gly Gly Asn Met Lys Asp Asn Trp Arg Ser Glu Leu Tyr Lys Tyr Lys
                435                 440                 445

Val Val Lys Ile Glu Pro Leu Gly Ile Ala Pro Thr Arg Ala Lys Arg
                450                 455                 460
```

Arg Val Val Gln Arg Glu Lys Arg
465                 470

<210> SEQ ID NO 28
<211> LENGTH: 476
<212> TYPE: PRT
<213> ORGANISM: Human immunodeficiency virus

<400> SEQUENCE: 28

Leu Trp Val Thr Val Tyr Tyr Gly Val Pro Val Trp Lys Glu Ala Thr
1               5                   10                  15

Thr Thr Leu Phe Cys Ala Ser Asp Ala Lys Ala Tyr Glu Thr Glu Lys
            20                  25                  30

His Asn Val Trp Ala Thr His Ala Cys Val Pro Thr Asp Pro Asp Pro
        35                  40                  45

Gln Glu Val Val Leu Gly Asn Val Thr Glu Asn Phe Asn Met Trp Lys
    50                  55                  60

Asn Asn Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Thr Asp Glu Leu Arg Asn Gly Thr Tyr Ala Asn Val Thr Val
            100                 105                 110

Thr Glu Lys Gly Glu Ile Lys Asn Cys Ser Phe Asn Ile Thr Thr Ala
        115                 120                 125

Ile Arg Asp Lys Val Gln Lys Thr Tyr Ala Leu Phe Tyr Arg Leu Asp
    130                 135                 140

Val Val Pro Ile Asp Asn Asn His Gly Asn Ser Ser Asn Tyr Ser
145                 150                 155                 160

Asn Tyr Arg Leu Ile Asn Cys Asn Thr Ser Val Ile Thr Gln Ala Cys
                165                 170                 175

Pro Lys Val Ser Phe Glu Pro Ile Pro Ile His Tyr Cys Ala Pro Ala
            180                 185                 190

Gly Phe Ala Ile Leu Lys Cys Asn Asn Lys Lys Phe Asn Gly Thr Gly
        195                 200                 205

Pro Cys Lys Asn Val Ser Thr Val Gln Cys Thr His Gly Ile Arg Pro
    210                 215                 220

Val Val Ser Thr Gln Leu Leu Leu Asn Gly Ser Leu Ala Glu Glu Glu
225                 230                 235                 240

Val Val Ile Arg Ser Glu Asn Phe Thr Asp Asn Ala Lys Thr Ile Ile
                245                 250                 255

Val Gln Leu Asn Asp Ser Val Ile Ile Asn Cys Thr Arg Pro Asn Asn
            260                 265                 270

Asn Thr Arg Lys Gly Ile Thr Ile Gly Pro Gly Arg Val Phe Tyr Thr
        275                 280                 285

Gly Glu Ile Val Gly Asp Ile Arg Gln Val His Cys Asn Leu Ser Ser
    290                 295                 300

Ala Lys Trp Asn Ser Thr Leu Lys Gln Val Val Thr Lys Leu Arg Glu
305                 310                 315                 320

Gln Phe Gly Asn Lys Thr Ile Val Phe Asn Gln Ser Ser Gly Gly Asp
                325                 330                 335

Pro Glu Ile Val Met His Ser Phe Asn Cys Gly Gly Glu Phe Phe Phe
            340                 345                 350

Cys Asn Thr Thr Gln Leu Phe Asn Ser Thr Trp Asn Ile Asn Gly Thr

```
                    355                 360                 365
Trp His Gly Thr Thr Val Ser Asn Lys Thr Ile Ile Leu Pro Cys Arg
    370                 375                 380

Ile Lys Gln Ile Ile Asn Met Trp Gln Glu Val Gly Lys Ala Met Tyr
385                 390                 395                 400

Ala Pro Pro Ile Arg Gly Gln Ile Arg Cys Ser Ser Asn Ile Thr Gly
                405                 410                 415

Leu Leu Leu Thr Arg Asp Gly Gly Asn Asn Ser Thr Thr Glu Ile
                420                 425                 430

Phe Arg Pro Gly Gly Gly Asp Met Arg Asp Asn Trp Arg Ser Glu Leu
            435                 440                 445

Tyr Lys Tyr Lys Val Val Lys Ile Glu Pro Leu Gly Ile Ala Pro Thr
    450                 455                 460

Lys Ala Arg Arg Arg Val Val Gln Arg Glu Lys Arg
465                 470                 475

<210> SEQ ID NO 29
<211> LENGTH: 490
<212> TYPE: PRT
<213> ORGANISM: Human immunodeficiency virus

<400> SEQUENCE: 29

Leu Trp Val Thr Val Tyr Tyr Gly Val Pro Val Trp Lys Glu Ala Thr
1               5                   10                  15

Thr Thr Leu Phe Cys Ala Ser Asp Ala Lys Ala Tyr Glu Thr Glu Lys
                20                  25                  30

His Asn Val Trp Ala Thr His Ala Cys Val Pro Thr Asp Pro Asn Pro
            35                  40                  45

Gln Glu Val Val Leu Gly Asn Val Thr Glu Asn Phe Asn Met Trp Lys
50                  55                  60

Asn Asn Met Val Glu Gln Met His Glu Asp Ile Ile Ser Leu Trp Asp
65                  70                  75                  80

Glu Ser Leu Lys Pro Cys Val Lys Leu Thr Pro Leu Cys Val Thr Leu
                85                  90                  95

Asn Cys Thr Asp Glu Val Lys Ser Tyr Ala Asn Lys Thr Ser Asn
            100                 105                 110

Glu Thr Tyr Lys Thr Ser Asn Glu Thr Phe Gly Glu Ile Lys Asn Cys
            115                 120                 125

Ser Phe Ser Val Pro Thr Gly Ile Lys Asp Lys Val Gln Asn Val Tyr
130                 135                 140

Ala Leu Phe Tyr Lys Leu Asp Val Ile Pro Ile Asp Asp Asn Asn Asn
145                 150                 155                 160

Ser Ser Lys Asn Asn Gly Ser Tyr Ser Tyr Arg Leu Ile Asn
                165                 170                 175

Cys Asn Thr Ser Val Ile Thr Gln Ala Cys Pro Lys Val Ser Phe Glu
            180                 185                 190

Pro Ile Pro Ile His Tyr Cys Ala Pro Ala Gly Phe Ala Ile Leu Lys
            195                 200                 205

Cys Asn Asn Lys Thr Phe Asn Gly Thr Gly Pro Cys Thr Asn Val Ser
210                 215                 220

Thr Val Gln Cys Thr His Gly Ile Arg Pro Val Val Ser Thr Gln Leu
225                 230                 235                 240

Leu Leu Asn Gly Ser Leu Ala Glu Glu Val Val Ile Arg Ser Glu
                245                 250                 255
```

```
Asn Phe Thr Asn Asn Ala Lys Thr Ile Ile Val His Leu Lys Lys Ser
                260                 265                 270

Val Glu Ile Asn Cys Thr Arg Pro Gly Asn Asn Thr Arg Lys Ser Ile
            275                 280                 285

His Ile Gly Pro Gly Arg Ala Phe Tyr Ala Thr Gly Asp Ile Ile Gly
        290                 295                 300

Asp Ile Arg Gln Ala His Cys Asn Leu Ser Ser Val Gln Trp Asn Asp
305                 310                 315                 320

Thr Leu Lys Gln Ile Val Ile Lys Leu Gly Glu Gln Phe Gly Thr Asn
                325                 330                 335

Lys Thr Ile Ala Phe Asn Gln Ser Ser Gly Gly Asp Pro Glu Ile Val
            340                 345                 350

Met His Ser Phe Asn Cys Gly Gly Glu Phe Phe Tyr Cys Asn Thr Thr
        355                 360                 365

Gln Leu Phe Asn Ser Thr Trp Glu Phe His Gly Asn Trp Thr Arg Ser
370                 375                 380

Asn Phe Thr Glu Ser Asn Ser Thr Thr Ile Thr Leu Pro Cys Arg Ile
385                 390                 395                 400

Lys Gln Ile Val Asn Met Trp Gln Glu Val Gly Lys Ala Met Tyr Ala
                405                 410                 415

Pro Pro Ile Arg Gly Gln Ile Arg Cys Ser Ser Asn Ile Thr Gly Leu
            420                 425                 430

Leu Leu Thr Arg Asp Gly Gly Val Asn Gly Thr Arg Glu Thr Phe Arg
        435                 440                 445

Pro Gly Gly Gly Asp Met Arg Asp Asn Trp Arg Ser Glu Leu Tyr Lys
450                 455                 460

Tyr Lys Val Val Lys Ile Glu Pro Leu Gly Val Ala Pro Thr Lys Ala
465                 470                 475                 480

Lys Arg Arg Val Val Gln Arg Glu Lys Arg
                485                 490

<210> SEQ ID NO 30
<211> LENGTH: 471
<212> TYPE: PRT
<213> ORGANISM: Human immunodeficiency virus

<400> SEQUENCE: 30

Leu Trp Val Thr Val Tyr Tyr Gly Val Pro Val Trp Lys Glu Thr Thr
1               5                   10                  15

Thr Thr Leu Phe Cys Ala Ser Asp Ala Lys Ala Tyr Asp Thr Glu Val
            20                  25                  30

His Asn Val Trp Ala Thr His Ala Cys Val Pro Thr Asp Pro Asn Pro
        35                  40                  45

Gln Glu Val Val Leu Glu Asn Val Thr Glu Asp Phe Asn Met Trp Lys
    50                  55                  60

Asn Asn Met Val Glu Gln Met Gln Glu Asp Val Ile Asn Leu Trp Asp
65                  70                  75                  80

Gln Ser Leu Lys Pro Cys Val Lys Leu Thr Pro Leu Cys Val Thr Leu
                85                  90                  95

Asn Cys Lys Asp Val Asn Ala Thr Asn Thr Thr Ser Ser Ser Glu Gly
            100                 105                 110

Met Met Glu Arg Gly Glu Ile Lys Asn Cys Ser Phe Asn Ile Thr Lys
        115                 120                 125

Ser Ile Arg Asp Lys Val Gln Lys Glu Tyr Ala Leu Phe Tyr Lys Leu
130                 135                 140
```

```
Asp Val Val Pro Ile Asp Asn Lys Asn Thr Lys Tyr Arg Leu Ile
145                 150                 155                 160

Ser Cys Asn Thr Ser Val Ile Thr Gln Ala Cys Pro Lys Val Ser Phe
            165                 170                 175

Glu Pro Ile Pro Ile His Tyr Cys Ala Pro Ala Gly Phe Ala Ile Leu
            180                 185                 190

Lys Cys Asn Asn Lys Thr Phe Asn Gly Lys Gly Gln Cys Lys Asn Val
            195                 200                 205

Ser Thr Val Gln Cys Thr His Gly Ile Arg Pro Val Val Ser Thr Gln
            210                 215                 220

Leu Leu Leu Asn Gly Ser Leu Ala Glu Glu Lys Val Val Ile Arg Ser
225                 230                 235                 240

Asp Asn Phe Thr Asp Asn Ala Lys Thr Ile Ile Val Gln Leu Asn Glu
            245                 250                 255

Ser Val Lys Ile Asn Cys Thr Arg Pro Ser Asn Asn Thr Arg Lys Ser
            260                 265                 270

Ile His Ile Gly Pro Gly Arg Ala Phe Tyr Thr Thr Gly Glu Ile Ile
            275                 280                 285

Gly Asp Ile Arg Gln Ala His Cys Asn Ile Ser Arg Ala Gln Trp Asn
            290                 295                 300

Asn Thr Leu Lys Gln Ile Val Glu Lys Leu Arg Glu Gln Phe Asn Asn
305                 310                 315                 320

Lys Thr Ile Val Phe Thr His Ser Ser Gly Gly Asp Pro Glu Ile Val
            325                 330                 335

Met His Ser Phe Asn Cys Gly Gly Glu Phe Phe Tyr Cys Asn Ser Thr
            340                 345                 350

Gln Leu Phe Asn Ser Thr Trp Asn Asp Thr Glu Lys Ser Ser Gly Thr
            355                 360                 365

Glu Gly Asn Asp Thr Ile Ile Leu Pro Cys Arg Ile Lys Gln Ile Ile
            370                 375                 380

Asn Met Trp Gln Glu Val Gly Lys Ala Met Tyr Ala Pro Pro Ile Lys
385                 390                 395                 400

Gly Gln Ile Arg Cys Ser Ser Asn Ile Thr Gly Leu Leu Leu Thr Arg
            405                 410                 415

Asp Gly Gly Lys Asn Glu Ser Glu Ile Glu Ile Phe Arg Pro Gly Gly
            420                 425                 430

Gly Asp Met Arg Asp Asn Trp Arg Ser Glu Leu Tyr Lys Tyr Lys Val
            435                 440                 445

Val Lys Ile Glu Pro Leu Gly Val Ala Pro Thr Lys Ala Lys Arg Arg
            450                 455                 460

Val Val Gln Arg Glu Lys Arg
465                 470

<210> SEQ ID NO 31
<211> LENGTH: 470
<212> TYPE: PRT
<213> ORGANISM: Human immunodeficiency virus

<400> SEQUENCE: 31

Leu Trp Val Thr Val Tyr Tyr Gly Val Pro Val Trp Lys Glu Ala Thr
1               5                   10                  15

Thr Thr Leu Phe Cys Ala Ser Asp Ala Lys Ala Tyr Asp Thr Glu Val
            20                  25                  30

His Asn Val Trp Ala Thr His Ala Cys Val Pro Thr Asp Pro Asn Pro
```

```
            35                  40                  45
Gln Glu Val Val Leu Glu Asn Val Thr Glu His Phe Asn Met Trp Lys
 50                  55                  60

Asn Asn Met Val Glu Gln Met Gln Glu Asp Ile Ile Ser Leu Trp Asp
 65                  70                  75                  80

Gln Ser Leu Lys Pro Cys Val Lys Leu Thr Pro Leu Cys Val Thr Leu
                 85                  90                  95

Asn Cys Lys Asp Val Asn Ala Thr Asn Thr Asn Asp Ser Glu Gly
                100                 105                 110

Thr Met Glu Arg Gly Glu Ile Lys Asn Cys Ser Phe Asn Ile Thr Thr
            115                 120                 125

Ser Ile Arg Asp Glu Val Gln Lys Glu Tyr Ala Leu Phe Tyr Lys Leu
        130                 135                 140

Asp Val Val Pro Ile Asp Asn Asn Thr Ser Tyr Arg Leu Ile Ser
145                 150                 155                 160

Cys Asp Thr Ser Val Ile Thr Gln Ala Cys Pro Lys Ile Ser Phe Glu
                165                 170                 175

Pro Ile Pro Ile His Tyr Cys Ala Pro Ala Gly Phe Ala Ile Leu Lys
                180                 185                 190

Cys Asn Asp Lys Thr Phe Asn Gly Lys Gly Pro Cys Lys Asn Val Ser
            195                 200                 205

Thr Val Gln Cys Thr His Gly Ile Arg Pro Val Val Ser Thr Gln Leu
        210                 215                 220

Leu Leu Asn Gly Ser Leu Ala Glu Glu Val Val Ile Arg Ser Asp
225                 230                 235                 240

Asn Phe Thr Asn Asn Ala Lys Thr Ile Ile Val Gln Leu Lys Glu Ser
                245                 250                 255

Val Glu Ile Asn Cys Thr Arg Pro Asn Asn Thr Arg Lys Ser Ile
                260                 265                 270

His Ile Gly Pro Gly Arg Ala Phe Tyr Thr Thr Gly Glu Ile Ile Gly
            275                 280                 285

Asp Ile Arg Gln Ala His Cys Asn Ile Ser Arg Ala Lys Trp Asn Asp
290                 295                 300

Thr Leu Lys Gln Ile Val Ile Lys Leu Arg Glu Gln Phe Glu Asn Lys
305                 310                 315                 320

Thr Ile Val Phe Asn His Ser Ser Gly Gly Asp Pro Glu Ile Val Met
                325                 330                 335

His Ser Phe Asn Cys Gly Gly Glu Phe Phe Tyr Cys Asn Ser Thr Gln
            340                 345                 350

Leu Phe Asn Ser Thr Trp Asn Asn Thr Glu Gly Ser Asn Asn Thr
        355                 360                 365

Glu Gly Asn Thr Ile Thr Leu Pro Cys Arg Ile Lys Gln Ile Ile Asn
        370                 375                 380

Met Trp Gln Glu Val Gly Lys Ala Met Tyr Ala Pro Pro Ile Arg Gly
385                 390                 395                 400

Gln Ile Arg Cys Ser Ser Asn Ile Thr Gly Leu Leu Leu Thr Arg Asp
                405                 410                 415

Gly Gly Ile Asn Glu Asn Gly Thr Glu Ile Phe Arg Pro Gly Gly Gly
                420                 425                 430

Asp Met Arg Asp Asn Trp Arg Ser Glu Leu Tyr Lys Tyr Lys Val Val
            435                 440                 445

Lys Ile Glu Pro Leu Gly Val Ala Pro Thr Lys Ala Lys Arg Arg Val
450                 455                 460
```

```
Val Gln Arg Glu Lys Arg
465             470
```

<210> SEQ ID NO 32
<211> LENGTH: 476
<212> TYPE: PRT
<213> ORGANISM: Human immunodeficiency virus

<400> SEQUENCE: 32

```
Leu Trp Val Thr Val Tyr Tyr Gly Val Pro Val Trp Lys Glu Ala Thr
1               5                   10                  15

Thr Thr Leu Phe Cys Ala Ser Asp Ala Lys Ala Tyr Asp Thr Glu Val
            20                  25                  30

His Asn Val Trp Ala Thr His Ala Cys Val Pro Thr Asp Pro Asn Pro
        35                  40                  45

Gln Glu Val Lys Met Glu Asn Val Thr Glu Asn Phe Asn Met Trp Lys
    50                  55                  60

Asn Asn Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Thr Asp Leu Arg Asn Ala Thr Ser Arg Asn Val Thr Asn Thr
            100                 105                 110

Thr Ser Ser Ser Arg Gly Met Val Gly Gly Glu Met Lys Asn Cys
        115                 120                 125

Ser Phe Asn Ile Thr Thr Gly Ile Arg Gly Lys Val Gln Lys Glu Tyr
    130                 135                 140

Ala Leu Phe Tyr Glu Leu Asp Ile Val Pro Ile Asp Asn Lys Ile Asp
145                 150                 155                 160

Arg Tyr Arg Leu Ile Ser Cys Asn Thr Ser Val Ile Thr Gln Ala Cys
                165                 170                 175

Pro Lys Val Ser Phe Glu Pro Ile Pro Ile His Tyr Cys Ala Pro Ala
            180                 185                 190

Gly Phe Ala Ile Leu Lys Cys Lys Asp Lys Lys Phe Asn Gly Lys Gly
        195                 200                 205

Pro Cys Thr Asn Val Ser Thr Val Gln Cys Thr His Gly Ile Arg Pro
    210                 215                 220

Val Val Ser Thr Gln Leu Leu Leu Asn Gly Ser Leu Ala Glu Glu Glu
225                 230                 235                 240

Val Val Ile Arg Ser Glu Asn Phe Thr Asn Asn Ala Lys Ile Ile Ile
                245                 250                 255

Val Gln Leu Asn Glu Ser Val Glu Ile Asn Cys Thr Arg Pro Asn Asn
            260                 265                 270

Asn Thr Arg Lys Ser Ile His Ile Gly Pro Gly Arg Ala Phe Tyr Thr
        275                 280                 285

Thr Gly Glu Ile Ile Gly Asp Ile Arg Gln Ala His Cys Asn Leu Ser
    290                 295                 300

Arg Ala Lys Trp Asn Asp Thr Leu Asn Lys Ile Val Ile Lys Leu Arg
305                 310                 315                 320

Glu Gln Phe Gly Asn Lys Thr Ile Val Phe Lys His Ser Ser Gly Gly
                325                 330                 335

Asp Pro Glu Ile Val Thr His Ser Phe Asn Cys Gly Gly Glu Phe Phe
            340                 345                 350

Tyr Cys Asn Ser Thr Gln Leu Phe Asn Ser Thr Trp Asn Val Thr Glu
```

-continued

```
                355                 360                 365
Glu Ser Asn Asn Thr Val Glu Asn Asn Thr Ile Thr Leu Pro Cys Arg
370                 375                 380

Ile Lys Gln Ile Ile Asn Met Trp Gln Glu Val Gly Arg Ala Met Tyr
385                 390                 395                 400

Ala Pro Pro Ile Arg Gly Gln Ile Arg Cys Ser Ser Asn Ile Thr Gly
                405                 410                 415

Leu Leu Leu Thr Arg Asp Gly Gly Pro Glu Asp Asn Lys Thr Glu Val
                420                 425                 430

Phe Arg Pro Gly Gly Gly Asp Met Arg Asp Asn Trp Arg Ser Glu Leu
                435                 440                 445

Tyr Lys Tyr Lys Val Val Lys Ile Glu Pro Leu Gly Val Ala Pro Thr
                450                 455                 460

Lys Ala Lys Arg Arg Val Val Gln Arg Glu Lys Arg
465                 470                 475

<210> SEQ ID NO 33
<211> LENGTH: 478
<212> TYPE: PRT
<213> ORGANISM: Human immunodeficiency virus

<400> SEQUENCE: 33

Leu Trp Val Thr Val Tyr Tyr Gly Val Pro Val Trp Lys Glu Ala Thr
1               5                   10                  15

Thr Thr Leu Phe Cys Ala Ser Asp Ala Lys Ala Tyr Asp Thr Glu Val
                20                  25                  30

His Asn Val Trp Ala Thr His Ala Cys Val Pro Thr Asp Pro Asn Pro
                35                  40                  45

Gln Glu Val Val Leu Val Asn Val Thr Glu Asn Phe Asn Met Trp Lys
    50                  55                  60

Asn Asp Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Ser Leu
                85                  90                  95

Lys Cys Thr Asp Leu Lys Asn Asp Thr Asn Thr Asn Ser Ser Ser Gly
                100                 105                 110

Arg Met Ile Met Glu Lys Gly Glu Ile Lys Asn Cys Ser Phe Asn Ile
            115                 120                 125

Ser Thr Ser Ile Arg Gly Lys Val Gln Lys Glu Tyr Ala Phe Phe Tyr
130                 135                 140

Lys Leu Asp Ile Ile Pro Ile Asp Asn Asp Thr Thr Ser Tyr Lys Leu
145                 150                 155                 160

Thr Ser Cys Asn Thr Ser Val Ile Thr Gln Ala Cys Pro Lys Val Ser
                165                 170                 175

Phe Glu Pro Ile Pro Ile His Tyr Cys Ala Pro Ala Gly Phe Ala Ile
                180                 185                 190

Leu Lys Cys Asn Asn Lys Thr Phe Asn Gly Thr Gly Pro Cys Thr Asn
                195                 200                 205

Val Ser Thr Val Gln Cys Thr His Gly Ile Arg Pro Val Val Ser Thr
            210                 215                 220

Gln Leu Leu Leu Asn Gly Ser Leu Ala Glu Glu Glu Val Val Ile Arg
225                 230                 235                 240

Ser Val Asn Phe Thr Asp Asn Ala Lys Thr Ile Ile Val Gln Leu Asn
                245                 250                 255
```

-continued

```
Thr Ser Val Glu Ile Asn Cys Thr Arg Pro Asn Asn Asn Thr Arg Lys
            260                 265                 270

Arg Ile Arg Ile Gln Arg Gly Pro Gly Arg Ala Phe Val Thr Ile Gly
        275                 280                 285

Lys Ile Gly Asn Met Arg Gln Ala His Cys Asn Ile Ser Arg Ala Lys
    290                 295                 300

Trp Asn Asn Thr Leu Lys Gln Ile Ala Ser Lys Leu Arg Glu Gln Phe
305                 310                 315                 320

Gly Asn Asn Lys Thr Ile Ile Phe Lys Gln Ser Ser Gly Gly Asp Pro
                325                 330                 335

Glu Ile Val Thr His Ser Phe Asn Cys Gly Gly Glu Phe Phe Tyr Cys
            340                 345                 350

Asn Ser Thr Gln Leu Phe Asn Ser Thr Trp Phe Asn Ser Thr Trp Ser
        355                 360                 365

Thr Glu Gly Ser Asn Asn Thr Glu Gly Ser Asp Thr Ile Thr Leu Pro
    370                 375                 380

Cys Arg Ile Lys Gln Ile Ile Asn Met Trp Gln Lys Val Gly Lys Ala
385                 390                 395                 400

Met Tyr Ala Pro Pro Ile Ser Gly Gln Ile Arg Cys Ser Ser Asn Ile
                405                 410                 415

Thr Gly Leu Leu Leu Thr Arg Asp Gly Gly Asn Ser Asn Asn Glu Ser
            420                 425                 430

Glu Ile Phe Arg Pro Gly Gly Gly Asp Met Arg Asp Asn Trp Arg Ser
        435                 440                 445

Glu Leu Tyr Lys Tyr Lys Val Val Lys Ile Glu Pro Leu Gly Val Ala
    450                 455                 460

Pro Thr Lys Ala Lys Arg Arg Val Val Gln Arg Glu Lys Arg
465                 470                 475

<210> SEQ ID NO 34
<211> LENGTH: 470
<212> TYPE: PRT
<213> ORGANISM: Human immunodeficiency virus

<400> SEQUENCE: 34

Leu Trp Val Thr Val Tyr Tyr Gly Val Pro Val Trp Lys Glu Ala Thr
1               5                   10                  15

Thr Thr Leu Phe Cys Ala Ser Asp Ala Lys Ala Tyr Asp Thr Glu Val
            20                  25                  30

His Asn Val Trp Ala Thr His Ala Cys Val Pro Thr Asp Pro Asn Pro
        35                  40                  45

Gln Glu Ile Val Leu Glu Asn Val Thr Glu Asn Phe Asn Met Trp Lys
    50                  55                  60

Asn Asn Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

His Cys Thr Asn Leu Lys Asn Ala Thr Asn Thr Lys Ser Ser Asn Trp
            100                 105                 110

Lys Glu Met Asp Arg Gly Glu Ile Lys Asn Cys Ser Phe Lys Val Thr
        115                 120                 125

Thr Ser Ile Arg Asn Lys Met Gln Lys Glu Tyr Ala Leu Phe His Lys
    130                 135                 140

Leu Asp Val Val Pro Ile Asp Asn Asp Asn Thr Ser Tyr Lys Leu Ile
145                 150                 155                 160
```

```
Asn Cys Asn Thr Ser Val Ile Thr Gln Ala Cys Pro Lys Val Ser Phe
            165                 170                 175

Glu Pro Ile Pro Ile His Tyr Cys Ala Pro Ala Gly Phe Ala Ile Leu
        180                 185                 190

Lys Cys Asn Asp Lys Lys Phe Asn Gly Ser Gly Pro Cys Thr Asn Val
            195                 200                 205

Ser Thr Val Gln Cys Thr His Gly Ile Arg Pro Val Val Ser Thr Gln
210                 215                 220

Leu Leu Leu Asn Gly Ser Leu Ala Glu Glu Gly Val Val Ile Arg Ser
225                 230                 235                 240

Glu Asn Phe Thr Asp Asn Ala Lys Thr Ile Ile Val Gln Leu Lys Glu
            245                 250                 255

Ser Val Glu Ile Asn Cys Thr Arg Pro Asn Asn Asn Thr Arg Lys Ser
        260                 265                 270

Ile Thr Ile Gly Pro Gly Arg Ala Phe Tyr Ala Thr Gly Asp Ile Ile
            275                 280                 285

Gly Asp Ile Arg Gln Ala His Cys Asn Ile Ser Gly Glu Lys Trp Asn
290                 295                 300

Asn Thr Leu Lys Gln Ile Val Thr Lys Leu Gln Ala Gln Phe Gly Asn
305                 310                 315                 320

Lys Thr Ile Val Phe Lys Gln Ser Ser Gly Gly Asp Pro Glu Ile Val
                325                 330                 335

Met His Ser Phe Asn Cys Gly Gly Glu Phe Phe Tyr Cys Asn Ser Thr
            340                 345                 350

Gln Leu Phe Asn Ser Thr Trp Asn Thr Ile Gly Pro Asn Asn Thr
        355                 360                 365

Asn Gly Thr Ile Thr Leu Pro Cys Arg Ile Lys Gln Ile Ile Asn Arg
            370                 375                 380

Trp Gln Glu Val Gly Lys Ala Met Tyr Ala Pro Pro Ile Arg Gly Gln
385                 390                 395                 400

Ile Arg Cys Ser Ser Asn Ile Thr Gly Leu Leu Leu Thr Arg Asp Gly
                405                 410                 415

Gly Lys Glu Ile Ser Asn Thr Thr Glu Ile Phe Arg Pro Gly Gly Gly
            420                 425                 430

Asp Met Arg Asp Asn Trp Arg Ser Glu Leu Tyr Lys Tyr Lys Val Val
        435                 440                 445

Lys Ile Glu Pro Leu Gly Val Ala Pro Thr Lys Ala Lys Arg Arg Val
    450                 455                 460

Val Gln Arg Glu Lys Arg
465                 470

<210> SEQ ID NO 35
<211> LENGTH: 481
<212> TYPE: PRT
<213> ORGANISM: Human immunodeficiency virus

<400> SEQUENCE: 35

Trp Val Thr Val Tyr Tyr Gly Val Pro Val Trp Lys Glu Ala Asn Thr
1               5                   10                  15

Thr Leu Phe Cys Ala Ser Asp Ala Lys Ala Tyr Asn Thr Glu Val His
            20                  25                  30

Asn Val Trp Ala Thr His Ala Cys Val Pro Thr Asp Pro Asn Pro Gln
        35                  40                  45

Glu Val Glu Leu Glu Asn Val Thr Glu Asn Phe Asn Met Trp Lys Asn
```

```
            50                  55                  60
Asn Met Val Asp Gln Met His Glu Asp Ile Ile Ser Leu Trp Asp Gln
 65                  70                  75                  80

Ser Leu Lys Pro Cys Val Lys Leu Thr Pro Leu Cys Val Thr Leu Ser
                 85                  90                  95

Cys Thr Asp Asn Val Gly Asn Asp Thr Ser Thr Asn Asn Ser Arg Trp
                100                 105                 110

Asp Lys Met Glu Lys Gly Glu Ile Lys Asn Cys Ser Phe Asn Ile Thr
            115                 120                 125

Thr Asn Met Arg Asp Lys Met Gln Lys Gln Tyr Ala Leu Phe Tyr Lys
        130                 135                 140

Leu Asp Val Val Pro Ile Glu Glu Gly Lys Asn Asn Ser Ser Phe
145                 150                 155                 160

Thr Asp Tyr Arg Leu Ile Ser Cys Asn Thr Ser Val Ile Thr Gln Ala
                165                 170                 175

Cys Pro Lys Val Thr Phe Glu Pro Ile Pro Ile His Tyr Cys Ala Pro
            180                 185                 190

Ala Gly Phe Ala Leu Leu Lys Cys Lys Asp Lys Lys Phe Asn Gly Thr
        195                 200                 205

Gly Pro Cys Lys Asn Val Ser Thr Val Gln Cys Thr His Gly Ile Lys
210                 215                 220

Pro Val Val Ser Thr Gln Leu Leu Leu Asn Gly Ser Leu Ala Glu Glu
225                 230                 235                 240

Glu Val Val Ile Arg Ser Glu Asn Phe Ser Asn Asn Ala Arg Thr Ile
                245                 250                 255

Ile Val Gln Leu Asn Thr Ser Val Glu Ile Lys Cys Ile Arg Pro Asn
            260                 265                 270

Asn Asn Thr Arg Lys Gly Ile His Ile Gly Pro Gly Arg Ala Phe Tyr
        275                 280                 285

Thr Thr Gly Asp Ile Ile Gly Asp Ile Arg Gln Ala His Cys Asn Ile
        290                 295                 300

Ser Arg Gln Asn Trp Asn Asn Thr Leu Lys Gln Ile Ala Glu Lys Leu
305                 310                 315                 320

Arg Glu Gln Phe Gly Asn Lys Thr Ile Val Phe Arg Asn Ser Ser Gly
                325                 330                 335

Gly Asp Pro Glu Ile Val Met His Thr Phe Asn Cys Ala Gly Glu Phe
            340                 345                 350

Phe Tyr Cys Asn Thr Ala Glu Leu Phe Asn Ser Thr Trp Tyr Ala Asn
        355                 360                 365

Gly Thr Ile Ser Ile Gly Gly Asn Lys Thr Asn Ile Ile Leu Pro
    370                 375                 380

Cys Arg Ile Lys Gln Phe Ile Asn Met Trp Gln Glu Val Gly Lys Ala
385                 390                 395                 400

Met Tyr Ala Pro Pro Ile Ser Gly Gln Ile Arg Cys Ser Ser Asn Ile
                405                 410                 415

Thr Gly Leu Leu Leu Thr Arg Asp Gly Gly Arg Gly Asn Gln Thr Asp
            420                 425                 430

Asn Gln Thr Glu Ile Phe Arg Pro Val Gly Gly Asp Met Lys Asn Asn
        435                 440                 445

Trp Arg Ser Glu Leu Tyr Lys Tyr Lys Val Val Arg Ile Glu Pro Leu
    450                 455                 460

Gly Ile Ala Pro Thr Arg Ala Lys Arg Arg Val Val Gln Arg Glu Lys
465                 470                 475                 480
```

Arg

<210> SEQ ID NO 36
<211> LENGTH: 496
<212> TYPE: PRT
<213> ORGANISM: Human immunodeficiency virus

<400> SEQUENCE: 36

```
Leu Trp Val Thr Val Tyr Tyr Gly Val Pro Val Trp Lys Glu Ala Val
1               5                   10                  15

Thr Thr Leu Phe Cys Ala Ser Asp Ala Lys Ala Tyr Asp Thr Glu Val
            20                  25                  30

His Asn Val Trp Ala Thr His Ala Cys Val Pro Thr Asp Pro Asp Pro
        35                  40                  45

Gln Glu Val Val Leu Glu Asn Val Thr Glu Asn Phe Asn Met Trp Lys
    50                  55                  60

Asn Asn Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Thr Asp Tyr Asn Asn Thr Ala Thr Asn Thr Ser Ser Ala
            100                 105                 110

Thr Thr Thr Ala Ser Ser Ala Asn Lys Thr Ala Lys Glu Glu Ala Val
        115                 120                 125

Met Lys Asn Cys Ser Phe Asn Ile Thr Thr Asn Val Arg Asp Lys Val
    130                 135                 140

Lys Arg Glu Tyr Ala Leu Phe Tyr Asn Leu Asp Val Val Lys Leu Glu
145                 150                 155                 160

Glu Gly Glu Thr Ser Tyr Arg Leu Val Ser Cys Asn Thr Ser Val Val
                165                 170                 175

Thr Gln Ala Cys Pro Lys Ile Thr Phe Glu Pro Ile Pro Ile His Tyr
            180                 185                 190

Cys Ala Pro Ala Gly Phe Ala Ile Leu Lys Cys Asn Asn Lys Thr Phe
        195                 200                 205

Asn Gly Thr Gly Pro Cys Thr Asn Val Ser Thr Val Gln Cys Thr His
    210                 215                 220

Gly Ile Lys Pro Val Val Ser Thr Gln Leu Leu Leu Asn Gly Ser Leu
225                 230                 235                 240

Ala Glu Gly Gly Glu Val Met Ile Arg Ser Ala Asn Phe Thr Asn Asn
                245                 250                 255

Ala Lys Thr Ile Ile Val Gln Leu Ser Lys Ser Val Ala Ile Asn Cys
            260                 265                 270

Thr Arg Pro Asn Asn Thr Ser Lys Ser Ile His Met Gly Pro Gly
        275                 280                 285

Gly Ala Phe Phe Ala Thr Gly Arg Ile Ile Gly Asp Ile Arg Lys Ala
    290                 295                 300

Tyr Cys Thr Val Asn Gly Thr Glu Trp Asn Thr Thr Leu Arg Gln Ile
305                 310                 315                 320

Val Glu Lys Phe Lys Lys Gln Phe Gly Glu Asn Lys Thr Ile Val Phe
                325                 330                 335

Lys Pro Ser Ala Gly Gly Asp Pro Glu Ile Val Thr His Ser Phe Asn
            340                 345                 350

Cys Gly Gly Glu Phe Phe Tyr Cys Asn Thr Thr Asn Leu Phe Asn Ser
        355                 360                 365
```

```
Ser Ser Thr Glu Leu Asn Ser Thr Trp Ser Gly Asn Ser Asn Asp Thr
    370                 375                 380

Gly Lys Asn Asp Thr Ile Thr Leu Pro Cys Arg Ile Lys Gln Ile Ile
385                 390                 395                 400

Asn Met Trp Gln Gln Val Gly Lys Ala Met Tyr Ala Pro Pro Ile Ser
                405                 410                 415

Gly Lys Ile Asn Cys Leu Ser Asn Ile Thr Gly Leu Leu Leu Thr Arg
                420                 425                 430

Asp Gly Gly Ser Asp Gly Gly Ser Lys Asn Ser Ser Lys Asn Glu Thr
                435                 440                 445

Gly Thr Glu Ile Phe Arg Pro Gly Gly Gly Asp Met Arg Asp Asn Trp
    450                 455                 460

Arg Ser Glu Leu Tyr Lys Tyr Lys Val Val Arg Ile Glu Pro Leu Gly
465                 470                 475                 480

Val Ala Pro Thr Lys Ala Lys Arg Arg Ala Val Gln Arg Glu Lys Arg
                485                 490                 495

<210> SEQ ID NO 37
<211> LENGTH: 475
<212> TYPE: PRT
<213> ORGANISM: Human immunodeficiency virus

<400> SEQUENCE: 37

Leu Trp Val Thr Val Tyr Tyr Gly Val Pro Val Trp Lys Glu Ala Thr
1               5                   10                  15

Thr Thr Leu Phe Cys Ala Ser Asp Ala Lys Gly Tyr Glu Lys Glu Val
                20                  25                  30

His Asn Val Trp Ala Thr His Ala Cys Val Pro Thr Asp Pro Asn Pro
                35                  40                  45

Gln Glu Val Val Leu Glu Asn Val Thr Glu Asn Phe Asn Met Trp Lys
            50                  55                  60

Asn Asn Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Ser Asp Val Asn Thr Thr Ser Val Asn Thr Thr Ala Ser Ser
                100                 105                 110

Met Glu Gly Gly Glu Ile Lys Asn Cys Ser Phe Asn Thr Thr Thr Ser
            115                 120                 125

Met Ser Asp Lys Met Gln Lys Glu Tyr Ala Leu Phe Tyr Thr Leu Asp
            130                 135                 140

Val Val Pro Ile Val Lys Glu Asn Asn Thr Tyr Arg Leu Ile Ser Cys
145                 150                 155                 160

Asn Thr Ser Val Ile Thr Gln Ala Cys Pro Lys Val Ser Phe Glu Pro
                165                 170                 175

Ile Pro Ile His Tyr Cys Ala Pro Ala Gly Phe Ala Ile Leu Met Cys
                180                 185                 190

Asn Asn Lys Thr Phe Asp Gly Lys Gly Pro Cys Asn Asn Val Ser Thr
            195                 200                 205

Val Gln Cys Thr His Gly Ile Lys Pro Val Val Ser Thr Gln Leu Leu
            210                 215                 220

Leu Asn Gly Ser Leu Ala Glu Glu Val Val Ile Arg Ser Asp Asn
225                 230                 235                 240

Phe Thr Asp Asn Ala Lys Thr Ile Ile Val His Leu Asn Glu Ser Ile
```

-continued

```
                245                 250                 255
Glu Ile Thr Cys Thr Arg Pro Asn Asn Asn Thr Ser Lys Ser Ile Thr
                260                 265                 270

Ile Gly Pro Gly Arg Ala Phe Tyr Ala Thr Gly Arg Ile Ile Gly Asp
            275                 280                 285

Ile Arg Lys Ala His Cys Asn Ile Ser Gly Glu Lys Trp His Asn Ala
        290                 295                 300

Leu Glu Gln Ile Val Lys Lys Leu Gly Glu Lys Phe Glu Asn Ala Thr
    305                 310                 315                 320

Thr Ile Arg Phe Asn Gln Ser Ser Gly Gly Asp Gln Glu Ile Val Met
                325                 330                 335

His Thr Phe Asn Cys Gly Gly Glu Phe Phe Tyr Cys Asn Ser Thr Gln
                340                 345                 350

Leu Phe Asn Ser Thr Trp Trp Pro Asn Gly Thr Thr Thr Glu Trp Ser
                355                 360                 365

Asn Glu Thr Ser Asn Gly Thr Ile Thr Leu Pro Cys Arg Ile Lys Gln
            370                 375                 380

Ile Ile Asn Met Trp Gln Glu Val Gly Lys Ala Met Tyr Ala Pro Pro
385                 390                 395                 400

Ile Ser Gly Pro Ile Ser Cys Ser Ser Asn Ile Thr Gly Leu Leu Leu
                405                 410                 415

Val Arg Asp Gly Gly Asn Asp Asn Glu Thr Asn Gly Thr Glu Thr Phe
                420                 425                 430

Arg Pro Gly Gly Gly Asp Met Arg Asp Asn Trp Arg Ser Glu Leu Tyr
            435                 440                 445

Lys Tyr Lys Val Val Lys Ile Glu Pro Leu Gly Val Ala Pro Thr Lys
        450                 455                 460

Ala Lys Arg Arg Val Val Gln Arg Glu Lys Arg
    465                 470                 475

<210> SEQ ID NO 38
<211> LENGTH: 473
<212> TYPE: PRT
<213> ORGANISM: Human immunodeficiency virus

<400> SEQUENCE: 38

Leu Trp Val Thr Val Tyr Tyr Gly Val Pro Val Trp Lys Glu Ala Thr
1               5                   10                  15

Thr Thr Leu Phe Cys Ala Ser Asp Ala Lys Ala Tyr Asn Thr Glu Val
                20                  25                  30

His Asn Val Trp Ala Thr His Ala Cys Val Pro Thr Asp Pro Asn Pro
            35                  40                  45

Gln Glu Val Gly Leu Glu Asn Val Thr Glu Asn Phe Asn Met Trp Lys
        50                  55                  60

Asn Asn Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Ser Asp Leu Arg Asn Ala Thr Asn Thr Thr Asn Pro Thr Val
            100                 105                 110

Ser Ser Arg Val Ile Lys Lys Glu Met Met Gly Glu Val Lys Asn Cys
        115                 120                 125

Ser Phe Asn Val Thr Thr Asp Ile Arg Asp Arg Met Gln Lys Val Tyr
    130                 135                 140
```

```
Ala Leu Phe Tyr Arg Pro Asp Val Val Pro Ile Gln Asp His Thr Ile
145                 150                 155                 160

Glu Asn Asn Asn Thr Ile Glu Asn Asn Thr Thr Tyr Arg Leu Ile Ser
                165                 170                 175

Cys Asn Thr Ser Val Ile Thr Gln Ala Cys Pro Lys Ile Ser Phe Glu
                180                 185                 190

Pro Ile Pro Ile His Tyr Cys Thr Pro Ala Gly Phe Ala Ile Leu Lys
            195                 200                 205

Cys Asn Asp Lys Lys Phe Asn Gly Ser Gly Pro Cys Thr Asn Val Ser
        210                 215                 220

Thr Val Gln Cys Thr His Gly Ile Arg Pro Val Val Ser Thr Gln Leu
225                 230                 235                 240

Leu Leu Asn Gly Ser Arg Ala Glu Glu Glu Val Ile Ile Arg Ser Glu
                245                 250                 255

Asn Phe Thr Asn Asn Ala Lys Thr Ile Ile Val Gln Leu Asn Lys Thr
                260                 265                 270

Val Glu Ile Asn Cys Thr Arg Pro Asn Asn Asn Thr Arg Lys Ser Ile
            275                 280                 285

Ser Ile Gly Pro Gly Arg Ala Phe Tyr Ala Thr Gly Asp Ile Ile Gly
290                 295                 300

Asp Ile Arg Gln Ala His Cys Asn Leu Ser Arg Ala Glu Trp Asn Lys
305                 310                 315                 320

Thr Leu Lys Tyr Ile Ser Thr Lys Leu Arg Glu Gln Phe Gly Asn Lys
                325                 330                 335

Thr Ile Ile Phe Asn Gly Ser Ser Gly Gly Asp Pro Glu Ile Val Thr
                340                 345                 350

His Ser Phe Asn Cys Gly Gly Glu Phe Phe Tyr Cys Asn Thr Thr Lys
            355                 360                 365

Leu Phe Asn Ser Thr Trp Asp Ala Asn Gly Asn Cys Thr Gly Cys Asp
        370                 375                 380

Glu Ser Asp Gly Asn Asn Thr Ile Thr Leu Pro Cys Arg Ile Lys Gln
385                 390                 395                 400

Ile Val Asn Met Trp Gln Glu Val Gly Lys Ala Met Tyr Ala Pro Pro
                405                 410                 415

Ile Lys Gly Leu Ile Lys Cys Thr Ser Asn Ile Thr Gly Leu Leu Leu
            420                 425                 430

Thr Arg Asp Gly Gly Ala Asn Asn Thr Asn Glu Thr Phe Arg Pro Gly
        435                 440                 445

Gly Gly Asp Met Arg Asp Asn Trp Arg Ser Glu Leu Tyr Lys Tyr Lys
    450                 455                 460

Val Val Gln Ile Glu Pro Leu Gly Ile
465                 470
```